US012721590B2

(12) United States Patent
Gifford, III et al.

(10) Patent No.: US 12,721,590 B2
(45) Date of Patent: Sep. 1, 2026

(54) CLOSED-LOOP CONTROL OF HEART FAILURE INTERVENTIONAL THERAPY

(71) Applicant: Foundry Innovation & Research 1, Ltd., Dublin (IE)

(72) Inventors: Hanson S. Gifford, III, Woodside, CA (US); Mark E. Deem, Mountain View, CA (US); John Morriss, San Francisco, CA (US); Douglas S. Sutton, Pacifica, CA (US); Jeffry J. Grainger, Portola Valley, CA (US); Vijaykumar Rajasekhar, San Francisco, CA (US)

(73) Assignee: Foundry Innovation & Research 1, Ltd., Dublin (IE)

( * ) Notice: Subject to any disclaimer, the term of this patent is extended or adjusted under 35 U.S.C. 154(b) by 1165 days.

(21) Appl. No.: 17/690,091

(22) Filed: Mar. 9, 2022

(65) Prior Publication Data

US 2022/0192629 A1 Jun. 23, 2022

Related U.S. Application Data

(63) Continuation of application No. 17/162,857, filed on Jan. 29, 2021, now abandoned, which is a (Continued)

(51) Int. Cl.
*A61B 8/08* (2006.01)
*A61B 5/00* (2006.01)
(Continued)

(52) U.S. Cl.
CPC .......... *A61B 8/0891* (2013.01); *A61B 5/1076* (2013.01); *A61B 5/6882* (2013.01); *A61B 8/12* (2013.01); *A61B 8/4227* (2013.01); *A61B 8/565* (2013.01); *A61B 90/39* (2016.02); *G06T 7/11* (2017.01); *G06T 7/337* (2017.01);
(Continued)

(58) Field of Classification Search
CPC ..... A61B 8/0891; A61B 90/39; A61B 5/1076; A61B 5/6882; A61B 8/12; A61B 8/4227; A61B 8/565; G06T 7/11; G06T 7/337
See application file for complete search history.

(56) References Cited

U.S. PATENT DOCUMENTS

| | | | |
|---|---|---|---|
| 952,161 | A | 3/1910 | Whyte |
| 1,184,912 | A | 5/1916 | Armitage |

(Continued)

FOREIGN PATENT DOCUMENTS

| | | | |
|---|---|---|---|
| AU | 2013206194 | B2 | 4/2015 |
| CN | 108712880 | A | 10/2018 |

(Continued)

OTHER PUBLICATIONS

International Search Report and Written Opinion dated Jan. 19, 2021, in connection with PCT/EP2020/079939, filed Oct. 23, 2020.

(Continued)

*Primary Examiner* — John D Li
(74) *Attorney, Agent, or Firm* — Downs Rachlin Martin PLLC

(57) ABSTRACT

Systems and methods for closed-loop control of heart failure interventional therapies using closed-loop feedback from vascular implanted cardiac health status sensors are disclosed.

40 Claims, 39 Drawing Sheets

Related U.S. Application Data continuation of application No. 15/549,042, filed as application No. PCT/US2016/017902 on Feb. 12, 2016, now Pat. No. 10,905,393.

(60) Provisional application No. 62/172,516, filed on Jun. 8, 2015, provisional application No. 62/157,331, filed on May 5, 2015, provisional application No. 62/115,435, filed on Feb. 12, 2015.

(51) Int. Cl.

| | |
|---|---|
| ***A61B 5/107*** | (2006.01) |
| ***A61B 8/00*** | (2006.01) |
| ***A61B 8/12*** | (2006.01) |
| ***A61B 90/00*** | (2016.01) |
| ***A61F 2/01*** | (2006.01) |
| ***G06T 7/11*** | (2017.01) |
| ***G06T 7/33*** | (2017.01) |

(52) U.S. Cl.

CPC ........... *A61B 5/4836* (2013.01); *A61B 5/4839* (2013.01); *A61B 2090/3929* (2016.02); *A61B 2090/3987* (2016.02); *A61B 2090/3991* (2016.02); *A61F 2/01* (2013.01); *G06T 2207/10072* (2013.01); *G06T 2207/10136* (2013.01); *G06T 2207/30101* (2013.01)

(56) References Cited

U.S. PATENT DOCUMENTS

| | | | |
|---|---|---|---|
| 2,133,071 | A | 10/1938 | Anderson |
| 3,209,528 | A | 10/1965 | Zerr |
| 3,568,661 | A | 3/1971 | Franklin |
| 3,838,683 | A | 10/1974 | Kolin |
| 4,142,412 | A | 3/1979 | McLeod |
| 4,638,252 | A | 1/1987 | Bradshaw |
| RE32,361 | E | 2/1987 | Duggan |
| 4,733,669 | A | 3/1988 | Segal |
| 4,893,665 | A | 1/1990 | Reuter |
| 4,926,875 | A | 5/1990 | Rabinovitz et al. |
| 4,947,852 | A | 8/1990 | Nassi et al. |
| 5,127,404 | A | 7/1992 | Wybory et al. |
| 5,205,292 | A | 4/1993 | Czar et al. |
| 5,316,001 | A | 5/1994 | Ferek-Petric et al. |
| 5,327,713 | A | 7/1994 | Sakon |
| 5,339,816 | A | 8/1994 | Akamatsu et al. |
| 5,363,848 | A | 11/1994 | Spani et al. |
| 5,387,235 | A | 2/1995 | Chuter |
| 5,476,484 | A | 12/1995 | Hedberg |
| 5,495,852 | A | 3/1996 | Stadler et al. |
| 5,562,713 | A | 10/1996 | Silvian |
| 5,630,836 | A | 5/1997 | Prem et al. |
| 5,752,522 | A | 5/1998 | Murphy |
| 5,760,341 | A | 6/1998 | Laske |
| 5,852,926 | A | 12/1998 | Breedlove |
| 5,872,520 | A | 2/1999 | Siefert et al. |
| 5,902,308 | A | 5/1999 | Murphy |
| 5,941,198 | A | 8/1999 | Sullivan |
| 5,967,986 | A | 10/1999 | Cimochowski |
| 5,971,933 | A | 10/1999 | Gopakumaran |
| 6,010,511 | A | 1/2000 | Murphy |
| 6,012,457 | A | 1/2000 | Lesh |
| 6,015,386 | A | 1/2000 | Kensey et al. |
| 6,015,387 | A | 1/2000 | Schwartz et al. |
| 6,025,725 | A | 2/2000 | Gershenfeld et al. |
| 6,039,701 | A | 3/2000 | Sliwa et al. |
| 6,053,873 | A | 4/2000 | Govari et al. |
| 6,111,520 | A | 8/2000 | Allen et al. |
| 6,115,633 | A | 9/2000 | Lang et al. |
| 6,115,636 | A | 9/2000 | Ryan |
| 6,164,283 | A | 12/2000 | Lesh |
| 6,165,135 | A | 12/2000 | Neff |
| 6,206,835 | B1 | 3/2001 | Spillman, Jr. et al. |
| 6,231,516 | B1 | 5/2001 | Keilman et al. |
| 6,261,233 | B1 | 7/2001 | Kantorovich |
| 6,272,830 | B1 | 8/2001 | Morgan |
| 6,278,379 | B1 | 8/2001 | Allen et al. |
| 6,287,253 | B1 | 9/2001 | Ortega et al. |
| 6,325,762 | B1 | 12/2001 | Tjin |
| 6,339,816 | B1 | 1/2002 | Bausch |
| 6,354,999 | B1 | 3/2002 | Dgany et al. |
| 6,398,734 | B1 | 6/2002 | Cimochowski et al. |
| 6,434,411 | B1 | 8/2002 | Duret |
| 6,503,202 | B1 | 1/2003 | Hossack et al. |
| 6,574,510 | B2 | 6/2003 | Von Arx et al. |
| 6,673,020 | B2 | 1/2004 | Okada et al. |
| 6,673,596 | B1 * | 1/2004 | Sayler ...................... C12Q 1/66 435/7.1 |
| 6,699,186 | B1 | 3/2004 | Wolinsky et al. |
| 6,738,671 | B2 | 5/2004 | Christophersom et al. |
| 6,802,811 | B1 | 10/2004 | Slepian |
| 6,855,115 | B2 | 2/2005 | Fonseca et al. |
| 6,926,670 | B2 | 8/2005 | Rich et al. |
| 6,972,553 | B2 | 12/2005 | Petrovich et al. |
| 7,065,409 | B2 | 6/2006 | Mazar |
| 7,077,812 | B2 | 7/2006 | Naghavi |
| 7,082,330 | B2 | 7/2006 | Stadler et al. |
| 7,147,604 | B1 | 12/2006 | Allen et al. |
| 7,149,587 | B2 | 12/2006 | Wardle et al. |
| 7,191,013 | B1 | 3/2007 | Miranda et al. |
| 7,225,032 | B2 | 5/2007 | Schmeling et al. |
| 7,233,821 | B2 | 6/2007 | Hettrick |
| 7,236,821 | B2 | 6/2007 | Cates et al. |
| 7,245,117 | B1 | 7/2007 | Joy |
| 7,265,676 | B2 | 9/2007 | Gordon et al. |
| 7,284,442 | B2 | 10/2007 | Fleischman et al. |
| 7,367,984 | B2 | 5/2008 | Kulcinski et al. |
| 7,423,496 | B2 | 9/2008 | Scheuermann |
| 7,432,723 | B2 | 10/2008 | Ellis |
| 7,439,723 | B2 | 10/2008 | Allen |
| 7,444,878 | B1 | 11/2008 | Pepples |
| 7,452,334 | B2 | 11/2008 | Gianchandani et al. |
| 7,454,244 | B2 | 11/2008 | Kassab et al. |
| 7,466,120 | B2 | 12/2008 | Miller |
| 7,479,112 | B2 | 1/2009 | Sweeney et al. |
| 7,481,771 | B2 | 1/2009 | Fonseca |
| 7,492,144 | B2 | 2/2009 | Powers et al. |
| 7,498,799 | B2 | 3/2009 | Allen |
| 7,550,978 | B2 | 6/2009 | Joy |
| 7,574,792 | B2 | 8/2009 | O'Brien |
| 7,595,647 | B2 | 9/2009 | Kroh |
| 7,618,363 | B2 | 11/2009 | Yadav |
| 7,621,036 | B2 | 11/2009 | Cros |
| 7,621,876 | B2 | 11/2009 | Hoctor et al. |
| 7,647,831 | B2 | 1/2010 | Corcoran |
| 7,647,836 | B2 | 1/2010 | O'Brien |
| 7,662,653 | B2 | 2/2010 | O'Brien |
| 7,667,547 | B2 | 2/2010 | Ellis |
| 7,677,107 | B2 | 3/2010 | Nunez |
| 7,678,135 | B2 | 3/2010 | Maahs et al. |
| 7,679,355 | B2 | 3/2010 | Allen |
| 7,699,059 | B2 | 4/2010 | Fonseca et al. |
| 7,710,103 | B2 | 5/2010 | Powers |
| 7,725,160 | B2 | 5/2010 | Weber |
| 7,748,277 | B2 | 7/2010 | O'Brien |
| 7,778,684 | B2 | 8/2010 | Weber et al. |
| 7,786,867 | B2 | 8/2010 | Hamel et al. |
| 7,812,416 | B2 | 10/2010 | Courcimault |
| 7,829,363 | B2 | 11/2010 | You |
| 7,831,301 | B2 | 11/2010 | Webb et al. |
| 7,839,153 | B2 | 11/2010 | Joy |
| 7,848,813 | B2 | 12/2010 | Bergelson et al. |
| 7,854,172 | B2 | 12/2010 | O'Brien |
| 7,899,545 | B2 | 3/2011 | John |
| 7,908,002 | B2 | 3/2011 | Hoijer |
| 7,908,018 | B2 | 3/2011 | O'Brien |
| 7,909,770 | B2 | 3/2011 | Stern et al. |
| 7,932,732 | B2 | 4/2011 | Ellis |
| 7,936,174 | B2 | 5/2011 | Ellis |
| 7,955,269 | B2 | 6/2011 | Stahmann |
| 7,966,886 | B2 | 6/2011 | Corcoran et al. |
| 7,988,719 | B2 | 8/2011 | Alt et al. |

(56) References Cited

U.S. PATENT DOCUMENTS

| | | | |
|---|---|---|---|
| 8,016,766 | B2 | 9/2011 | Goedje et al. |
| 8,021,307 | B2 | 9/2011 | White |
| 8,025,625 | B2 | 9/2011 | Allen |
| 8,026,729 | B2 | 9/2011 | Kroh |
| 8,060,214 | B2 | 11/2011 | Larson et al. |
| 8,078,274 | B2 | 12/2011 | Kassab |
| 8,082,032 | B2 | 12/2011 | Kassab et al. |
| 8,099,161 | B2 | 1/2012 | Kassab |
| 8,107,248 | B2 | 1/2012 | Shin et al. |
| 8,111,150 | B2 | 2/2012 | Miller |
| 8,114,143 | B2 | 2/2012 | Kassab et al. |
| 8,118,749 | B2 | 2/2012 | White |
| 8,154,389 | B2 | 4/2012 | Rowland |
| 8,159,348 | B2 | 4/2012 | Ellis |
| 8,185,194 | B2 | 5/2012 | Kassab |
| 8,209,033 | B2 | 6/2012 | Zhang et al. |
| 8,221,405 | B2 | 7/2012 | Whisenant et al. |
| 8,237,451 | B2 | 8/2012 | Joy |
| 8,264,240 | B2 | 9/2012 | Park et al. |
| 8,267,954 | B2 | 9/2012 | Decant, Jr. et al. |
| 8,271,072 | B2 | 9/2012 | Houben et al. |
| 8,278,941 | B2 | 10/2012 | Kroh |
| 8,298,147 | B2 | 10/2012 | Huennekens et al. |
| 8,298,148 | B2 | 10/2012 | Furman |
| 8,353,841 | B2 | 1/2013 | White |
| 8,355,777 | B2 | 1/2013 | White |
| 8,356,399 | B2 | 1/2013 | Kaplan |
| 8,360,984 | B2 | 1/2013 | Yadav |
| 8,374,689 | B2 | 2/2013 | Gopinathan et al. |
| 8,414,495 | B2 | 4/2013 | Halmann |
| 8,432,265 | B2 | 4/2013 | Rowland |
| 8,442,606 | B2 | 5/2013 | Furman |
| 8,442,639 | B2 | 5/2013 | Walker et al. |
| 8,465,436 | B2 | 6/2013 | Griswold |
| 8,465,452 | B2 | 6/2013 | Kassab |
| 8,467,854 | B2 | 6/2013 | Lewis et al. |
| 8,480,594 | B2 | 7/2013 | Eigler et al. |
| 8,493,187 | B2 | 7/2013 | Rowland |
| 8,500,660 | B2 | 8/2013 | Buchwald et al. |
| 8,521,282 | B2 | 8/2013 | Czygan et al. |
| 8,527,046 | B2 | 9/2013 | Connelly et al. |
| 8,556,929 | B2 | 10/2013 | Harper et al. |
| 8,570,186 | B2 | 10/2013 | Nagy |
| 8,600,517 | B2 | 12/2013 | Forsell |
| 8,613,705 | B2 | 12/2013 | Scheurer et al. |
| 8,632,469 | B2 | 1/2014 | Kassab |
| 8,644,941 | B2 | 2/2014 | Rooney et al. |
| 8,665,086 | B2 | 3/2014 | Miller et al. |
| 8,669,770 | B2 | 3/2014 | Cros |
| 8,696,584 | B2 | 4/2014 | Kassab |
| 8,702,613 | B2 | 4/2014 | Kassab |
| 8,706,208 | B2 | 4/2014 | Chiao et al. |
| 8,706,209 | B2 | 4/2014 | Kassab |
| 8,706,219 | B2 | 4/2014 | Feldman |
| 8,728,012 | B2 | 5/2014 | Braido |
| 8,747,313 | B2 | 6/2014 | Tran et al. |
| 8,784,338 | B2 | 7/2014 | Wallace |
| 8,798,712 | B2 | 8/2014 | Gopinathan et al. |
| 8,814,798 | B2 | 8/2014 | Corbucci et al. |
| 8,818,507 | B2 | 8/2014 | Liu et al. |
| 8,825,151 | B2 | 9/2014 | Gopinathan et al. |
| 8,827,904 | B2 | 9/2014 | Ball et al. |
| 8,827,929 | B2 | 9/2014 | D'Dea |
| 8,855,783 | B2 | 10/2014 | Dagan et al. |
| 8,864,666 | B2 | 10/2014 | Kassem |
| 8,870,787 | B2 | 10/2014 | Yadav |
| 8,874,203 | B2 | 10/2014 | Kassab et al. |
| 8,886,301 | B2 | 11/2014 | Kassab |
| 8,894,582 | B2 | 11/2014 | Nunez |
| 8,896,324 | B2 | 11/2014 | Kroh |
| 8,909,351 | B2 | 12/2014 | Dinsmoor et al. |
| 8,918,169 | B2 | 12/2014 | Kassab et al. |
| 8,938,292 | B2 | 1/2015 | Hettrick et al. |
| 8,951,219 | B2 | 2/2015 | Gerber et al. |
| 9,049,995 | B2 | 6/2015 | Blomqvist et al. |
| 9,055,917 | B2 | 6/2015 | Mann et al. |
| 9,060,798 | B2 | 6/2015 | Harper et al. |
| 9,061,099 | B2 | 6/2015 | Gerber et al. |
| 9,066,672 | B2 | 6/2015 | Kassab et al. |
| 9,089,713 | B2 | 7/2015 | John et al. |
| 9,162,065 | B2 | 10/2015 | Karst et al. |
| 9,198,706 | B2 | 12/2015 | Kassab et al. |
| 9,265,428 | B2 | 2/2016 | O'Brien et al. |
| 9,289,132 | B2 | 3/2016 | Ghaffari et al. |
| 9,289,229 | B2 | 3/2016 | Kassab |
| 9,305,456 | B2 | 4/2016 | Rowland |
| 9,314,169 | B2 | 4/2016 | Kassab |
| 9,326,728 | B2 | 5/2016 | Demir et al. |
| 9,332,914 | B2 | 5/2016 | Langston |
| 9,332,916 | B2 | 5/2016 | Kassab |
| 9,333,365 | B2 | 5/2016 | Zhao |
| 9,351,661 | B2 | 5/2016 | Kassab |
| 9,392,940 | B2 | 7/2016 | Snichelotto |
| 9,393,416 | B2 | 7/2016 | Rooney et al. |
| 9,445,743 | B2 | 9/2016 | Kassab |
| 9,489,831 | B2 | 11/2016 | Nagy et al. |
| 9,526,637 | B2 | 12/2016 | Dagan et al. |
| 9,545,263 | B2 | 1/2017 | Lenihan et al. |
| 9,603,533 | B2 | 3/2017 | Lading et al. |
| 9,662,066 | B2 | 5/2017 | Ledet et al. |
| 9,675,257 | B2 | 6/2017 | Kassab |
| 9,675,315 | B2 | 6/2017 | Song et al. |
| 9,713,701 | B2 | 7/2017 | Sarkar et al. |
| RE46,494 | E | 8/2017 | Bauer |
| 9,717,475 | B2 | 8/2017 | Corl |
| 9,721,463 | B2 | 8/2017 | Rowland |
| 9,724,006 | B2 | 8/2017 | Dumont et al. |
| 9,788,739 | B2 | 10/2017 | John et al. |
| 9,814,395 | B2 | 11/2017 | Stahmann et al. |
| 9,820,673 | B2 | 11/2017 | Feldman |
| 9,872,948 | B2 | 1/2018 | Siess |
| 9,878,080 | B2 | 1/2018 | Kaiser et al. |
| 9,901,722 | B2 | 2/2018 | Nitzan et al. |
| 9,996,712 | B2 | 6/2018 | Sundaram et al. |
| 10,080,528 | B2 | 9/2018 | BeBusschere et al. |
| 10,092,247 | B2 | 10/2018 | Taylor |
| 10,105,103 | B2 | 10/2018 | Goldshtein et al. |
| 10,194,808 | B1 | 2/2019 | Thompson |
| 10,195,441 | B2 | 2/2019 | Kaiser |
| 10,201,285 | B2 | 2/2019 | Sawanoi |
| 10,210,956 | B2 | 2/2019 | Lavi |
| 10,213,129 | B2 | 2/2019 | Kassab |
| 10,219,704 | B2 | 3/2019 | Lavi |
| 10,219,720 | B2 | 3/2019 | Kassab |
| 10,219,724 | B2 | 3/2019 | Stern |
| 10,226,203 | B2 | 3/2019 | Stigall |
| 10,226,218 | B2 | 3/2019 | Rowland |
| 10,231,659 | B2 | 3/2019 | Vanslyke |
| 10,231,701 | B2 | 3/2019 | Ryan |
| 10,236,084 | B2 | 3/2019 | Grady |
| 10,238,311 | B2 | 3/2019 | Kassab |
| 10,238,322 | B2 | 3/2019 | Vanslyke |
| 10,238,323 | B2 | 3/2019 | Vanslyke |
| 10,238,324 | B2 | 3/2019 | Vanslyke |
| 10,240,994 | B1 | 3/2019 | Xu |
| 10,265,024 | B2 | 4/2019 | Lee |
| 10,271,797 | B2 | 4/2019 | Zhang |
| 10,335,042 | B2 | 7/2019 | Schoenie et al. |
| 10,390,714 | B2 | 8/2019 | Wolinsky |
| 10,433,736 | B2 | 10/2019 | Karlovsky et al. |
| 10,537,281 | B2 | 1/2020 | Thompson et al. |
| 10,542,887 | B2 | 1/2020 | Sarkar et al. |
| 10,548,535 | B2 | 2/2020 | Zhang et al. |
| 10,555,704 | B2 | 2/2020 | Averina et al. |
| 10,582,866 | B2 | 3/2020 | Badie et al. |
| 10,588,528 | B2 | 3/2020 | Banet et al. |
| 10,595,734 | B2 | 3/2020 | Thakur et al. |
| 10,596,381 | B2 | 3/2020 | Averina et al. |
| 10,638,980 | B2 | 5/2020 | Gyllensten et al. |
| 10,660,577 | B2 | 5/2020 | Thakur et al. |
| 10,687,715 | B2 | 6/2020 | Jansen et al. |
| 10,702,213 | B2 | 7/2020 | Sharma et al. |
| 10,806,352 | B2 | 10/2020 | Sweeney et al. |
| 10,905,393 | B2 | 2/2021 | Gifford, III et al. |

(56) References Cited

U.S. PATENT DOCUMENTS 11,006,845 B2 5/2021 Kuraguntla et al.
11,039,813 B2 6/2021 Gifford, III et al.
11,206,992 B2 12/2021 Sweeney et al.
11,272,840 B2 3/2022 Rothfuss
11,445,924 B2 9/2022 Joseph
11,452,497 B2 9/2022 Garza
11,564,596 B2 1/2023 Gifford et al.
11,890,082 B2 2/2024 Cros et al.
2001/0047198 A1 11/2001 Drasler et al.
2002/0120205 A1 8/2002 Ferek-Petric
2002/0188207 A1 12/2002 Richter
2003/0037591 A1 2/2003 Ashton et al.
2003/0100940 A1 5/2003 Yodfat
2003/0125797 A1 7/2003 Chobotov
2003/0135971 A1 7/2003 Liberman
2003/0158584 A1 8/2003 Cates et al.
2003/0199938 A1 10/2003 Smits et al.
2003/0216803 A1 11/2003 Ledergerber
2004/0106871 A1 6/2004 Hunyor et al.
2004/0116992 A1 6/2004 Wardle
2004/0133092 A1 7/2004 Kain
2004/0140939 A1 7/2004 Haller et al.
2004/0167596 A1 8/2004 Richter
2004/0176672 A1 9/2004 Silver et al.
2004/0215235 A1 10/2004 Jackson et al.
2005/0049686 A1 3/2005 Gray et al.
2005/0049689 A1 3/2005 Gray
2005/0137481 A1 6/2005 Sheard et al.
2005/0148903 A1 7/2005 Diamantopoulos
2005/0149119 A1 7/2005 Koyfman
2005/0154321 A1 7/2005 Wolinsky
2005/0177224 A1 8/2005 Fogarty
2005/0228486 A1 10/2005 Case
2006/0047327 A1 3/2006 Colvin et al.
2006/0056161 A1 3/2006 Shin
2006/0079793 A1 4/2006 Mann et al.
2006/0100522 A1 5/2006 Yuan et al.
2006/0106321 A1 5/2006 Lewinsky et al.
2006/0122522 A1 6/2006 Chavan et al.
2006/0149166 A1 7/2006 Zvuloni
2006/0174712 A1 8/2006 O'Brien
2006/0177956 A1 8/2006 O'Brien
2006/0178695 A1 8/2006 Decant
2006/0207414 A1 9/2006 Nye
2006/0253160 A1 11/2006 Benditt et al.
2006/0271119 A1 11/2006 Ni et al.
2006/0280351 A1 12/2006 Luping et al.
2006/0287602 A1 12/2006 Obrien et al.
2006/0287700 A1 12/2006 White
2007/0043409 A1 2/2007 Brian
2007/0088214 A1* 4/2007 Shuros ................. A61B 8/4483 600/437
2007/0129637 A1 6/2007 Wolinsky et al.
2007/0158769 A1 7/2007 You
2007/0199385 A1 8/2007 O'Brien
2007/0238998 A1 10/2007 Nycz et al.
2007/0247138 A1 10/2007 Miller et al.
2007/0249950 A1 10/2007 Piaget et al.
2007/0274565 A1 11/2007 Penner
2007/0282210 A1 12/2007 Stern
2007/0292090 A1 12/2007 Alphonse et al.
2008/0015569 A1 1/2008 Saadat
2008/0033527 A1 2/2008 Nunez et al.
2008/0077016 A1 3/2008 Sparks
2008/0097227 A1 4/2008 Zdeblick et al.
2008/0177186 A1 7/2008 Slater et al.
2008/0275350 A1 11/2008 Liao
2008/0287800 A1 11/2008 Furman
2008/0294041 A1 11/2008 Kassab
2008/0306580 A1 12/2008 Jenson
2009/0005803 A1 1/2009 Batiste
2009/0007679 A1 1/2009 Nunez
2009/0009332 A1 1/2009 Nunez
2009/0011117 A1 1/2009 Nunez
2009/0024029 A1 1/2009 Murashita
2009/0024042 A1 1/2009 Nunez
2009/0024177 A1 1/2009 Shuros et al.
2009/0030291 A1 1/2009 O'Brien
2009/0036776 A1 2/2009 Masuda et al.
2009/0062684 A1 3/2009 Gregersen et al.
2009/0105799 A1 4/2009 Hekmat et al.
2009/0149766 A1 6/2009 Shuros et al.
2009/0177225 A1 7/2009 Nunez et al.
2009/0189741 A1 7/2009 Rowland
2009/0198293 A1 8/2009 Cauller
2009/0270729 A1 10/2009 Corbucci
2009/0299427 A1 12/2009 Liu et al.
2009/0306507 A1 12/2009 Hyun et al.
2010/0056922 A1 3/2010 Florent
2010/0063375 A1 3/2010 Kassab et al.
2010/0076398 A1 3/2010 Scheurer et al.
2010/0076543 A1 3/2010 Melsheimer
2010/0094328 A1 4/2010 O'Dea et al.
2010/0113939 A1 5/2010 Mashimo et al.
2010/0121398 A1 5/2010 Bjorling et al.
2010/0168577 A1 7/2010 Vezina
2010/0222786 A1 9/2010 Kassab
2010/0262021 A1 10/2010 Yadav
2010/0262206 A1 10/2010 Zdeblick et al.
2010/0274217 A1 10/2010 Da Silva et al.
2010/0324432 A1 12/2010 Bjorling et al.
2010/0324665 A1 12/2010 Shaw
2010/0331754 A1 12/2010 Fulkerson
2011/0105863 A1 5/2011 Kroh
2011/0144967 A1 6/2011 Adirovich
2011/0160844 A1 6/2011 Haselby
2011/0178383 A1 7/2011 Kassab
2011/0184301 A1 7/2011 Holmstrom et al.
2011/0201990 A1 8/2011 Franano
2011/0214898 A1 9/2011 Huynh
2011/0224529 A1 9/2011 Lading
2011/0265908 A1 11/2011 Clerc et al.
2011/0306867 A1 12/2011 Gopinathan et al.
2012/0016207 A1 1/2012 Allen
2012/0029598 A1 2/2012 Zhao
2012/0136385 A1 5/2012 Cully
2012/0197118 A1 8/2012 Lisiecki et al.
2012/0203090 A1 8/2012 Min
2012/0203113 A1 8/2012 Skerl et al.
2012/0283811 A1 11/2012 Neilan
2012/0291788 A1 11/2012 Griswold et al.
2012/0296222 A1 11/2012 Griswold et al.
2013/0023981 A1 1/2013 Dierking
2013/0030295 A1 1/2013 Huennekens et al.
2013/0041244 A1 2/2013 Woias et al.
2013/0041251 A1 2/2013 Bailey et al.
2013/0041269 A1 2/2013 Stahmann et al.
2013/0060139 A1 3/2013 Richter
2013/0073025 A1 3/2013 Kassab
2013/0085350 A1 4/2013 Schugt et al.
2013/0096409 A1 4/2013 Hiltner et al.
2013/0167502 A1 7/2013 Wilson
2013/0178750 A1 7/2013 Sheehan et al.
2013/0178751 A1 7/2013 Min
2013/0184545 A1 7/2013 Blomqvist et al.
2013/0192611 A1 8/2013 Taepke, II
2013/0211291 A1 8/2013 Tran
2013/0222153 A1 8/2013 Rowland et al.
2013/0245469 A1 9/2013 Yadav
2013/0245745 A1 9/2013 Vong et al.
2013/0261655 A1 10/2013 Drasler et al.
2013/0274705 A1 10/2013 Burnes et al.
2013/0281800 A1 10/2013 Saroka et al.
2013/0289703 A1 10/2013 Kinkade et al.
2013/0296721 A1 11/2013 Yadav et al.
2013/0303914 A1 11/2013 Hiltner et al.
2013/0303915 A1* 11/2013 Barnard ............... A61B 8/5207 600/449
2013/0306232 A1 11/2013 Hedberg
2013/0310820 A1 11/2013 Fernandez et al.
2013/0317359 A1 11/2013 Wilson et al.
2013/0324866 A1 12/2013 Gladshtein
2013/0331678 A1 12/2013 Lading et al.
2013/0338468 A1 12/2013 Kassab

(56) References Cited

U.S. PATENT DOCUMENTS

2013/0345650 A1 12/2013 Amirouche
2014/0028467 A1 1/2014 Nagy
2014/0051965 A1 2/2014 Zdeblick et al.
2014/0066738 A1 3/2014 Kassab
2014/0073935 A1 3/2014 Rodriguez-Llorente
2014/0084943 A1 3/2014 Kroh et al.
2014/0088994 A1 3/2014 Kroh
2014/0094697 A1 4/2014 Petroff et al.
2014/0107768 A1 4/2014 Venkatasubramanian
2014/0155710 A1 6/2014 Rowland
2014/0155768 A1 6/2014 Orion et al.
2014/0155769 A1 6/2014 White
2014/0180118 A1 6/2014 Stigall
2014/0187977 A1 7/2014 Lading
2014/0188011 A1 7/2014 Wurster et al.
2014/0188127 A1 7/2014 Dubrul
2014/0200428 A1 7/2014 Kassab
2014/0236011 A1 8/2014 Fan et al.
2014/0243640 A1 8/2014 O'Dea
2014/0266935 A1 9/2014 Tankiewicz
2014/0275861 A1 9/2014 Kroh et al.
2014/0276011 A1 9/2014 Schmitt et al.
2014/0276110 A1 9/2014 Hoseit
2014/0276121 A1 9/2014 Kassab
2014/0276191 A1 9/2014 Kassab
2014/0276234 A1 9/2014 Hines
2014/0288085 A1 9/2014 Yadav
2014/0288459 A1 9/2014 Yadav et al.
2014/0306807 A1 10/2014 Rowland
2014/0330143 A1 11/2014 Kroh et al.
2014/0350348 A1 11/2014 Tee et al.
2014/0371624 A1 12/2014 Ziaie
2015/0031966 A1 1/2015 Ward et al.
2015/0045649 A1 2/2015 O'Dea et al.
2015/0051467 A1 2/2015 Corbucci et al.
2015/0065835 A1 3/2015 Kassab
2015/0065897 A1 3/2015 Bornzin et al.
2015/0088100 A1 3/2015 Oborn
2015/0133796 A1 5/2015 Yadav
2015/0141863 A1 5/2015 Kassab et al.
2015/0157268 A1 6/2015 Winshtein et al.
2015/0208929 A1 7/2015 Rowland
2015/0216425 A1 8/2015 Gladshtein et al.
2015/0223702 A1 8/2015 Vanney et al.
2015/0238121 A1 8/2015 Tu et al.
2015/0257732 A1 9/2015 Ryan
2015/0282720 A1 10/2015 Goldshtein et al.
2015/0282875 A1 10/2015 Harper et al.
2015/0290373 A1 10/2015 Rudser et al.
2015/0297110 A1 10/2015 Kassab
2015/0297111 A1 10/2015 Kassab
2015/0297112 A1 10/2015 Kassab et al.
2015/0297113 A1 10/2015 Kassab
2015/0297818 A1 10/2015 Matsubara et al.
2015/0305808 A1 10/2015 Ku et al.
2015/0313479 A1 11/2015 Stigall et al.
2015/0327786 A1 11/2015 Lading et al.
2016/0000403 A1 1/2016 Vilkomerson
2016/0015507 A1 1/2016 Johnson et al.
2016/0022216 A1 1/2016 Goldshtein et al.
2016/0022447 A1 1/2016 Kim et al.
2016/0029956 A1 2/2016 Rowland
2016/0029995 A1 2/2016 Navratil et al.
2016/0064117 A1 3/2016 Romero
2016/0081657 A1 3/2016 Rice
2016/0095535 A1 4/2016 Hettrick et al.
2016/0135787 A1 5/2016 Anderson et al.
2016/0135941 A1 5/2016 Binmoeller et al.
2016/0166232 A1 6/2016 Merritt
2016/0198981 A1 7/2016 Demir et al.
2016/0199204 A1 7/2016 Pung
2016/0210846 A1 7/2016 Rowland et al.
2016/0324443 A1 11/2016 Rowland et al.
2016/0345930 A1 12/2016 Mizukami
2016/0354032 A1 12/2016 Wariar
2016/0374710 A1 12/2016 Sinelnikov
2017/0027458 A1 2/2017 Glover
2017/0055048 A1 2/2017 Nagy et al.
2017/0055909 A1 3/2017 Schibli et al.
2017/0065186 A1 3/2017 Joseph et al.
2017/0065824 A1 3/2017 Dagan et al.
2017/0071501 A1 3/2017 Kassab
2017/0091574 A1 3/2017 Udupa
2017/0127975 A1 5/2017 Bozkurt
2017/0164840 A1 6/2017 Matsumoto
2017/0181677 A1 6/2017 Varsavsky et al.
2017/0211229 A1 7/2017 Nozaki
2017/0216508 A1 8/2017 Zilbershlag et al.
2017/0224279 A1 8/2017 Cahan et al.
2017/0232798 A1 8/2017 Suzuki
2017/0238817 A1 8/2017 Lading
2017/0290686 A1 10/2017 Sirhan et al.
2017/0332945 A1 11/2017 Gopinathan et al.
2017/0340440 A1 11/2017 Ratz
2017/0360312 A1 12/2017 Joseph
2018/0014829 A1 1/2018 Tal et al.
2018/0055386 A1 3/2018 Zielinski
2018/0064931 A1 3/2018 Clements
2018/0092631 A1 4/2018 Liou
2018/0132724 A1 5/2018 Waechter-Stehle
2018/0140851 A1 5/2018 Maile
2018/0172785 A1 6/2018 Leussler et al.
2018/0177486 A1 6/2018 Gifford et al.
2018/0220992 A1 8/2018 Gifford et al.
2018/0228951 A1 8/2018 Schwammenthal et al.
2018/0247095 A1 8/2018 Sundaram et al.
2018/0268941 A1 9/2018 Lavi et al.
2018/0269931 A1 9/2018 Hershko et al.
2018/0271371 A1 9/2018 Ziaie et al.
2018/0289488 A1 10/2018 Orth et al.
2018/0289536 A1 10/2018 Burnett
2018/0293409 A1 10/2018 Sundaram et al.
2018/0303414 A1 10/2018 Toth
2018/0326151 A1 11/2018 Halpert et al.
2018/0344917 A1 12/2018 Inhaber et al.
2019/0015013 A1 1/2019 Zhu et al.
2019/0029639 A1 1/2019 Gifford et al.
2019/0046047 A1 2/2019 Haase
2019/0053720 A1 2/2019 Sawado
2019/0053767 A1 2/2019 Yamada
2019/0059777 A1 2/2019 Aga et al.
2019/0069784 A1 3/2019 Mukkamala
2019/0069842 A1 3/2019 Rothberg
2019/0069851 A1 3/2019 Sharma
2019/0070348 A1 3/2019 Frost
2019/0076033 A1 3/2019 Sweeney
2019/0082978 A1 3/2019 Van der Horst
2019/0083030 A1 3/2019 Thakur
2019/0090760 A1 3/2019 Kinast
2019/0090763 A1 3/2019 Woerlee
2019/0090856 A1 3/2019 Van der Horst
2019/0099087 A1 4/2019 Cros
2019/0099088 A1 4/2019 Whinnett
2019/0110696 A1 4/2019 Benkowski
2019/0126014 A1 5/2019 Kapur et al.
2019/0150882 A1 5/2019 Maharbiz et al.
2019/0150884 A1 5/2019 Maharbiz et al.
2019/0167188 A1 6/2019 Gifford et al.
2019/0175035 A1 6/2019 van der Horst et al.
2019/0183354 A1 6/2019 Rowe
2019/0358393 A1 11/2019 Marbec
2019/0390403 A1 12/2019 Waterbury
2020/0000364 A1 1/2020 Doodeman et al.
2020/0013510 A1 1/2020 Despenic et al.
2020/0022588 A1 1/2020 Wariar et al.
2020/0022589 A1 1/2020 Banet et al.
2020/0029829 A1 1/2020 Banet et al.
2020/0029857 A1 1/2020 Rowland et al.
2020/0030612 A1 1/2020 Song et al.
2020/0037888 A1 2/2020 Thakur et al.
2020/0037892 A1 2/2020 Banet et al.
2020/0046299 A1 2/2020 An et al.
2020/0069857 A1 3/2020 Schwammenthal et al.
2020/0121187 A1 4/2020 Sarkar et al.

(56) References Cited

U.S. PATENT DOCUMENTS

| | | | |
|---|---|---|---|
| 2020/0123703 | A1 | 4/2020 | Smith |
| 2020/0129087 | A1 | 4/2020 | Sweeney et al. |
| 2020/0131699 | A1 | 4/2020 | Obana |
| 2020/0146577 | A1 | 5/2020 | Badie et al. |
| 2020/0170515 | A1 | 6/2020 | Wen et al. |
| 2020/0170711 | A1 | 6/2020 | Hendriks et al. |
| 2020/0187864 | A1 | 6/2020 | Sharma |
| 2020/0187865 | A1 | 6/2020 | Sharma et al. |
| 2020/0196876 | A1 | 6/2020 | Minor et al. |
| 2020/0196899 | A1 | 6/2020 | Higgins et al. |
| 2020/0196943 | A1 | 6/2020 | Minor et al. |
| 2020/0196944 | A1 | 6/2020 | Minor et al. |
| 2020/0196948 | A1 | 6/2020 | Cho et al. |
| 2020/0197178 | A1 | 6/2020 | Vecchio |
| 2020/0254161 | A1 | 8/2020 | Schwammenthal et al. |
| 2020/0345246 | A1 | 11/2020 | Hilgers et al. |
| 2021/0038094 | A1 | 2/2021 | Sweeney et al. |
| 2021/0060298 | A1 | 3/2021 | Arndt et al. |
| 2021/0113099 | A1 | 4/2021 | Rogers et al. |
| 2021/0113194 | A1 | 4/2021 | Padwal et al. |
| 2021/0177277 | A1 | 6/2021 | Cros et al. |
| 2021/0216733 | A1 | 7/2021 | Chronos et al. |
| 2021/0244381 | A1 | 8/2021 | Sweeney et al. |
| 2021/0254279 | A1 | 8/2021 | Obana |
| 2021/0401306 | A1 | 12/2021 | Sweeney |
| 2022/0071488 | A1 | 3/2022 | Andersen et al. |
| 2022/0125312 | A1 | 4/2022 | Nazari et al. |
| 2022/0193419 | A1 | 6/2022 | Sarkar et al. |
| 2022/0233084 | A1 | 7/2022 | Valdez |
| 2022/0240792 | A1 | 8/2022 | Wetterling |
| 2022/0265157 | A1 | 8/2022 | Charthad |
| 2023/0277157 | A1 | 9/2023 | Garcia et al. |
| 2024/0155147 | A1 | 5/2024 | Sun et al. |

FOREIGN PATENT DOCUMENTS

| | | | |
|---|---|---|---|
| CN | 110613449 | B | 5/2020 |
| CN | 111867672 | A | 10/2020 |
| DE | 102005035022 | A1 | 11/2006 |
| EP | 0399059 | A1 | 5/1989 |
| EP | 0538885 | A1 | 4/1993 |
| EP | 0897285 | A1 | 2/1999 |
| EP | 1162914 | A1 | 12/2001 |
| EP | 1311210 | A2 | 5/2003 |
| EP | 0904009 | B1 | 9/2003 |
| EP | 1545303 | A2 | 6/2005 |
| EP | 1677852 | A2 | 7/2006 |
| EP | 1847217 | A2 | 10/2007 |
| EP | 1851524 | A2 | 11/2007 |
| EP | 1851791 | A2 | 11/2007 |
| EP | 1868496 | A2 | 12/2007 |
| EP | 1871224 | A2 | 1/2008 |
| EP | 1893080 | A2 | 3/2008 |
| EP | 1893081 | A2 | 3/2008 |
| EP | 1893085 | A2 | 3/2008 |
| EP | 2091426 | A2 | 6/2008 |
| EP | 1948007 | | 7/2008 |
| EP | 1993438 | A1 | 11/2008 |
| EP | 2012658 | A2 | 1/2009 |
| EP | 2046242 | A2 | 4/2009 |
| EP | 2117423 | A2 | 11/2009 |
| EP | 2197344 | A1 | 6/2010 |
| EP | 2265164 | A1 | 12/2010 |
| EP | 2021757 | B1 | 4/2011 |
| EP | 2391263 | A2 | 12/2011 |
| EP | 1921983 | B1 | 1/2012 |
| EP | 2060014 | B1 | 1/2012 |
| EP | 1902529 | B1 | 6/2012 |
| EP | 1876945 | B1 | 12/2012 |
| EP | 2330968 | B1 | 4/2013 |
| EP | 2601633 | A2 | 6/2013 |
| EP | 2449960 | B1 | 10/2013 |
| EP | 2725969 | A1 | 5/2014 |
| EP | 1993436 | B1 | 6/2014 |
| EP | 3027109 | A1 | 2/2015 |
| EP | 2076170 | B1 | 4/2015 |
| EP | 2895059 | A1 | 7/2015 |
| EP | 2898470 | A1 | 7/2015 |
| EP | 2922465 | A1 | 9/2015 |
| EP | 2317912 | B1 | 11/2015 |
| EP | 1817593 | B1 | 12/2015 |
| EP | 2967432 | A2 | 1/2016 |
| EP | 2268218 | B1 | 2/2016 |
| EP | 2456502 | B1 | 4/2016 |
| EP | 2702578 | B1 | 8/2016 |
| EP | 3057075 | A1 | 8/2016 |
| EP | 2417590 | B1 | 5/2017 |
| EP | 3359021 | A1 | 8/2018 |
| EP | 3435847 | A1 | 2/2019 |
| EP | 3435862 | A1 | 2/2019 |
| EP | 3437000 | A1 | 2/2019 |
| EP | 3448330 | A1 | 3/2019 |
| EP | 3448487 | A2 | 3/2019 |
| EP | 3457911 | A1 | 3/2019 |
| EP | 3457924 | A1 | 3/2019 |
| EP | 3457928 | A1 | 3/2019 |
| EP | 3463082 | A1 | 4/2019 |
| EP | 3468462 | A1 | 4/2019 |
| EP | 3591663 | A1 | 1/2020 |
| EP | 3609392 | A1 | 2/2020 |
| EP | 3256043 | B1 | 3/2020 |
| EP | 3629921 | A1 | 4/2020 |
| EP | 3629937 | A1 | 4/2020 |
| EP | 3630275 | A1 | 4/2020 |
| EP | 3634206 | A1 | 4/2020 |
| EP | 3654835 | A1 | 5/2020 |
| EP | 3496808 | B1 | 6/2020 |
| EP | 2654560 | B1 | 7/2020 |
| EP | 3326524 | B1 | 7/2020 |
| EP | 3367884 | B1 | 7/2020 |
| EP | 3678539 | A1 | 7/2020 |
| EP | 3681389 | A1 | 7/2020 |
| EP | 3684260 | A1 | 7/2020 |
| EP | 3684464 | A1 | 7/2020 |
| EP | 2155307 | B1 | 3/2021 |
| EP | 4039173 | A1 | 8/2022 |
| FR | 3119090 | A1 | 7/2022 |
| GB | 2473529 | A | 3/2011 |
| JP | 2011234884 | A | 11/2011 |
| JP | 2024516492 | A | 4/2024 |
| WO | 1997042871 | A1 | 11/1997 |
| WO | 1998029030 | A1 | 12/1997 |
| WO | 1998035611 | A1 | 8/1998 |
| WO | 2000055579 | A2 | 9/2000 |
| WO | 2000056210 | A1 | 9/2000 |
| WO | 2001012092 | A1 | 2/2001 |
| WO | 2001013792 | A1 | 3/2001 |
| WO | 2002015823 | A2 | 2/2002 |
| WO | 2002076289 | A2 | 10/2002 |
| WO | 2003061467 | A1 | 7/2003 |
| WO | 2003061504 | A1 | 7/2003 |
| WO | 2003092495 | A1 | 11/2003 |
| WO | 2004014456 | A2 | 2/2004 |
| WO | 2004073796 | A1 | 9/2004 |
| WO | 2006049796 | A2 | 5/2006 |
| WO | 2006086113 | A2 | 8/2006 |
| WO | 2006086114 | A2 | 8/2006 |
| WO | 2005027998 | A2 | 9/2006 |
| WO | 2006094273 | A2 | 9/2006 |
| WO | 2006096582 | A1 | 9/2006 |
| WO | 2006102905 | A1 | 10/2006 |
| WO | 2006110798 | A2 | 10/2006 |
| WO | 200625215 | A2 | 11/2006 |
| WO | 2006125215 | A2 | 11/2006 |
| WO | 2007002185 | A2 | 1/2007 |
| WO | 2007002224 | A2 | 1/2007 |
| WO | 2007002225 | A2 | 1/2007 |
| WO | 2007008493 | A1 | 1/2007 |
| WO | 2007028035 | A2 | 3/2007 |
| WO | 2007035332 | A1 | 3/2007 |
| WO | 2007047571 | A2 | 4/2007 |
| WO | 2007047794 | A2 | 4/2007 |
| WO | 2007061841 | A2 | 5/2007 |
| WO | 2007106490 | A2 | 9/2007 |

(56) References Cited

FOREIGN PATENT DOCUMENTS

| | | | |
|---|---|---|---|
| WO | 2007106533 | A1 | 9/2007 |
| WO | 2007130628 | A2 | 11/2007 |
| WO | 2008031011 | A1 | 3/2008 |
| WO | 2008031095 | A1 | 3/2008 |
| WO | 2008051907 | A1 | 5/2008 |
| WO | 2008066569 | A2 | 6/2008 |
| WO | 2009006602 | A1 | 1/2009 |
| WO | 2009006608 | A1 | 1/2009 |
| WO | 2009006610 | A1 | 1/2009 |
| WO | 2009006615 | A1 | 1/2009 |
| WO | 2009025648 | A1 | 2/2009 |
| WO | 2009039174 | A1 | 3/2009 |
| WO | 2009111255 | A1 | 9/2009 |
| WO | 2009131879 | A1 | 10/2009 |
| WO | 2011060359 | A2 | 11/2009 |
| WO | 2009146089 | A2 | 12/2009 |
| WO | 2009146090 | A1 | 12/2009 |
| WO | 2009149462 | A2 | 12/2009 |
| WO | 2010011612 | A1 | 1/2010 |
| WO | 2010088279 | A2 | 8/2010 |
| WO | 2010117356 | A1 | 10/2010 |
| WO | 2010117597 | A1 | 10/2010 |
| WO | 2011011104 | A1 | 1/2011 |
| WO | 2012015954 | A1 | 2/2012 |
| WO | 2012015955 | A1 | 2/2012 |
| WO | 2012019191 | A2 | 2/2012 |
| WO | 2012090206 | A2 | 7/2012 |
| WO | 2012140147 | A3 | 10/2012 |
| WO | 2012145187 | A1 | 10/2012 |
| WO | 2012149008 | A2 | 11/2012 |
| WO | 2013003754 | A1 | 1/2013 |
| WO | 2013142387 | A1 | 9/2013 |
| WO | 2013163605 | A1 | 10/2013 |
| WO | 2014006471 | A2 | 1/2014 |
| WO | 2014012670 | A1 | 1/2014 |
| WO | 2014047528 | A1 | 3/2014 |
| WO | 2014054045 | A1 | 4/2014 |
| WO | 2014070316 | A1 | 5/2014 |
| WO | 2014076620 | A2 | 5/2014 |
| WO | 2014081958 | A1 | 5/2014 |
| WO | 2014145531 | A1 | 9/2014 |
| WO | 2014145712 | A1 | 9/2014 |
| WO | 2014162181 | A2 | 10/2014 |
| WO | 2014170771 | A1 | 10/2014 |
| WO | 2014179739 | A1 | 11/2014 |
| WO | 2014197101 | A1 | 12/2014 |
| WO | 2015074018 | A1 | 5/2015 |
| WO | 2015109028 | A1 | 7/2015 |
| WO | 2015157712 | A2 | 10/2015 |
| WO | 2016011309 | A2 | 1/2016 |
| WO | 2016025430 | A1 | 2/2016 |
| WO | 2016039761 | A1 | 3/2016 |
| WO | 2016131020 | A1 | 8/2016 |
| WO | 2016156446 | A1 | 10/2016 |
| WO | 2016178196 | A2 | 11/2016 |
| WO | 2016178197 | A1 | 11/2016 |
| WO | 2017024051 | A1 | 2/2017 |
| WO | 2017143198 | A1 | 8/2017 |
| WO | 2017198867 | A1 | 11/2017 |
| WO | 2017200956 | A1 | 11/2017 |
| WO | 2017222964 | A1 | 12/2017 |
| WO | 2018013725 | A1 | 1/2018 |
| WO | 2018031714 | A1 | 2/2018 |
| WO | 2018081314 | A1 | 5/2018 |
| WO | 2018102435 | A1 | 6/2018 |
| WO | 2018146690 | A1 | 8/2018 |
| WO | 2018150314 | A1 | 8/2018 |
| WO | 2018156930 | A1 | 8/2018 |
| WO | 2018187582 | A1 | 10/2018 |
| WO | 2018220143 | A1 | 12/2018 |
| WO | 2018220146 | A1 | 12/2018 |
| WO | 2019050831 | A1 | 3/2019 |
| WO | 2019051007 | A1 | 3/2019 |
| WO | 2019051108 | A1 | 3/2019 |
| WO | 2019051007 | A8 | 4/2019 |
| WO | 2019063521 | A1 | 4/2019 |
| WO | 2019079364 | A1 | 4/2019 |
| WO | 2019101855 | A1 | 5/2019 |
| WO | 2019232213 | A1 | 12/2019 |
| WO | 2020023839 | A1 | 1/2020 |
| WO | 2020121221 | A1 | 6/2020 |
| WO | 2020131247 | A1 | 6/2020 |
| WO | 2020132460 | A1 | 6/2020 |
| WO | 2020132668 | A2 | 6/2020 |
| WO | 2020132669 | A1 | 6/2020 |
| WO | 2020132670 | A1 | 6/2020 |
| WO | 2020132671 | A1 | 6/2020 |
| WO | 2020132678 | A1 | 6/2020 |
| WO | 2020144075 | A1 | 7/2020 |
| WO | 2020153765 | A2 | 7/2020 |
| WO | 2021094980 | A1 | 5/2021 |
| WO | 2021217055 | A1 | 10/2021 |
| WO | 2021236756 | A1 | 11/2021 |
| WO | 2022055920 | A1 | 3/2022 |
| WO | 2022167382 | A1 | 8/2022 |
| WO | 2023170632 | A1 | 9/2023 |

OTHER PUBLICATIONS

International Search Report and Written Opinion dated Feb. 18, 2021, in connection with PCT/IB2020/060669, filed Nov. 12, 2020.

International Search Report and Written Opinion dated Sep. 5, 2023, in connection with PCT/IB2023/055245, filed on May 22, 2023.

Wang et al., "Internal jugular vein ultrasound for the diagnosis of hypovolemia and hypervolemia in acutely ill adults; a systematic review and meta-analysis"; Internal and Emergency Medicine (2022) 17:1521-1532, Feb. 27, 2022.

Nippa et al., "Pulse wave velocity in human veins"; Journal of Applied Physiology, vol. 30, No. 4, Apr. 1971.

Rudski et al, Guidelines for the Echocardiographic Assessment of the Right Heart in Adults: A Report from the American Society of Echocardiography (J Am Soc Echocard 2010, 23: 685-713).

Stergiopulos et al. "Simple and accurate way for estimating total and segmental arterial compliance: The pulse pressure method" Ann Biomed Eng 22, 392-397 (1994).

Lee et al, "Prognostic significance of dilated inferior vena cava in advanced decompensated heart failure" International Journal of Cardiovascular Imaging (2014) 30:1289-1295.

Sonoo T, et al., "Prospective analysis of cardiac collapsibility of inferior vena cava using ultrasonography", J Crit Care 2015, http://dx.doi.org/10.1016/j.jcrc.2015.04.124.

Marik, et al., Does Central Venous Pressure Predict Fluid Responsiveness?*: A Systematic Review of the Literature and the Tale of Seven Mares, Chest (2008) 134(1):172-178.

Blehar, et al, Inferior vena cava displacement during respirophasic ultrasound imaging, Critical Ultrasound Journal (2012) 4:18.

Huguet et al., Three-Dimensional Inferior Vena Cava for Assessing Central Venous Pressure in Patients with Cardiogenic Shock, J Am Soc Echocardiogr. 2018; 31: 1034-43 (https://doi.org/10.1016/ j.echo.2018.04.003).

Katzarski et al. "A Critical Evaluation of Ultrasound Measurement of Inferior Vena Cava Diameter in Assessing Dry Weight in Normotensive and Hypertensive Hemodialysis Patients," AJKD, vol. 30, No. 4, Oct. 1997, pp. 459-465.

Hellevik et al. Heart Vessels v13, No. 4, p. 175-180, Jul. 1998.

Minten et al. Cardiovasc. Res, vol. 17, No. 10, pp. 627-632, Oct. 1983.

Dehkordi et al., Extracting Instantaneous Respiratory Rate From Multiple Photoplethysmogram Respiratory-Induced Variations; Frontiers in Physiology, vol. 9,Article 948; Jul. 18, 2018 (DOI: 10.3389/fphys.2018.00948).

Yates PhD dissertation, Stanford CA, SUDAAR 393 1969.

Miles et al "Peripheral Intravenous Volume Analysis (PIVA) for Quantitating Volume Overload in Patients Hospitalized With Acute Decompensated Heart Failure—A Pilot Study"; Journal of Cardiac Failure; 2018; https://doi.org/10.1016/j.cardfail.2018.05.003.

Reymond et al., Validation of a one-dimensional model of the systemic arterial tree Proceedings of the ASME 2009 Summer Bioengineering Conference (SBC2009); SBC2009-206424.

(56) References Cited

OTHER PUBLICATIONS

Peters et al.; Inductance calculation of planar multi-layer and multi-wire coils: An analytical approach, Sensors and Actuators A, 145-146, p. 394-404 (Year: 2007).
International Search Report and Written Opinion dated Nov. 4, 2019, in connection with PCT/US2019/034657, filed May 30, 2019.
International Search Report and Written Opinion dated Feb. 27, 2020, in connection with PCT/IB2019/060669 filed Dec. 11, 2019.
International Search Report and Written Opinion dated Mar. 3, 2020, in connection with PCT/US2019/066589 filed Dec. 16, 2019.
Extended European Search Report dated Jul. 3, 2020, in connection with EP20163433.4.
Horizon Scanning Research & Intelligence Centre; Furosemide sc2Wear micro-pump patch for oedema in heart failure; National Institute for Health Research; NIHR HSRIC ID: 11808; Mar. 2016; pp. 1-10; www.hsric.nihr.ac.uk.
ISR Report and Written Opinion dated Dec. 30, 2020, in connection with PCT/EP2020/067713 filed on Jun. 24, 2020.
Karami et al., "Semi-Automatic Algorithms for Estimation and Tracking of AP-Diameter of the IVC in Ultrasound Images," (Jan. 9, 2019) J. Imaging 2019, 5(1), 12 (Year 2019).
International Search Report and Written Opinion dated Oct. 19, 2017, in connection with PCT/US2017/046204.
Brennan, J.M., "Handcarried Ultrasound Measurement of the Inferior Vena Cava for Assessment of Intravascular Volume Status in the Outpatient Hemodialysis Clinic"; Clinical Journal of the American Society of Nephrology; pp. 749-753; Jan. 23, 2006.
International Search Report and Written Opinion dated Oct. 20, 2016, in connection with PCT/US2016/045385 filed Aug. 3, 2016.
Voroneanu et. al., "The relationship between chronic volume overload 3 and elevated blood pressure in hemodialysis patients: 4 use of bioimpedance provides a different perspective 5 from echocardiography and biomarker methodologies," Int Urol Nephrol, Sep. 2010, 42(3):789-97.
Cannesson et al., "Respiratory Variations in Pulse Oximetry Plethysmographic Waveform Amplitude to Predict Fluid Responsiveness in the Operating Room," Anesthesiology 2007; 106:1105-11.
Abraham et al., "The Role of Implantable Hemodynamic Monitors to Manage Heart Failure," Heart Failure Clin 11 (2015) 183-189.
Tallaj et al., "Implantable Hemodynamic Monitors," Cardiol Clin 29 (2011) 289-299.
Tang et al., "Measuring impedance in congestive heart failure: Current options and clinical applications," American Heart Journal 157 (3) 402-411.
Merchant et al., "Implantable Sensors for Heart Failure," Circulation: Arrhythmia and Electrophysiology. 2010; 3: 657-667.
Unadkat, Jignesh V., et al. "The Development of a Wireless Implantable Blood Flow Monitor," Ideas and Innovations, American Society of Plastic Surgeons, 136:199 (2015).
Steinhouse, David et al., "Implant Experience with an Implantable Hemodynamic Monitor for the Management of Symptomatic Heart Failure," PACE (Aug. 2005) vol. 28, pp. 747-753.
Braunschweig, Frieder et al. "Dynamic changes in right ventricular pressures during haemodialysis recorded with an Implantable haemodynamic monitor," Nephrol Dial Transplant (2006) 21:176-183.
Karamanoglu, Mustafa et al., "Estimation of cardiac output in patients with congestive heart failure by analysis of right ventricular pressure waveforms," BioMedical Engineering OnLine 2011, 10:36.
Spiliopoulos, Sotirios et la., "Beneficial aspects of real time flow measurements for the management of acute right ventricular heart failure following continuous flow ventricular assist device implantation," Journal of Cardiothoracic Surgery (2012) 7:119.
Sharma, Arjun D. et al., "Right Ventricular Pressure During Ventricular Arrhythmias in Humans: Potential Implications for Implantable Antitachycardia Devices," JACC vol. 15, No. 3, Mar. 1, 1990, pp. 648-655.
Kjellstrom, Barbo et al., "Changes in Right Ventricular Pressures Between Hemodialysis Sessions Recorded by an Implantable Hemodynamic Monitor," The American Journal of Cardiology, 2009, 103:119-123.
Zile, Michael R. et al., "Transition From Chronic Compensated to Acute Decompensated Heart Failure," Circulation, American Heart Association (2008) 118:1433-1441.
Plicchi, G. et al., "Pea I and Pea II Based Implantable Haemodynamic Monitor: Pre Clinical Studies in Sheep," Europace (2002) 4, 49-54.
Vanderheyden, Marc et al., "Continuous Monitoring of Intrathoracic Impedance and Right Ventricular Pressures in Patients With Heart Failure," Circulation Heart Failure (2010) 3:370-377.
Jacobs, Donald L. et al., "Bedside vena cava filter placement with intravascular ultrasound: A simple, accurate, single venous access method," Technical Note, Journal of Vascular Surgery, vol. 46, No. 6, pp. 1284-1286, Dec. 2007.
Muller, Laurent et al., "Respiratory variations of inferior vena cava diameter to predict fluid responsiveness in spontaneously breathing patients with acute circulatory failure: need for a cautious use," Critical Care 2012, 16:R188.
Blehar, David J. et al., "Identification of congestive heart failure via respiratory variation of inferior vena cava diameter." American Journal of Emergency Medicine (2009) 27, 71-75.
Miller, Joseph B., et al., "Inferior vena cava assessment in the bedside diagnosis of acute heart failure," American Journal of Emergency Medicine (2012) 30, 778-783.
Corl, Keith et al., "Bedside sonographic measurement of the inferior vena cava caval index is a poor predictor of fluid responsiveness in emergency department patients," Emergency Medicine Australasia (2012) 24, 534-539.
Feissel, et al. "The respiratory variation in inferior vena cava diameter as a guide to fluid therapy," Intensive Care Med (2004) 30: 1834-1837.
Nakao, Shoichiro et al., "Effects of Positional Changes on Inferior Vena Caval Size and Dynamics and Correlations with Right-Sided Cardiac Pressure," American Journal of Cardiology (1987; 59:125-132).
Saha, Narayan M., et al., "Outpatient Use of Focused Cardiac Ultrasound to Assess the Inferior Vena Cava in Patients With Heart Failure," American Journal of Cardiology (2015).
Ishizaki, et al. "Measurement of inferior vena cava diameter for evaluation of venous return in subjects on day 10 of a bed-rest experiment," J Appl Physical 96: 2179-2186, 2004.
Carbone et al. "Inferior Vena Cava Parameters Predict Re-admission in Ischaemic Heart Failure", European Journal of Clinical Investigations, 2014, 44(4): 341-349.
Bertram, C.D. et al., "Cross-sectional area measurement in collapsed tubes using the transformer principle", Med. & Biol, Eng. & Comput, 1989, 27, 357-364.
Moreno, Augusto et al., "Mechanics of Distension of Dog Veins and Other Very Thin-Walled Tubular Structures", Circulation Research, vol. XXVII, Dec. 1970, pp. 1069-1080.
Tafur, Emilio et al., "Simultaneous Pressure, Flow and Diameter of the Vena Cava with Fright and Exercise", Circulation Research, vol. XIX, Jul. 1966., pp. 42-50.
Guntheroth, Warren G., et al., "Effect of Respiration on Venous Return and Stroke vol. in Cardiac Tamponade", Circulation Research, vol. XX, Apr. 1967, pp. 381-390.
Bartels, Lambertus et al., "Improved Lumen Visualization in Metallic Vascular Implants by Reducing RF Artifacts", Magnetic Resonance in Medicine 47:171-180 (2002).
Guntheroth, Warren G., "in Vivo Measurement of Dimensions of Veins with Implications Regarding Control of Venous Return", IEEE Transactions on Bio-Medical Engineering, Oct. 1969; pp. 247-253.
Kivelitz, Dietmar et al., "A Vascular Stent as an Active Component for Locally Enhanced Magnetic Resonance Imaging", Investigative Radiology, vol. 38, No. 3, 147-152 (2003).
Reddy, Reddy R.V., et al., "A Catheter-Tip Probe for Dynamic Cross-Section Area Measurement", pp. 149-158. (1973).
Stegall, H. Fred, "Survey of Dimension Transducers", Chronically Implanted Cardiovascular Instrumentation, pp. 107-115 (1973).

(56) References Cited

OTHER PUBLICATIONS

D. H. Bergel, "The Measurement of Lengths and Dimensions", Cardiovascular Fluid Dynamics, vol. 1. pp. 91-114 (1972).
Baan, Jan et al., "Dynamic Local Distensibility of Living Arteries and its relation to Wave Transmission", Biophysical Journal, vol. 14, (1974); pp. 343-362.
International Search Report and Written Opinion in connection with PCT/US2016/017902, dated Jul. 27, 2016.
Reems, Miryam et al., Central Venous Pressure: Principles, Measurement, and Interpretation, Vetlearn.com, Jan. 2012, Compendium: Continuing Education for Veterinarians, pp. E1-E10.
Yamauchi, Hideko et al., "Correlation Between Blood Volume and Pulmonary Artery Catheter Measurements", Department of Surgery and Surgical Critical Care, University of Hawaii, 2005.
Abraham, William T. et al., "Wireless pulmonary artery haemodynamic monitoring in chronic heart failure: a randomised controlled trial"; www.thelancet.com, vol. 377, Feb. 19, 2011, pp. 658-666.
Guiotto, Giovanna et al., "Inferior vena cava collapsibility to guide fluid removal in slow continuous ultrafiltration: a pilot study", Intensive Care Med (2010) 36:696-696.
Martens, Pieter et al., "Current Approach to Decongestive Therapy in Acute Heart Failure", Curr Heart Fail Rep (2015) 12:367-378.
Dupont, Matthias et a., "Impact of Systemic Venous Congestion in Heart Failure", Curr Heart Fail Rep (2011) 8:233-241.
Marik, Paul E. et al., "Hemodynamic parameters to guide fluid therapy", Annals of Intensive Care 2011, 1:1; http://www.annalsofintensivecare.com/content/1/1/1.
Silverberg, Donald et al., "The association between congestive heart failure and chronic renal disease", Curr Opin Nephrol Hypertens 13: 163-170, 2004.
International Search Report and Written Opinion dated Mar. 27, 2018, in connection with PCT/US2017/063749.
International Search Report and Written Opinion dated Aug. 29, 2018, in connection with PCT/EP2018/064386.
International Search Report and Written Opinion dated Aug. 21, 2018, in connection with PCT/EP2018/064383.
Tchernodrinski et al., "Inferior vena cava diameter change after intravenous furosemide in patients diagnosed with acute decompensated heart failure: Inferior Vena Cava Diameter after Furosemide", Journal of Clinical Ultrasound, Vo. 43, No. 3, Jun. 4, 2014; pp. 187-193; XP093329764, US ISSN: 0091-2751, DOI: 10.1002/jcu.22173.
Tuplin et al, "Influence of the Respiratory Cycle on Caudal Vena Cava Diameter Measured by Sonography in Healthy Foals: A Pilot Study", Journal of Veterminary Internal Medicine, vol. 31, No. 5, Aug. 1, 2017; pp. 1556-1562, XP093329771, US ISSN: 0891-6640, DOI: 10.111/jvim.14793.

* cited by examiner

CLOSED-LOOP CONTROL OF HEART FAILURE INTERVENTIONAL THERAPY

RELATED APPLICATION DATA

This application is a continuation of U.S. Nonprovisional patent application Ser. No. 17/162,857, filed on Jan. 29, 2021, and titled "Patient Self-Monitoring of IVC Volume for Early Heart Failure Warning Signs", which application is a continuation of U.S. Nonprovisional patent application Ser. No. 15/549,042, filed on Aug. 4, 2017, and titled "Implantable Devices and Related Methods for Heart Failure Monitoring" (now U.S. patent Ser. No. 10/905,393, granted Feb. 2, 2021), which application is a U.S. national phase of International Patent Application No. PCT/US16/17902, filed on Feb. 12, 2016, and titled "Implantable Devices and Related Methods For Heart Failure Monitoring." International Patent Application No. PCT/US16/17902 claims the benefit of priority of U.S. Provisional Patent Application No. 62/172,516, filed Jun. 8, 2015, and titled "Methods and Apparatus for Monitoring Patient Physiological Status Based On Inferior Vena Cava Volume," claims the benefit of priority of U.S. Provisional Patent Application Ser. No. 62/157,331, filed May 5, 2015, and titled "Heart Failure Monitoring System and Method," and also claims the benefit of priority of U.S. Provisional Patent Application Ser. No. 62/115,435, filed Feb. 12, 2015, and titled "Implantable Device and Related Methods for Heart Failure Monitoring." Each of these applications is incorporated by reference herein in their entirety.

FIELD OF THE INVENTION

The present invention generally relates to the field of medical devices and methods for monitoring heart health. In particular, the present invention is directed to methods for patient self-monitoring of IVC volume for detecting early warning signs of acutely decompensated heart failure.

BACKGROUND

Heart failure is one of the most significant chronic conditions afflicting adult populations. In the United States, 5.7 million Americans have heart failure, with 870,000 new cases annually. As the population ages, this population is growing, as approximately 10% of the population over 80 suffers from heart failure. It is estimated that by 2030 8 million Americans will have heart failure. The costs of caring for heart failure are over thirty billion dollars per year. Twenty billion of this cost is direct medical costs. This expense is expected to more than double over the next fifteen years.

In patients with chronic heart failure, a significant portion of these costs is due to hospitalization to manage acutely decompensated heart failure (ADHF). Each re-hospitalization can last up to a week, and costs approximately $10,000. ADHF is very often a result of some combination of a downturn in the heart's performance and excessive intake of fluids and/or salt. This leads to a buildup of fluid in the vascular system. Increased blood volume in the left atrium at higher pressure means higher blood pressure in the lungs, which eventually leads to fluid filling the lungs and an inability to breathe. At this stage it is imperative to hospitalize the patient to carefully manage them while drugs are delivered to remove the excess fluids.

Managing these patients to prevent the need for rehospitalization is extremely challenging. Many non-invasive approaches to monitoring patients have been tried, such as weighing patients daily to detect fluid weight gain, having a nurse call them daily to assess their health status, and so on. More recently, various implantable monitoring devices have been tested. One example is the "CardioMEMS" device of St. Jude Medical, Inc., which is a wireless pressure monitor implanted in the pulmonary artery (PA). An external power supply and receiver is placed on the patient's chest to charge the implanted sensor and receive pressure data measured by it. Other companies are developing their own versions of such PA pressure monitors. The money saved by avoiding re-hospitalization can more than pay for the cost of such devices.

It is important to measure the onset of ADHF early enough to give the patient and/or caregiver enough time to adjust their behavior, medication, or other factors to prevent the patient from ending up with frank congestion and the need for hospitalization. FIG. 47, adapted from the CardioMEMS website, shows the timeline of physiologic changes leading up to ADHF requiring hospitalization. There is clinical evidence that IVC volume variation changes occur up to several weeks prior to decompensation.

In addition to heart failure patients, hemodialysis patients have a chronic need for careful volume management. Large volumes of fluid are involved in the hemodialysis process, and managing patients so that they don't end up hypovolemic or overloaded with fluid requires careful management. A monitor which provided immediate feedback on these patient's volume status before, during and after hemodialysis would be very helpful.

There are other groups of patients who might benefit from such a monitor. For example, patients in septic shock or occult shock due to trauma are subject to hypoperfusion which can be identified by measuring the degree of collapse of the IVC. While it may or may not make sense to implant a device permanently to manage these acute events, if the patient has recurrent episodes of these events or already has such a monitor implanted for other reasons, the IVC monitor may be helpful in managing these patients.

Congestive heart failure is so-named because additional blood volume backing up into the lungs causes fluid to seep out of the pulmonary circulation into the airway passages of the lungs, causing congestion of the lungs. The patients become short of breath, and typically need to be hospitalized and carefully managed while the excess fluid is removed by a combination of fluid management and aggressive use of diuretic medications.

This happens because the left ventricle is not able to pump all of the volume of blood returning to the heart from the lungs. Although measurement of left atrial pressure, typically by measuring pulmonary artery wedge pressure, is commonly considered the most direct way to measure congestion in heart failure, there are other areas where congestion can be detected. When additional blood volume is added to the circulatory system, the IVC is one of the first places for that added volume to collect. To quote a paper, "In patients with advanced heart failure, left ventricular systolic dysfunction causes increased left atrial pressure. The pressure is transmitted back through the pulmonary circulation to cause pulmonary artery hypertension. The pulmonary artery hypertension can worsen pre-existing right ventricular dysfunction and exacerbate tricuspid valve regurgitation, leading to systemic venous congestion. If venous congestion and elevated central venous pressure are the hallmarks of heart failure, then distention of the inferior vena cava [measured by echocardiography] may be a good prognostic marker in patients with decompensated heart failure." (Lee et al, "Prognostic significance of dilated inferior vena cava in advanced decompensated heart failure," International Journal of Cardiovascular Imaging (2014) 30:1289-1295).

The diameter of the IVC has also demonstrated correlation with right atrial pressure, and it may correlate with renal function and renal sodium retention, which are also very important prognostic factors of heart failure. Therefore, increasing IVC volume and/or pressure may be a very effective early indicator of worsening heart failure condition.

However, recent studies have indicated that the variation in IVC volume over the respiratory cycle is a more sensitive measurement of fluid overload and/or heart failure than simple measurement of average IVC volume, diameter, or pressure. During inspiration, intrathoracic pressure decreases, thereby increasing venous return and causing collapse of the IVC. During expiration, intrathoracic pressure increases, decreasing venous return and causing an increase in the volume of the IVC.

Since the IVC typically collapses in the anterior-posterior direction, some studies have suggested that the most accurate technique for measuring IVC volume changes with ultrasound is to measure the distance from the anterior wall of the IVC to the posterior wall.

In applying this measurement to heart failure, at least one study has suggested that a variation of less than 15% (measured as maximum anterior-posterior dimension minus minimum A-P dimension, divided by the maximum A-P dimension) is indicative of impending or present ADHF.

While vessel dimensions may be measurable using external ultrasound, magnetic resonance imaging, computerized axial tomography, or other technologies, these imaging procedures must be administered in a hospital or other specialized facility, do not permit continuous monitoring, and do not allow for monitoring of the patient at their home or other remote location. As a result, the condition of a heart failure patient can worsen into a critical state before care providers become aware of it, dramatically increasing the mortality risk and cost of treatment for the patient.

Prior studies of IVC dimensions without implantable devices have been conducted using ultrasound imaging. This typically requires a highly trained physician or ultrasound technician to manage the ultrasound machine, ensure an appropriate connection of the transducer to the skin, position the ultrasound transducer in the appropriate location, identify the IVC, and take accurate measurements. This is not something that heart failure patients or their caregivers could typically be trained to do predictably and accurately with existing equipment. Moreover, these systems typically include large, complex, and expensive pieces of equipment which are not suitable for use outside of a specialized medical facility.

As is understood in the art, there is a long history of implantable vena cava filters to catch clots which embolize from the leg veins, catching them and holding them in the vena cava until they dissolve in the blood flowing past. The widespread clinical use of such IVC filters demonstrates the safety and feasibility of anchoring an implant in the IVC and provides useful teachings as to how aggressively IVC anchors may be shaped, how much radial force a device should exert, how strong the elements should be, etc. However, in spite of the widespread use of IVC filters over many years, heretofore it has not been suggested that an implant in the IVC could be utilized for purposes of monitoring fluid volume or IVC dimensions. Moreover, even if a suggestion were made to equip an IVC filter with a sensor for monitoring vascular dimensions, such filters would be unsuited to the purpose. The anchoring structures used to secure IVC filters constrain the vessel from natural size and shape changes in response to changes in fluid volume and would thus limit the usefulness or accuracy of such a device.

SUMMARY OF DISCLOSURE

Embodiments disclosed herein include an implantable device for monitoring vascular lumen diameter, comprising means for detecting lumen diameter at a monitoring location; an anchor element configured to securely anchor the device to the vascular lumen at an anchoring location with the detecting means positioned at the monitoring location; and an anchor isolation structure extending between the detecting means and anchor element, the anchor isolation structure having a shape and length specifically configured to substantially isolate the detecting means at the sensing location from distortions of the vessel caused by the anchoring element at the anchoring location.

In one implementation, the present disclosure is directed to a heart failure interventional method with closed-loop control. The method includes continuously or intermittently receiving from a patient-implanted vascular sensor a signal indicative of a cardiac health status parameter; and automatedly modulating a therapy delivered by a therapeutic device continuously or intermittently in response to the received signal indicative of the cardiac health status parameter.

In another implementation, the present disclosure is directed to heart failure interventional method with closed-loop control based on real-time patient fluid status. The method includes implanting a wireless vascular lumen dimension sensor in a patient vena cava; wirelessly receiving from the vascular lumen dimension sensor implanted in the vena cava a continuous or intermittent signal indicative of a dimension or change in dimension of the vena cava, the intermittent signal occurring at programmed intervals; correlating the continuously or intermittently received signal from the vascular lumen dimension sensor to a continuous or intermittent patient fluid volume state as the signal is received; receiving the patient fluid volume state continuously or intermittently in a therapeutic device controller; and automatedly modulating a therapy delivered by a therapeutic device communicating with the therapeutic device controller continuously or intermittently in response to the received patient fluid volume state correlated from the vena cava lumen dimension sensor signal.

In yet another implementation, the present disclosure is directed to a heart failure interventional system with closed-loop control. The system includes a cardiac health status monitoring system comprising a wireless vascular implant and control unit, wherein the wireless vascular implant is configured to generate and wirelessly deliver a signal containing information indicative of a patient cardiac health status parameter to the control unit, the control unit being configured to process the signal to determine a value for the cardiac health status parameter continuously or at programed intervals; a therapeutic device including a processor configured to execute instructions to modulate therapeutic intervention continuously or at programed intervals based at least in part on the determined value for the patient cardiac health status parameter; and a communication link between the monitoring system and the therapeutic device.

In still yet another implementation, the present disclosure is directed to a heart failure interventional system with closed-loop control based on real-time patient fluid status. The system includes an inferior vena cava (IVC) fluid monitoring system comprising a wireless IVC implant configured to generate and wirelessly deliver to an external controller a signal indicative of a dimension or change in dimension of the IVC, the dimension or change in dimension being correlated to a patient fluid state by the external controller continuously or at programed intervals; one or more heart failure therapeutic devices controlled by one or more processors configured to execute instructions to modulate therapeutic intervention continuously or at programed intervals based on patient fluid state as determined by the IVC fluid monitoring system; and a communications link between the IVC fluid monitoring system and the one or more processors.

In another implementation, the present disclosure is directed to heart failure interventional system, which includes an implantable device for monitoring vascular lumen diameter, comprising: means for detecting lumen diameter at a monitoring location; an anchor element configured to securely anchor the device to the vascular lumen at an anchoring location with the detecting means positioned at the monitoring location; and an anchor isolation structure extending between the detecting means and anchor element, the anchor isolation structure having a shape and length specifically configured to substantially isolate the detecting means at the monitoring location from distortions of the vessel caused by the anchoring element at the anchoring location; an implantable cardiac therapy device including an implantable housing containing at least power and control modules; a communications link between the implantable monitoring device and the implantable cardiac therapy device; at least one cardiac therapy delivery element; and at least one lead connecting the at least one cardiac therapy delivery element to the implantable housing and modules contained therein; wherein the control module executes instructions for generating a signal with the detecting means, receiving a signal responsive to the generated signal with the detecting means, the received signal being indicative of vessel diameter at the monitoring location; determining lumen diameter at the monitoring location based on the signal; comparing the determined diameter to a reference diameter to determine a change in lumen diameter, evaluating heart condition based on the determined change in lumen diameter; and modulating cardiac therapy delivered by the implantable cardiac therapy device via the at least one cardiac therapy delivery element based on the evaluated heart condition.

BRIEF DESCRIPTION OF THE DRAWINGS

For the purpose of illustrating and exemplifying the claimed invention, the drawings show aspects of embodiments of the present disclosure. However, it should be understood that the claimed invention is not limited to the precise arrangements and instrumentalities of the exemplifying embodiments shown in the drawings, wherein:

DISCLOSURE OF EMBODIMENTS

Figure 1:
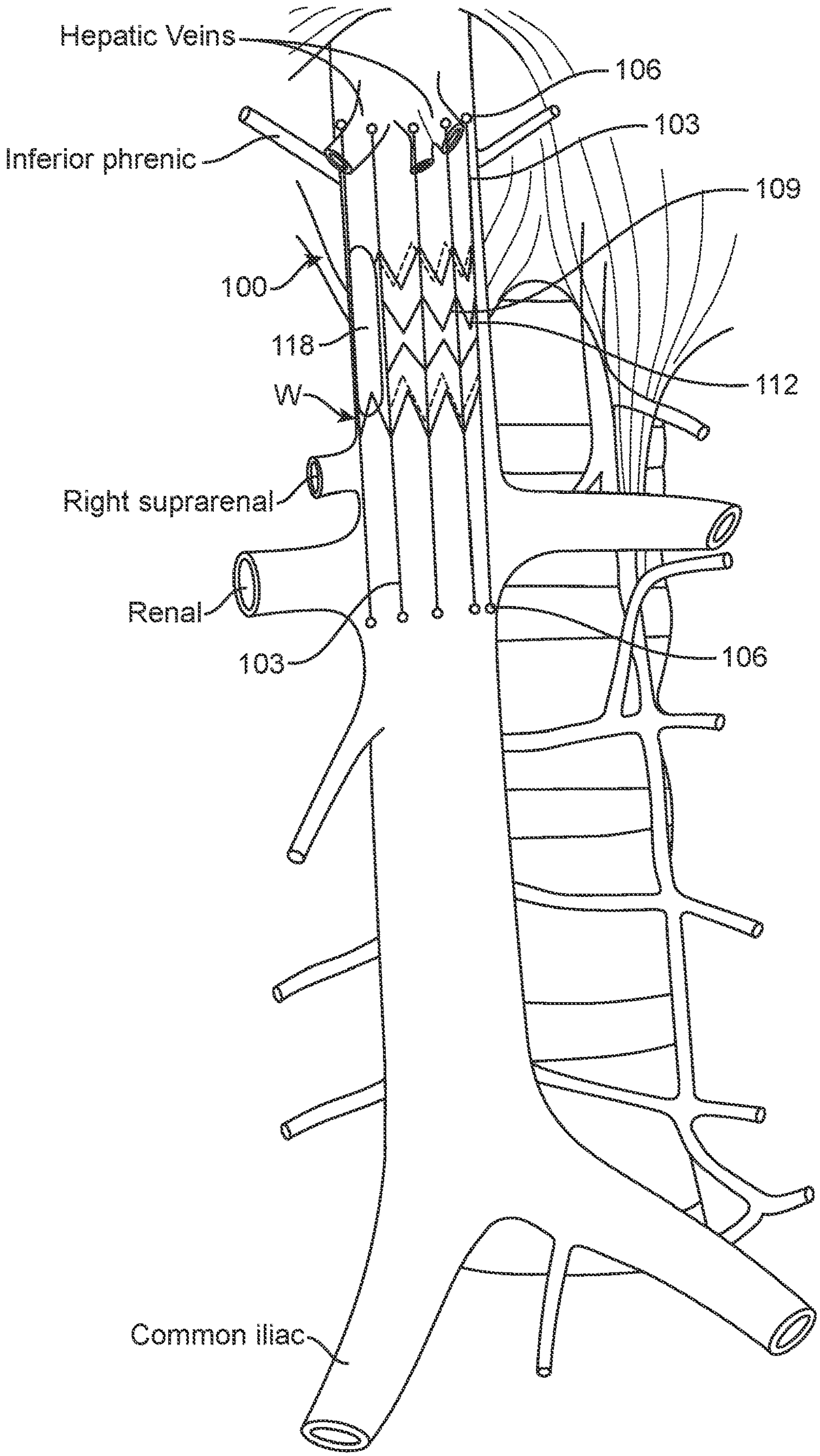
FIG. 1 is a schematic illustration of one embodiment of an implantable device deployed in the inferior vena cava (IVC) in accordance with the present disclosure.

Various embodiments disclosed herein are intended to monitor for and detect variations in volume and/or pressure of the inferior vena cava (IVC) as an early warning signal of the acute severity of heart failure. Implantable IVC monitors, markers and related systems, devices and methods as described herein may enable the patient and physician to take proactive steps in time to prevent acute decompensation requiring hospitalization. Such devices and methods also may be helpful in managing hemodialysis patients, in whom volume management is a chronic challenge. The present disclosure thus describes methods and devices for measuring IVC volume and/or pressure more or less continuously, depending on clinical need, using various forms of implantable devices.

In order to measure changes in IVC dimension or volume accurately, the devices of the invention must be configured to be secured at the desired location in or on the vessel without affecting the natural dilation and constriction of the vessel, or by affecting it in a way which is known and predictable so that it can be accounted for. In many of the embodiments disclosed herein, implantable monitoring devices include an anchoring member which secures the device to the vessel and immobilizes the device both longitudinally and rotationally, and a sensing or marking element which responds to vessel expansion and contraction to allow monitoring of changes in vessel dimension. It is critical in such embodiments that the anchoring element not distort the vessel dimensions being measured by the sensing/marking element. In preferred embodiments, the sensing or marking element is isolated from the anchoring member such that the vessel can naturally expand and contract at the site of measurement without significant constraint. In some embodiments, this isolation comprises a longitudinal separation of the sensing/marking element from the anchor member a distance sufficient to minimize the effects of the anchor on the vessel motion at the measurement site. In such embodiments the sensing/marking element will be coupled to the anchor member by an elongated connecting element which has a length and flexibility sufficient to provide the necessary isolation, which has sufficient rigidity to maintain the position of the sensing/marking element at the measurement site, and which, in many embodiments, has the appropriate shape and resilience to bias the sensing/marking element against the wall of the vessel as it moves inward and outward. Such connecting elements will also have a length selected to allow the anchor member to be implanted in the desired location in the IVC, in preferred embodiments just inferior to the hepatic veins, with the sensing/marking element positioned in the IVC between the anchor member and the right atrium. In certain exemplary embodiments, such connecting elements will have a length in the range of 1 to 4 times the vessel diameter (e.g. 1-8 cm), more desirably 1 to 3 times the vessel diameter (e.g. 2-6 cm), and preferably 1 to 2 times the vessel diameter (e.g. 2-4 cm). In some embodiments it will be desirable to provide a longitudinal separation between the anchor element and the marker elements of about 3-5 cm. Also, it may be desirable to position the anchor elements somewhat inferior to the renal arteries so that the marker elements fall between the renal and hepatic veins. In one preferred embodiment, the marker elements are positioned at a monitoring location falling in a region from approximately 2 cm below the hepatic veins down to, but not below the renal veins. In other embodiments, instead or in addition to spatial separation of the anchor and sensor/marker, isolation may be achieved by a mechanical coupling between the anchor and the sensing/marking element which mechanically isolates movement of the sensing/marking element from the anchor, such as a spring, hinge, flexible link, or other type of isolating coupling.

Because heart failure patients often receive catheters for monitoring and treatment which are inserted through the IVC, preferred embodiments of the invention will be configured to allow the placement of catheters and other devices past the location of the implanted monitoring device without risk of displacement or compromising its function. In some embodiments, the devices of the invention are configured to be anchored to the vessel wall without jailing (i.e. extending across) or substantially occluding the vessel lumen.

In certain embodiments described herein the monitoring devices of the invention are configured to measure vascular dimension in a predetermined direction or along a predetermined axis. Such embodiments are configured to facilitate implantation within the vessel in a position which enables such directional measurement. In exemplary embodiments, the devices of the invention are configured to measure IVC diameter in the anterior-posterior direction. In such embodiments the devices are configured to preferentially position and maintain the sensing or marking elements against the posterior and/or anterior wall of the IVC throughout the respiratory cycle. Exemplary embodiments may further include anchoring elements that deploy in such a way as to preferentially position the device in the desired rotational position in the vessel. For example, such anchoring elements may have a shape or include features which take advantage of the oval cross-sectional shape of the IVC and naturally seat themselves in the desired rotational orientation.

Figure 2A:
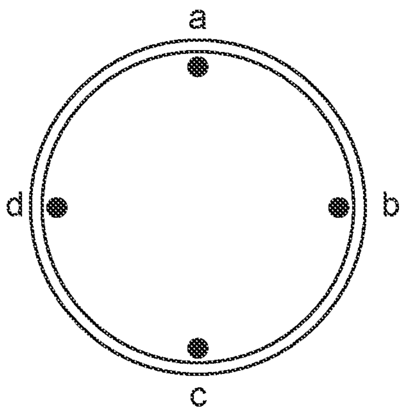
FIGS. 2A, 2B, 2C and 2D show schematic cross-sections of the IVC and relative electrode positioning in embodiments described in the present disclosure.
Figure 2B:
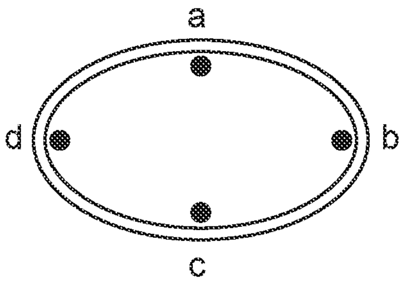
Figure 2C:
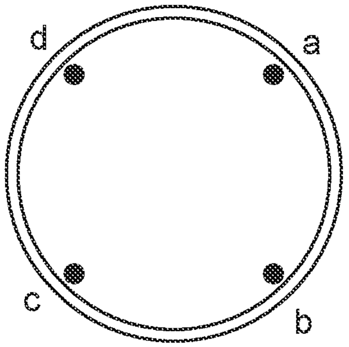
Figure 2D:
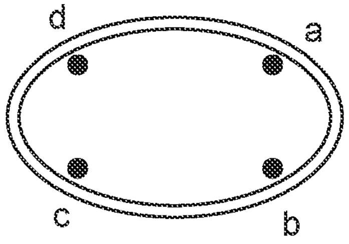

One type of device disclosed herein, as shown, for example, by the embodiment in FIG. 1, may have flexible marker elements, such as flexible electrodes, that lay unobtrusively against the wall of the IVC. Various embodiments of this type of device are described in more detail below. As the marker element positions change relative to one another based on changes in shape/volume of the IVC, the change may be determined through signals or feedback exchanged between the marker elements. For example, as the IVC decreases in volume, it may go from being fully inflated with a round shape to a flatter shape. In a design with a number of marker elements deployed circumferentially around a cross-section of the IVC, this means that certain marker elements may become closer together as the IVC collapses, and some may move farther apart. FIGS. 2A, 2B, 2C and 2D schematically illustrate how this change may occur. As is seen, the variation in proximity of the marker elements with IVC collapse depends upon the orientation of the device relative to the axis of collapse of the IVC. In FIGS. 2A and 2B, it is seen that marker elements a and c become closer as the IVC collapses, while marker elements b and d move farther apart. In FIGS. 2C and 2D, marker elements a and b and c and d become closer as the IVC collapses. Alternatively, a single marker element may be provided with a signal type that may be reflected off of the opposite IVC wall. The same principals apply when a single marker element is used with a signal reflected off the opposite IVC wall. In one such example, the single marker element may be positioned at location a in FIGS. 2A and 2B, with the reflected wall being generally at location c, directly across from a.

In general, marker elements used in embodiments disclosed herein may be active marker elements or passive elements. Examples of active marker elements include ultrasound transducers, electrodes and inductance coils. Passive marker elements are generally signal reflective, such as echo-reflective, which can reflect an ultrasound signal directed at the marker elements from outside the body. In an embodiment where the market elements are comprised of electrodes, it may be most effective to determine which electrodes are positioned most directly on the anterior and posterior walls, and to measure the variation in impedance between those electrodes. Alternatively, the system could measure the impedance from each electrode to each of the others, and to use the variation in impedances to estimate the change in shape. Or it may be equally effective to combine the impedances of all of the opposing electrode pairs in parallel, and look at the variation in that single overall impedance reading.

Figure 35:
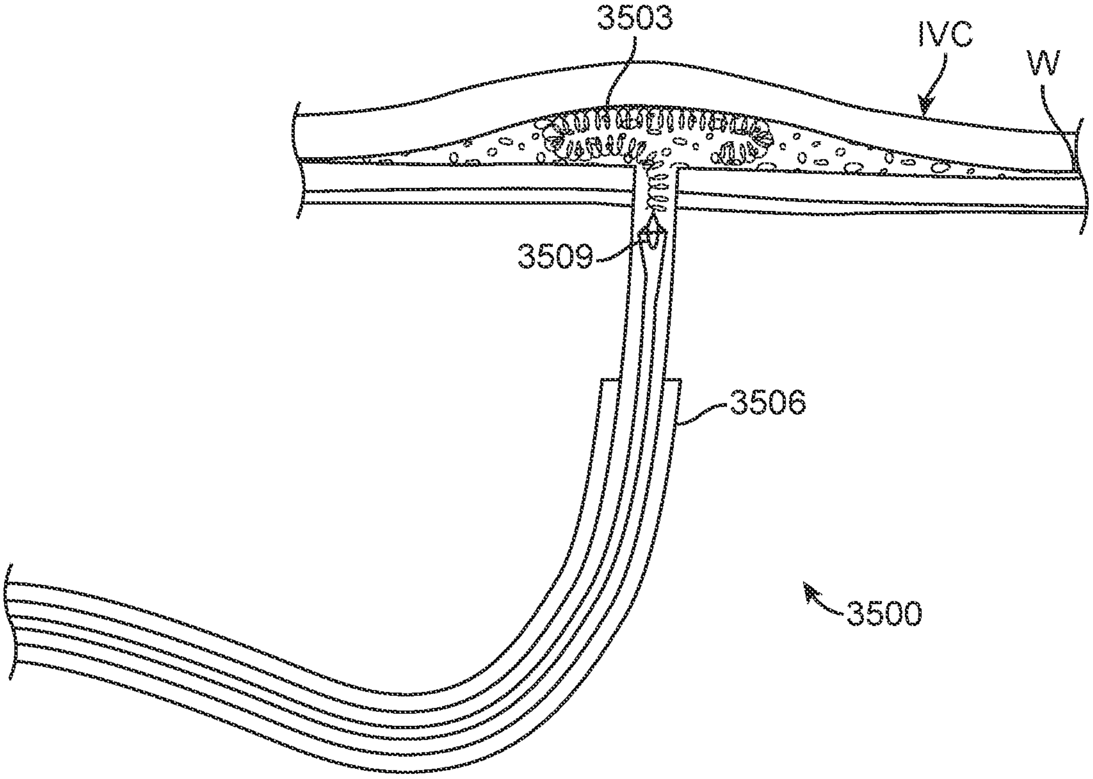
FIG. 35 illustrates another exemplary embodiment in which a marker is deployed through a delivery catheter that holds the marker between two jaws until it reaches the distal end of the delivery catheter, at which point the jaws separate to release the marker.

In certain situations it may alternatively or also be effective to measure the longitudinal impedance along the length of the IVC or the superior vena cava (SVC), or both. As the IVC and/or SVC collapses, the cross-sectional area of the IVC and SVC decreases, which may lead to a meaningful change in impedance along its length. One exemplary embodiment employing this alternative is illustrated in FIG. 35 as described below.

Figure 24:
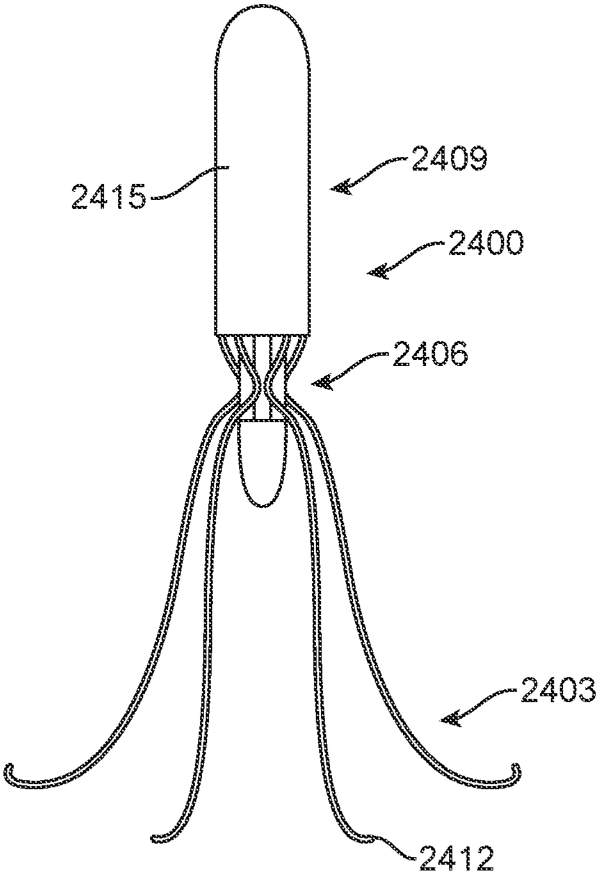
FIG. 24 is a schematic illustration of a further embodiment of implantable device according to the present disclosure.

In addition to simply measuring impedance across the IVC by use of implantable, flexible electrodes, there are a number of other ways by which an implantable device may measure the variation in shape of the IVC. Such further alternatives include elements such as strain gauges or displacement sensors attached to a radial or circumferential element of the device, proximity sensors, etc. One exemplary embodiment in this regard is illustrated in FIG. 24 as described below.

Fluid pressure sensors may also be useful in measuring variations in IVC status. Alternatively, the flow rate through the IVC might be measured using a Doppler ultrasound sensor or other sensor. As the volume and cross-sectional area of the IVC change, the speed of blood flow through the IVC might change inversely and proportionately, although blood volume and flow will also change with changes in posture, exercise level, and so on. In this approach, it might be helpful to measure heart rate as well as an indicator of cardiac output, to normalize flow rates or to make certain that measurements are only being taken when the patient is at rest. Inertial sensors might also be included, to measure posture and motion. MEMS inertial sensors have been developed which are tiny and consume very little battery power. It might also be helpful to implant a reference pressure sensor or inertial sensor elsewhere in the body or vascular system, such as in the leg, to detect posture changes and activity level.

A further alternative measurement means is to use sonomicrometry. This involves tiny piezoelectric crystal sensors which emit tiny sonic signals, which are then detected by other sensors and converted to an electrical signal. By analyzing the time between the transmission and reception of these signals, the distance between the crystals can be accurately measured. A further alternative measurement means is to transmit a sonic vibration into the IVC, and by measuring the reflection or resonance of that signal, the overall volume or dimensions of the IVC might be determined.

The choice between these different methods will depend in part on determining which ones measure the variation in IVC volume and pressure most consistently and precisely. Minimizing energy consumption is also an essential factor for implantable devices which are intended to function for years, unless external power sources are used to power or re-charge the device.

In alternative embodiments, one or more devices may be implanted on an external surface of the IVC to detect changes in vascular dimensions. For example, a single device having two spaced-apart electrodes, or two separate devices each with its own electrode, may be anchored to the outer IVC wall and used to measure impedance between the electrodes. Alternatively, a device having a strain gauge may be anchored to the outer wall to measure stress, strain, or displacement between two points on the wall. In another embodiment, a wire loop or band incorporating a force or displacement sensor may be placed around the IVC to detect changes in IVC circumference based upon the change in size or tension in the loop or band. Such devices may be miniaturized so as to be delivered using a large-bore needle or other low-profile delivery instrument that can be placed through a small puncture in the thoracic or abdominal wall and delivered to the desired location on the IVC.

This monitoring may be performed continuously or intermittently, depending upon the desired tradeoff between data intensity and battery life. It might be most efficient to take measurements only at night, when the patient is lying down and at rest. It might be desirable to intermittently measure IVC dimensions at random, or at specific time intervals. Although these intermittent measurements might result in measuring the IVC distention at random points in the cardiac and respiratory cycle, over a period of minutes, hours, or days an effective picture of the IVC variation may become clear. Alternatively, the device may intermittently take continuous measurements over one or more entire cardiac and/or respiratory cycles, to get an effective measurement of the maximum and minimum IVC volumes. The difference between those minimum and maximum volumes may be an important prognostic indicator. If there is only a small variation between minimum and maximum IVC volumes, that may be an indicator of congestion.

Exemplary embodiments shown in the figures will now be described in more detail to further illustrate various configurations and designs of the disclosure. As will be apparent to persons of ordinary skill in the art based on the teachings herein contained, different features of the various disclosed embodiments may be employed with embodiments other than those with which they are specifically shown in the drawings for purposes of illustration. Given the number of possible combinations, it is not possible within a concise disclosure to separately illustrate each combination of features as would be understood by those skilled in the art. As non-limiting examples, each of the different anchor elements shown in FIGS. 5-21, and the marker elements shown in FIGS. 1, 3-5, 22-30 may be used together in different combinations or individually with each different implant herein.

As shown in FIG. 1, monitoring device 100 may have several flexible, insulated arms 103 that lay passively against the wall W of the IVC. Marker elements 106 (referred to hereinafter generically as marker elements or by specific marker element type, such as electrode, coil or ultrasound element, etc.) may be mounted on arms 103, preferably at an end spaced from the body of device 100. In one exemplary embodiment, marker element 106 comprise electrodes 106 mounted on arms 103, and the impedance between the electrodes may be monitored via suitable monitoring devices and means as described further below. There may be as few as two, three, or four electrodes 106, or there may be many. There also may be more than two arms 103. If there are just two arms 103, they may generate the most effective measurements if positioned against the anterior and posterior walls of the IVC. Electrodes 106, or other marker element, may be arrayed circumferentially around the IVC at one specific cross-section, or there may be electrodes at two or more specific cross-sections, or they may be arranged over the length of the IVC. Impedances may be measured in a matrix between all of the different electrodes, or the system may focus on measuring impedances just between electrodes on opposing walls, to measure any collapse of the IVC most efficiently.

Alternatively, instead of measuring impedance between electrodes, marker elements 106 may comprise inductance coils that may be located at the ends of arms 103 of device 100 in FIG. 1. A small current could be delivered to one coil, and the induced current in the other coil could be measured to determine the distance between the coils.

A further alternative embodiment comprises positioning two ultrasound crystals as marker elements 106 on opposing arms 103 of device 100. An ultrasonic signal from one crystal could then be detected by the opposing crystal, and the diameter of the IVC could then be determined by measuring the time-of-travel between the two crystals. Alternatively, and as described further below, a single ultrasound crystal could be positioned on a single arm of the device with the crystal acting as both emitter and receiver of an ultrasound signal such that vessel diameter could be determined by reflecting a signal against the opposing wall of the vessel and measuring time of travel back and forth from the crystal.

Device 100 may be located entirely within the IVC as shown in FIG. 1. In this exemplary embodiment, device 100 is held in place by anchor element 109, comprising a radially expanding stent, which has hooks 112 that engage the IVC wall W. Multiple arms 103 extend superiorly along the IVC, and are biased gently outwards to hold themselves against the IVC wall W. At the end of arms 103 are marker elements 106, which may be electrodes as described above. Device 100 senses changes in impedance between the marker element electrodes to measure the degree of distention or collapse of the IVC. Alternatively or in addition, device 100 may also include arms 103 extending inferiorly, holding another set of marker elements 106 against the IVC wall W in a more inferior position, which can also be used to determine the variation in IVC size. Anchor element 109, such as the illustrated radially expanding stent, may be made gentle enough so as to not prevent the distention or collapse of the IVC. In that case, marker elements 106 (here illustrated as electrodes) may be mounted directly on the anchoring element itself. Various similar embodiments disclosed herein, may be important to encapsulate the structure and arms of the device in an electrically insulative material, so that it doesn't prevent the measurement of IVC cross-section via impedance measurements.

In a further alternative, anchor element 109 (such as, for example, the stent shown in FIG. 1 or in FIG. 23) and/or arms 103 may be made of a bioerodable material which softens over time, to minimize any effect the structure might have on the natural motion of the IVC. The structure of arms 103 (or anchor element 109) may also be designed to aggressively heal into the walls of the IVC, to minimize the risk of migration or embolization over time. Such alternatives may also be combined, for example, by making the anchor element or arms out of a bioerodable material such as poly-l-lactide (PLLA) and covering the struts of the device with a woven or braided polyester sleeve or open-cell expanded polytetrafluorethylene (ePTFE). As the struts erode over time, they will stimulate a somewhat inflammatory response which will encourage the fabric to heal into the wall, so that by the time the PLLA structure is gone, the device will be well-healed into the wall.

The IVC is large enough that a low-profile electronics control housing, such as capsule 118 in FIG. 1, can be located on an implantable device such as device 100 without meaningfully occluding blood flow through the IVC. Such an electronics capsule also may be configured and dimensioned to be entirely positioned against the walls of the IVC, so that the central channel of the IVC remains open and unimpeded for the introduction of any other catheter in the future. Electronics capsule 118 may have either a battery or inductive coil or both to power the device. Alternatively, or additionally, the device may be designed to harvest energy from local environmental sources by including, for example, a piezoelectric generator to produce power from the pulsation of the heart. In addition, the electronics capsule will have connections to the marker elements and a telemetry circuit to communicate information to a controller unit (not shown) outside the patient's body. Preferably the device includes a wireless transmitter to transmit sensor data to an external receiver and controller. The device may be configured to transmit continuously or at programmed intervals, or to transmit data upon interrogation by an external device. It may also have a memory circuit to store historical sensor measurements, and a calculation circuit to convert the various sensor measurements to an estimate of IVC distention or collapse. Additionally or alternatively, the device may be configured to communicate with a wireless-enabled cellular device such as a smartphone, which may include software to transmit data via cellular or wireless network to a remote computer. In this way, the measured IVC parameters may be automatically transmitted to healthcare providers to allow monitoring of the patient's condition. More details of related control and networking embodiments are discussed below.

Device 100, as illustrated in FIG. 1, is shown positioned largely superior to the renal veins within the IVC. However, implantable devices as disclosed herein also may be positioned partially or entirely inferior to the renal veins, or even within the right atrium or the superior vena cava (SVC). Alternatively the devices may have multiple components implantable in different locations, such as one component in the IVC, and a second component in the SVC or elsewhere.

Figure 3:
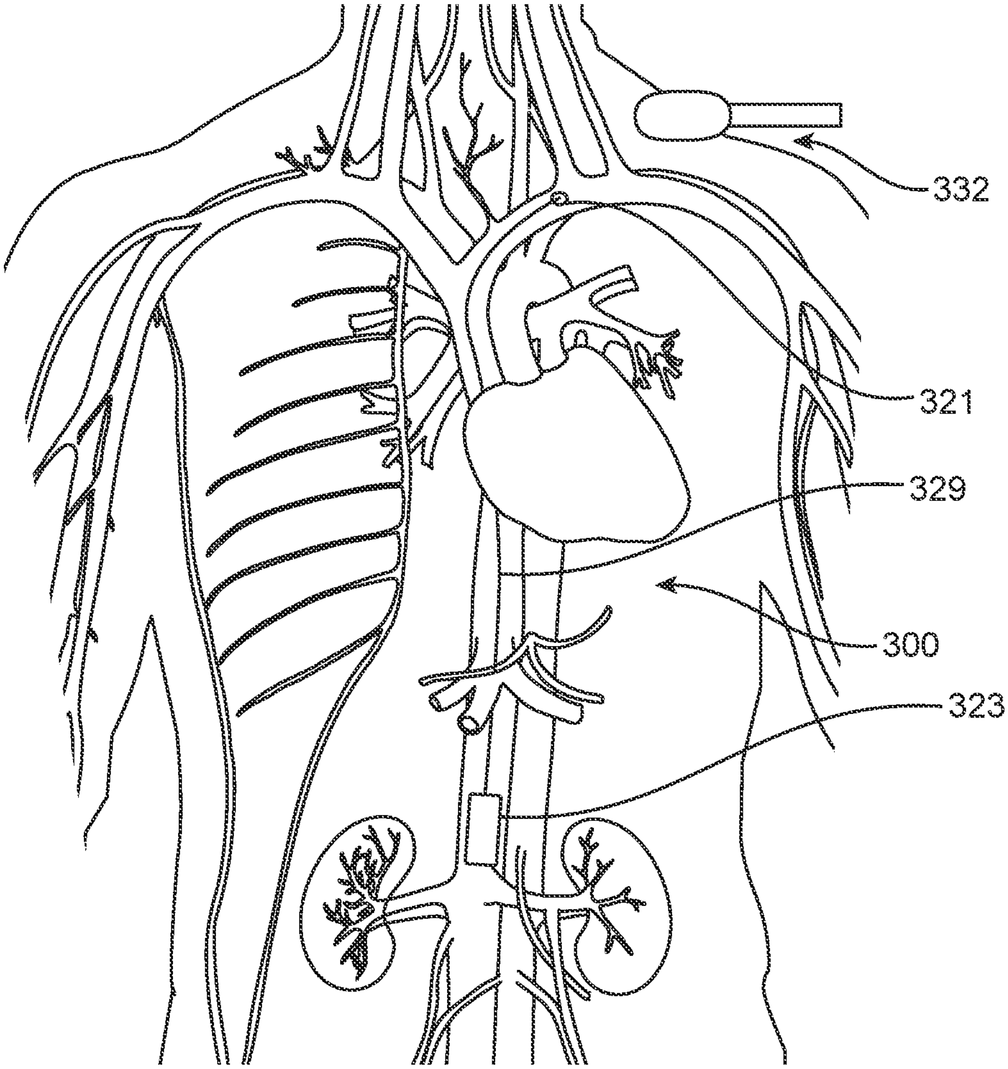
FIG. 3 is a schematic illustration of one disclosed embodiment of an implantable device, showing its placement in the vasculature.

In an alternative embodiment, device 300 may have a secondary element 321 that deploys portions of the device within the vascular system much closer to a point of insertion, or at another location more easily accessed (for physical access or energy transfer), as shown in FIG. 3. In this embodiment, device 300 includes IVC sensing unit 323 (which may be generally configured including anchor element(s) and marker element(s) as described with respect to other embodiments disclosed herein), with secondary element 321 located remotely from the sensing unit 323, and lead 329 connecting and providing communication between the two units. For example, an antenna element for telemetry and/or an inductive coil may be placed in secondary unit 321 in the subclavian vein or jugular vein. This would make it much easier to accurately position an external power source and/or controller antenna 332 close to the antenna or inductive coil contained within secondary unit 321. The secondary unit 321 may be held in place, for example, using a self-expanding stent or other intraluminal anchor element as described herein.

Figure 4:
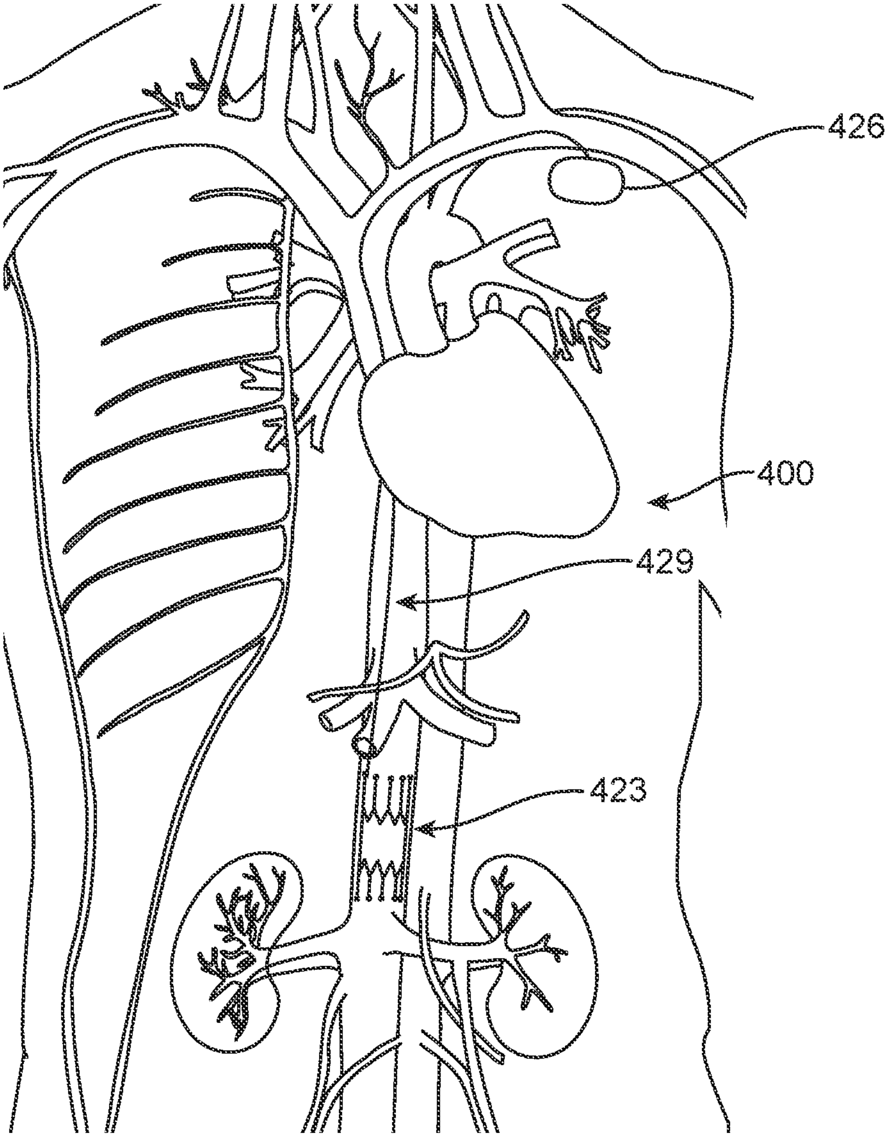
FIG. 4 is a schematic illustration of another disclosed embodiment of an implantable device, showing its placement in the vasculature.

Alternatively, an implantable device according to the present disclosure may have an implantable battery and circuitry that can be implanted within the body, but outside of the vascular system as shown in FIG. 4. Device 400 comprises IVC sensing unit 423 (which also may be generally configured as described with respect to other embodiments disclosed herein) and implantable controller/battery unit 426 connected to sensing unit 423 by lead 429 providing communication there between. There are similarities between placement of device 400 and the common placement of pacemakers and defibrillators in an infra-clavicular pocket. However, unlike those common devices, lead 429 between the IVC sensing unit 423 and placement location of controller/battery unit 426 would not need to traverse any heart valves, which may make it a relatively safe and simple connection. Alternatively, IVC sensor 423 may be adapted to connect to a pacemaker or defibrillator, including additional leads providing sensing and stimulation of the heart, for example, as described below in connection with the embodiment of FIG. 45.

A further exemplary embodiment is shown in FIGS. 5-10. As shown therein, device 500 comprises three major components or assemblies, electronics capsule 503, anchor element 506 and anchor isolation structure 507 connecting the electronics capsule and anchor element. Electronics capsule 503 comprises a sealed housing 509 for containing control, power and other alternative functional modules as elsewhere described herein to provide a self-contained, sealed device. Capsule 503 also provides support for marker element 512, which in the case of device 500 is a single ultrasound marker element positioned at the inferior end of the device. Such a marker element may utilize one or more ultrasound crystals to measure IVC diameter by emitting an ultrasound pulse, and then detecting the reflection of that pulse from the opposing wall of the IVC. Other modes of detection with ultrasound receivers and/or other marker element types as described herein may be alternatively employed by persons of ordinary skill without departing from the teachings of this disclosure. Electronics capsule 503 generally will be provided with the lowest possible profile so as to minimize obstruction of the lumen when positioned in the IVC.

Electronics capsule 503 is connected to anchor element 506 at the superior end of the capsule. Anchor element 506 as depicted in this embodiment includes a single anchor wire 515 configured in a generally figure-eight or double helix shape. Alternatively, the same configuration can be provided with two or more wires. Anchor wire 515 is pinned to telescoping deployment member 518 at both its inferior end 521 and superior end 524. Telescoping deployment member 518 includes inner member 527, which is secured to electronics capsule 503, through anchor isolation structure 507 and outer member 530. Relative motion between inner member 527 and outer member 530 moves anchor wire 515 from a collapsed position, shown in FIG. 9, to a deployed or anchoring position, shown in FIG. 10.

Various actuation mechanisms may be utilized for deploying and securing anchor element 506. In one alternative, anchor wire 515 is resilient, with shape-memory properties configured to provide a rest state in the deployed configuration. In this alternative, device 500 may be delivered to the desired location in the IVC via a conventional guide catheter or other suitable sheath type delivery device. When position is confirmed as described below, device 500 is ejected from the delivery catheter or sheath with anchor element 506 self-deploying upon ejection.

In another alternative deployment mechanism, an actuating wire (not shown) is removably connected to deployment member 518 at superior end 524 using a mechanical release mechanism, for example a screw threaded connection, spring release, hooks or other such means known in the art. The actuating wire may be a single or double wire, which may be coaxial or parallel, depending on the mode of actuation. In this alternative, movement of the actuating wire effects relative movement of the inner and outer deployment members 527, 530 to deploy anchor wire 515 from the collapsed configuration to the expanded, deployed configuration as explained above. After deployment of the anchor element, the actuating wire is released from device 500 according to its mode of connection and released to leave the device secured in the IVC via anchor element 506.

As mentioned above, a further feature of this and other embodiments disclosed herein is the spacing between the marker element position relative to the anchor element, provided by anchor isolation structure 507. In general, it is preferred if the anchor element is positioned sufficiently distant from the marker elements so as to not have an effect upon the IVC size or shape at or close to the location of measurement due to the anchoring force imparted to the IVC wall. Anchor isolation structure 507 ensures the desired positioning, which may be approximately 1 to 4 times the IVC diameter as indicated above. In general, the IVC has a somewhat oval cross section with a minor axis of the oval extending in the anterior-posterior direction and a major axis extending in the lateral-medial direction. It is thus desirable to minimize any effect of the device on this natural oval shape at or close to the point of measurement.

Figure 7:
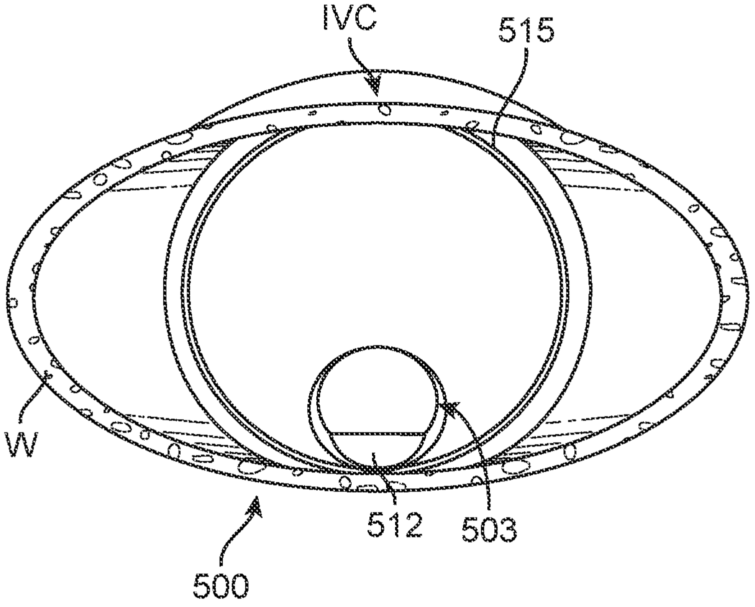
FIG. 7 is an end view of the embodiment of FIG. 5 as viewed in the IVC from the superior aspect.
Figure 8:
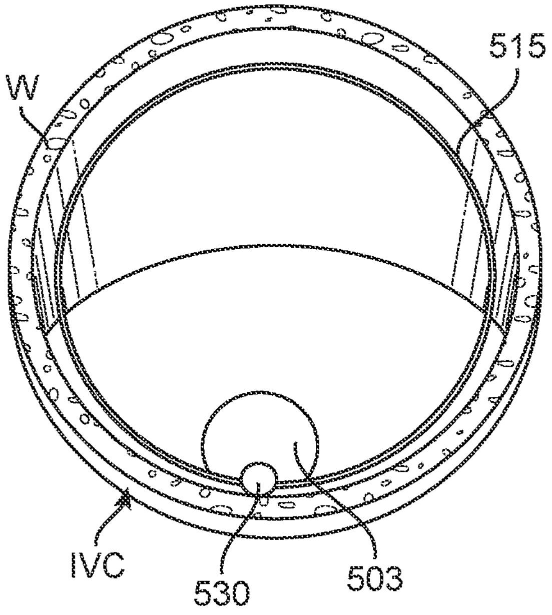
FIG. 8 is an end view of the embodiment of FIG. 5 as viewed in the IVC from the inferior aspect.
Figure 9:
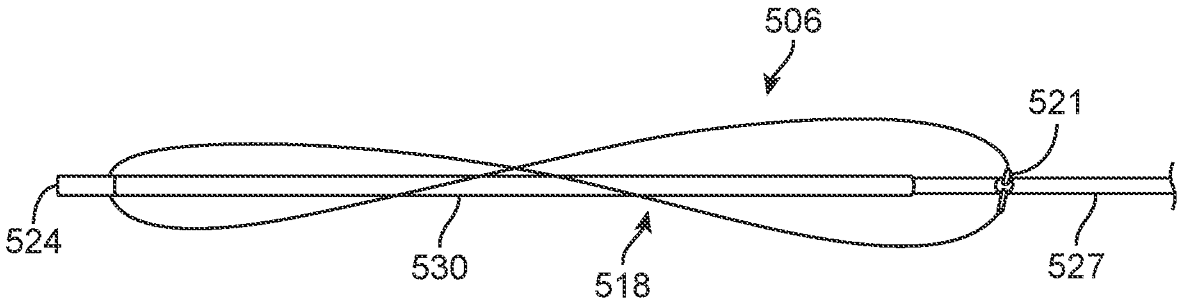
FIG. 9 is a detail of the anchor element of the embodiment of FIG. 5 in a collapsed configuration.
Figure 10:
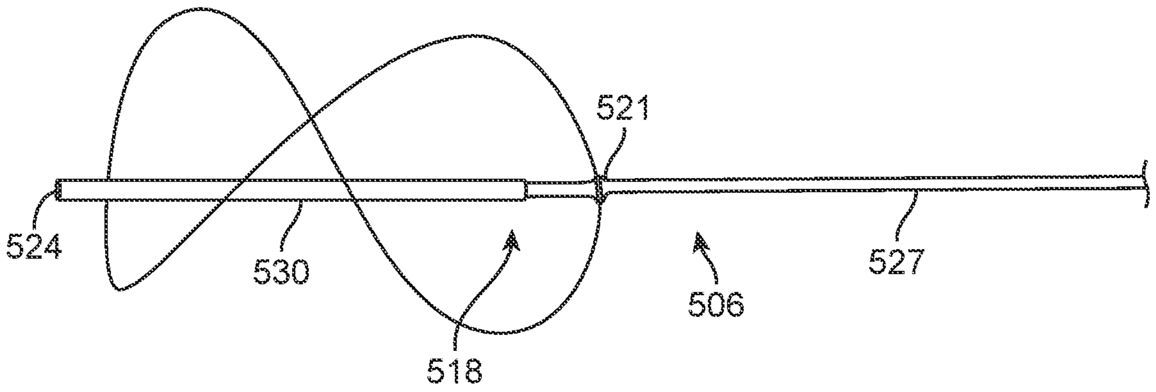
FIG. 10 is a detail of the anchor element of the embodiment of FIG. 5 in an expanded or deployed condition, shown outside the IVC.

The shape of the IVC and possible effect of the anchor element on the IVC shape is illustrated, in one possible configuration, in FIGS. 5-8. As shown therein, at the more inferior portion of the IVC, proximate marker element 512, the IVC assumes its more natural oval shape as best seen in FIG. 7. However, at the superior portion where subjected to the force of anchor wire 515 of anchor element 506, the IVC is forced into a more circular shape as best seen in FIG. 8. Thus, not only does the anchor element potentially distort the shape of the IVC, it may also stiffen the IVC so as not to be as responsive to varying fluid volumes which may indicate heart failure risk. Anchor isolation structure reduces or eliminates such problems as might otherwise be associated within sensing devices positioned in the IVC.

In order to achieve accurate measurement with marker element 512 using an anchor configuration of the type shown in FIGS. 5-10, the entire device, from deployment member 518 through anchor isolation structure 507 into electronics capsule 503 should be provided with a stiffness sufficient to maintain the electronics capsule (and marker element) against the wall of the IVC at one side and yet provide sufficient flexibility (and smoothness) to avoid damage or erosion of the IVC wall by contact with device 500 over the remaining lifetime of the patient.

As also shown in FIGS. 5-8, it may be most advantageous if the device, such as device 500, or other device disclosed herein, is positioned with the electronics capsule 503, and more specifically the active marker element (e.g., ultrasound marker element 512), against the posterior wall of the IVC so as to measure the distance to the anterior wall. This arrangement may offer advantages in accuracy and sensitivity in measurements by measuring along the minor anterior-posterior axis of the oval IVC shape, and by measuring from the posterior wall, bony structures lying behind the posterior wall, which may create artifacts or other interference with ultrasound measurements may be avoided. Such positioning may provide for the greatest accuracy in measurement of diameter over the respiratory cycle (e.g., measurement of diameter variability vs. static measurement). While a single ultrasound marker element 512 is shown for device 500, a similar device with more than one ultrasound crystal may be positioned elsewhere in the IVC, for example in the center of the IVC, with two crystals measuring the distance to the anterior and posterior walls simultaneously. Specific requirements for positioning and measurements may be clinically determined based on patient anatomy as determined by the procedure provider, and the device to be implanted may be modified according to the teachings contained herein to suit those specific patient requirements.

In general, devices as disclosed herein may be positioned at any suitable position in the IVC based on clinical assessment. In one example, the marker element of the device, such as an ultrasound crystal, may be disposed at the cranial end of the device, with the cranial end then positioned in the IVC between the renal veins and the hepatic veins. In this case, the anchor element may be disposed at the opposite, caudal end of the devices and thus positioned in the IVC inferior to the renal veins. Also, when positioning the device on the posterior wall of the IVC, it may be desirable to ensure that the device is centrally located on the posterior wall and oriented at least substantially straight across the minor axis for most accurate measurements. Positioning of the device in the IVC may be controlled using convention catheterization techniques with observation under fluoroscopy. However, in a device such as device 500, marker element 512 may be used to assist in confirming placement by slightly rotating electronics capsule 503 so as to effectively scan the opposite IVC walls with the ultrasound sensor to detect placement position relative to the oval IVC cross-sectional shape.

Figure 5:
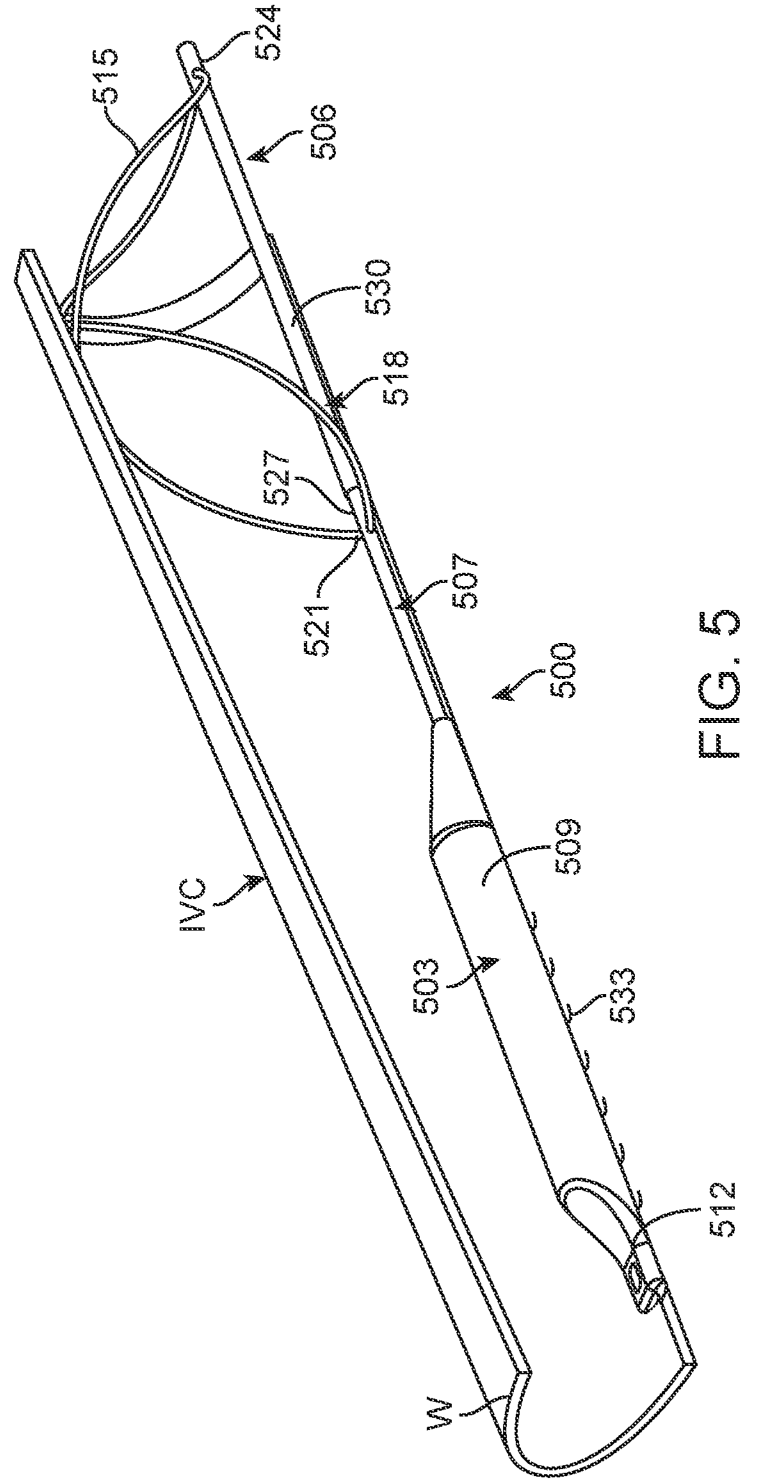
FIG. 5 is a perspective view of a further alternative embodiment positioned in a partially cross-sectioned portion of the IVC.
Figure 6:
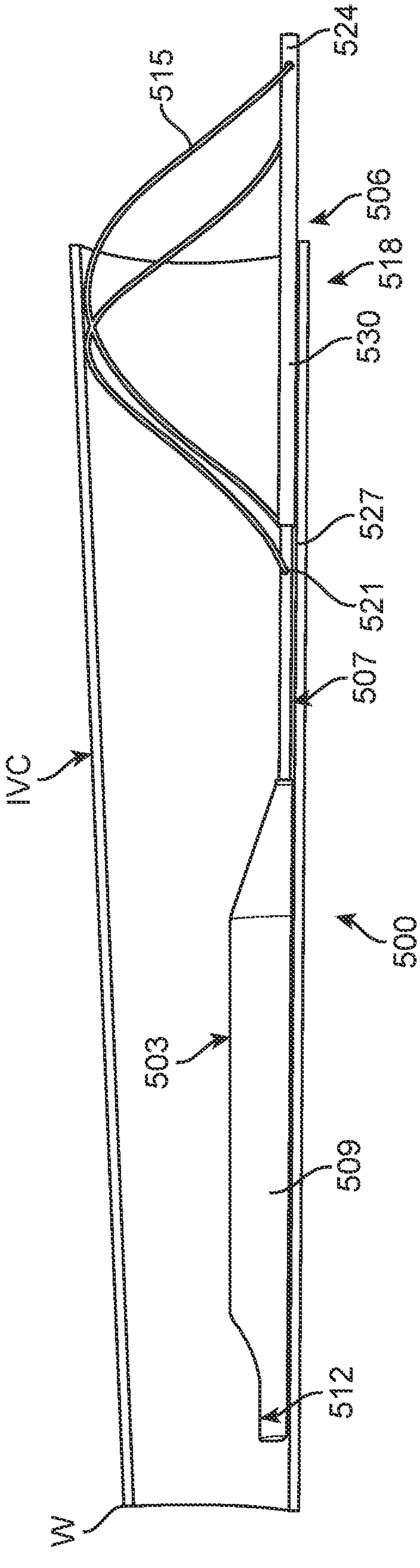
FIG. 6 is side view of the embodiment shown in FIG. 5 and the partially cross-sectioned IVC.

In a further alternative embodiment in FIG. 5, additional anchor elements may be provided on electronics capsule 503, such as barbs 533. It is to be noted, however, that while barbs 533 are shown in FIG. 5, they are an optional feature. Basic operation of anchor element 506 is described above. As anchor element 506 opens, it shortens and tends to pull back on electronics capsule 503. Through a linkage between barbs 533 and deployment member 518, the relative movement of those two parts during deployment of anchor element 506 may be used to deploy barbs 533 from the back of electronics capsule 503. Anchor element 506 and barbs 533 may be positioned to engage the IVC wall in opposition to one another to reinforce the anchoring force and security. However, as previously indicated, substantially the same device may be alternatively provided without anchor barbs 533, held in place only by the collapsible/expandable double helix anchor wire 515 of anchor element 506. These anchor structures, as well as further alternative anchor structures described below, are configured to achieve secure fixation against both longitudinal and rotational movement while preferentially maintaining at least the marker element in the posterior aspect of the IVC, most preferably against the posterior IVC wall. The anchor elements described also can be deployed and redeployed multiple times during a placement procedure in order to ensure the most optimum placement of the device. The shape or configuration of the anchoring wire also may be adapted for IVC size and shape using different anchor element configurations as exemplified by the following additional alternatives.

Figure 11:
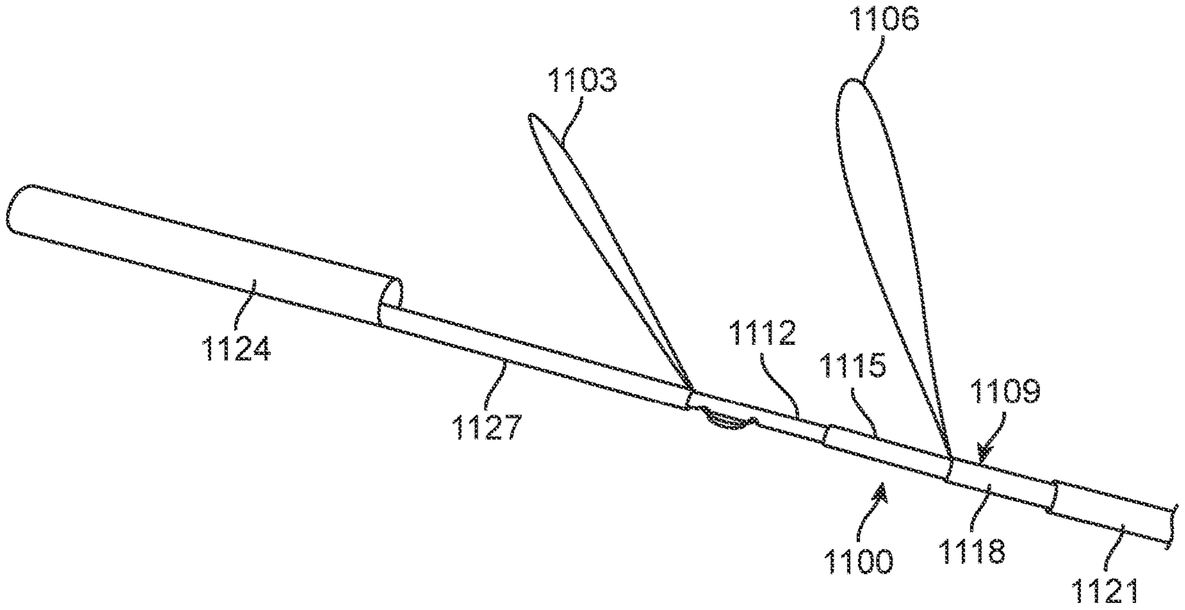
FIGS. 11 and 12 are perspective views illustrating a further alternative embodiment of anchoring elements, in deployed and collapsed configurations, respectively.
Figure 12:
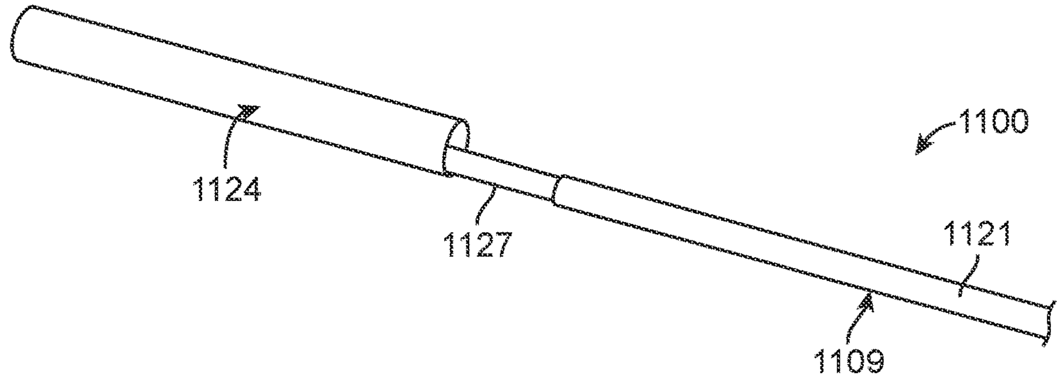

The anchoring elements exemplified herein may take a wide variety of alternative shapes, as shown generally in FIGS. 11-21. Such alternatives may or may not utilize one or more aspects of the "double helix" anchor wire design discussed above Alternative anchor element 1100 is shown in FIGS. 11 and 12. Anchor element 1100 includes two separate wire loops 1103 and 1106 secured to deployment member 1109, which is comprised of an inner member 1112 and concentric telescoping members 1115 and 1118, which are in turn covered by outer telescoping member 1121. Wire loop 1103 is secured to inner member 1112 and covered directly by inner concentric telescoping member 115. Second wire loop 1106 is also secured to inner member 1112, either by access through an opening in the concentric telescoping members or by an attachment wire that extends along the inside of telescoping member 1118 and is secured at the remote end to inner member 1112. Alternatively, second wire loop 1106 may be secured directly to the second concentric telescoping member 1118. In the collapsed configuration each wire loop is covered at least in part by one of the telescoping members. To deploy the anchor element, the telescoping members are pulled back, either by self-deployment forces generated by the wire loops or by actuation with external means as previously described. FIG. 12 shows anchor element 1100 in its fully collapsed state with the anchor wires and concentric telescoping members 1115, 1118 covered by outer telescoping member 1121. Also shown in FIGS. 11 and 12 is a further alternative electronics capsule 1124, which is joined to anchor element 1100 by anchor isolation structure 1127.

Figure 13:
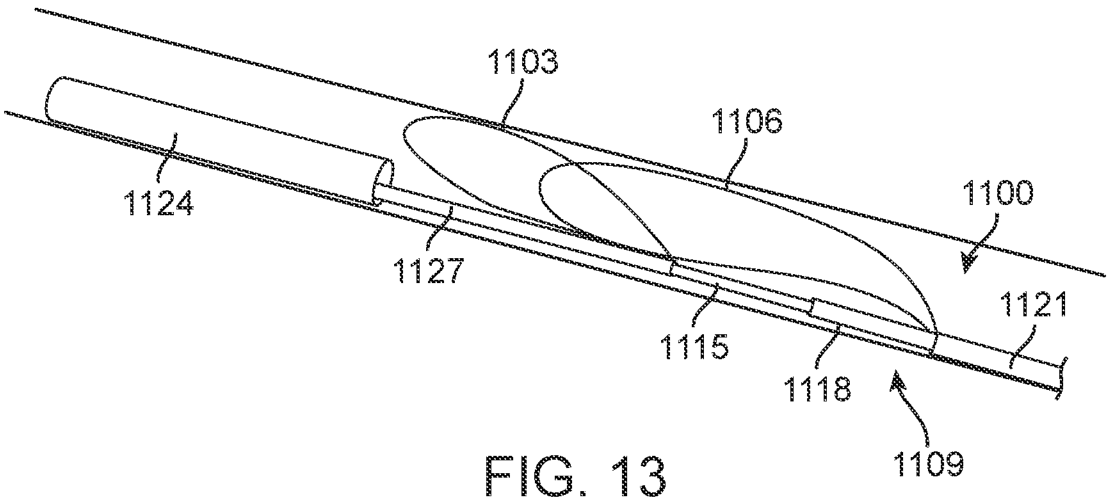
FIG. 13 is a perspective view illustrating the embodiment of FIGS. 11 and 12 as it may appear deployed within the IVC (note that for illustration purposes the orientation is not intended to be anatomically accurate in this or similar figures).

FIG. 13 illustrates anchor element 1100 and electronics capsule 1124 as it may appear when deployed within the IVC. Anchor wire loops 1103 and 1106 are released to extend outwardly to contact the IVC wall while leaving the central portion of the IVC unobstructed to allow access for other procedures and to minimize restriction of blood flow.

Figure 14:
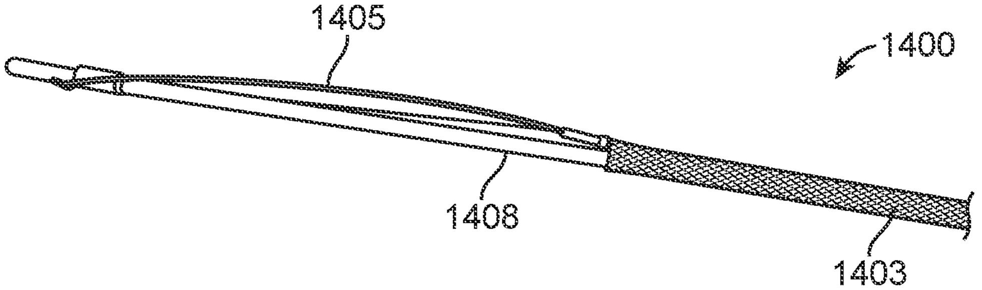
FIGS. 14 and 15 are perspective views illustrating yet another alternative embodiment of an anchor element, in the collapsed and deployed configurations, respectively.
Figure 15:
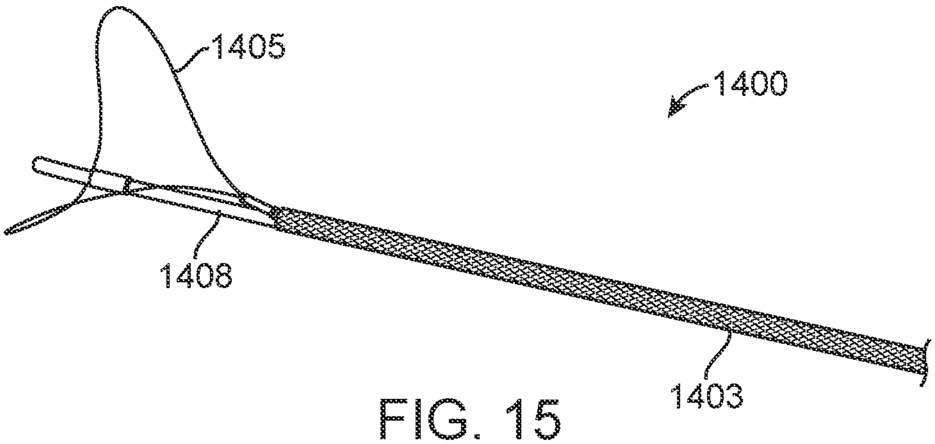
Figure 16:
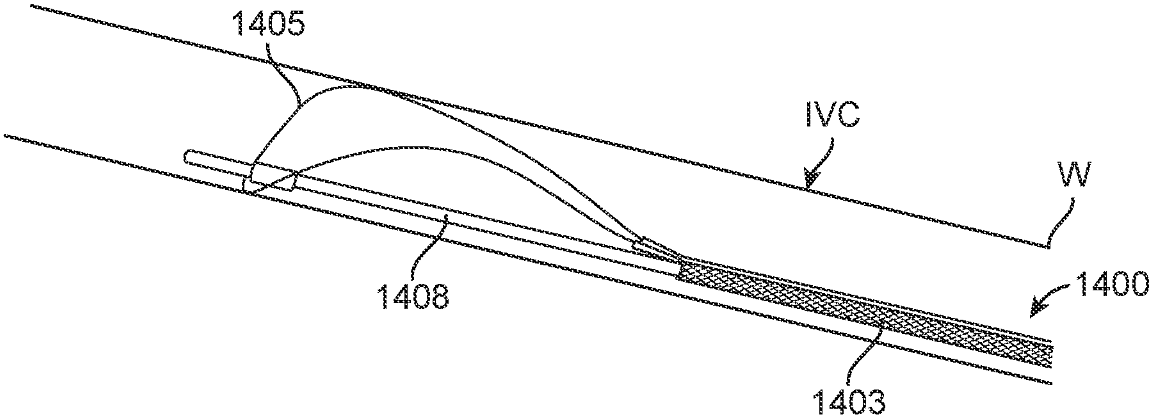
FIG. 16 is a perspective view illustrating the embodiment of FIGS. 14 and 15 as it may appear deployed within the IVC.

FIGS. 14-16 illustrate another alternative anchor element 1400. In this embodiment, mesh sleeve 1403, secured at one end to anchor wire 1405 is deployed over inner member 1408 to which anchor wire 1405 is secured. Once again, relative movement between inner member 1408 and mesh sleeve 1403 controls deployment or collapse of the anchor wire 1405. Anchor element 1400 is depicted in FIG. 16 as deployed within the IVC with wire anchor 1405 engaging the IVC wall.

Figure 17:
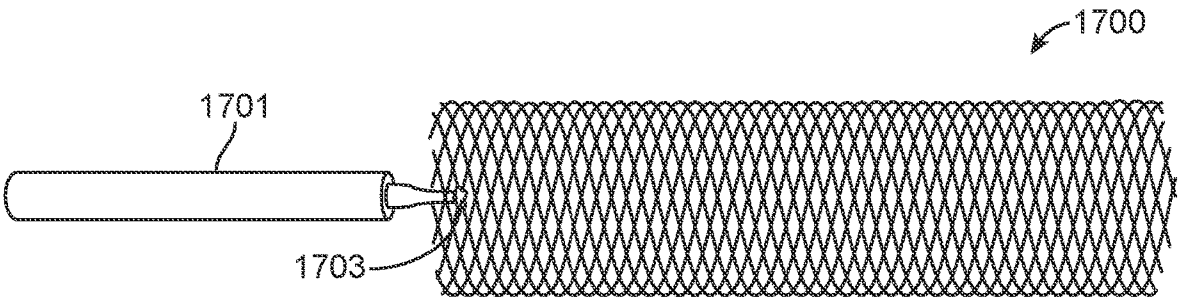
FIG. 17 is a side view illustrating another alternative embodiment of an implantable IVC monitor with a stent-like anchor element and electronics capsule.

FIG. 17 illustrates a collapsible, tubular, stent-like alternative anchor element 1700. Anchor element 1700 may be formed of braided wires, welded wires, spiral wound wire, or laser-cut tube, and is preferably a resilient self-expanding metal or polymer. Electronics capsule 1701 is depicted as attached to one end of the anchor element. Weld or cold bond 1703 with biocompatible materials may be used to attach the electronics capsule to the anchor element. Anchor element 1700 may be deployed through a guide catheter in a manner similar to conventional stent deployment. Advantageously, such a tubular anchor element provides secure anchoring in the vessel while leaving the vessel lumen patient to allow introduction of catheters and other devices without disruption of the monitoring device.

Figure 20:
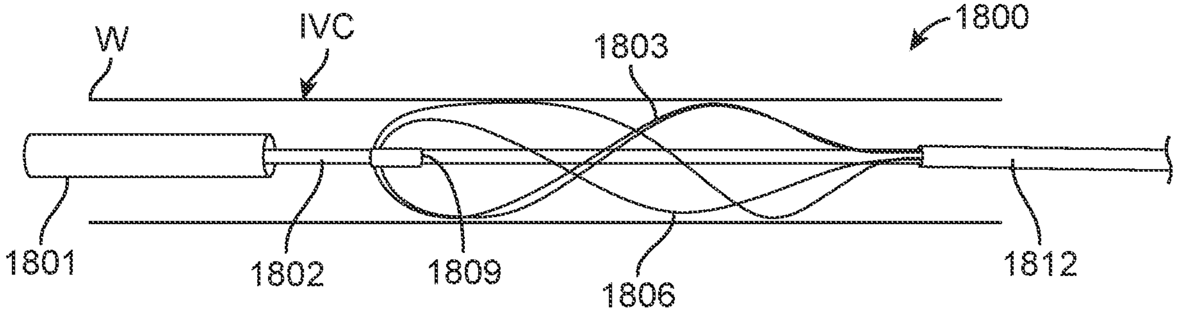
FIGS. 20 and 21 are perspective views illustrating the embodiment of FIGS. 18 and 19 as it may appear deployed within in IVCs of different dimensions.
Figure 21:
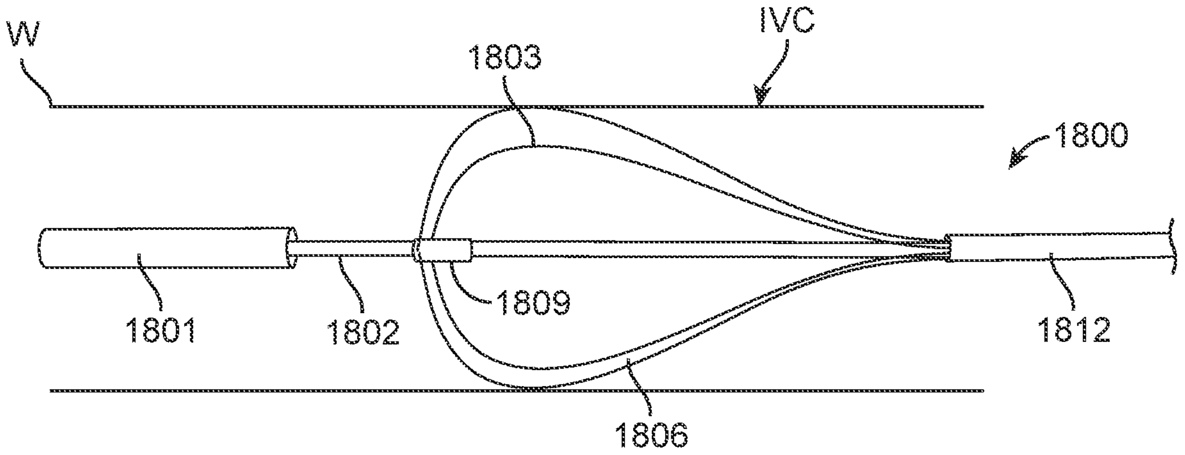

FIGS. 18-21 illustrate yet another alternative anchor element 1800 coupled with electronics capsule 1801. In this embodiment, anchor wire loops 1803 and 1806 in this embodiment are secured at opposite ends to inner member 1809 and outer member 1812. In this manner, relative movement between inner member 1809 and outer member 1812 permits deployment of the anchor wires without a covering sheath. The anchor wires may be again collapsed by an opposite relative movement between the inner member and outer member. FIGS. 20 and 21 show how anchor element 1800 may be deployed in different sized IVCs. In this embodiment, anchor wire loops 1803 and 1806 are relatively longer such that they may cross multiple times when less than fully expanded to accommodate smaller size IVCs, as is apparent from a comparison of FIGS. 20 and 21.

As should be apparent to those of ordinary skill in the art, each of the anchor element configurations described above includes common features of secure anchoring with a virtually unobstructed IVC, even when the anchor elements are fully deployed. By minimizing or eliminating obstruction of the IVC, combined with positioning of the anchor elements remote from sensing elements and location, embodiments of the present disclosure may remain positioned in the IVC over longer periods of time without affecting the natural tendency of the IVC to collapse or expand when venous pressure or volume is changed.

Figure 22:
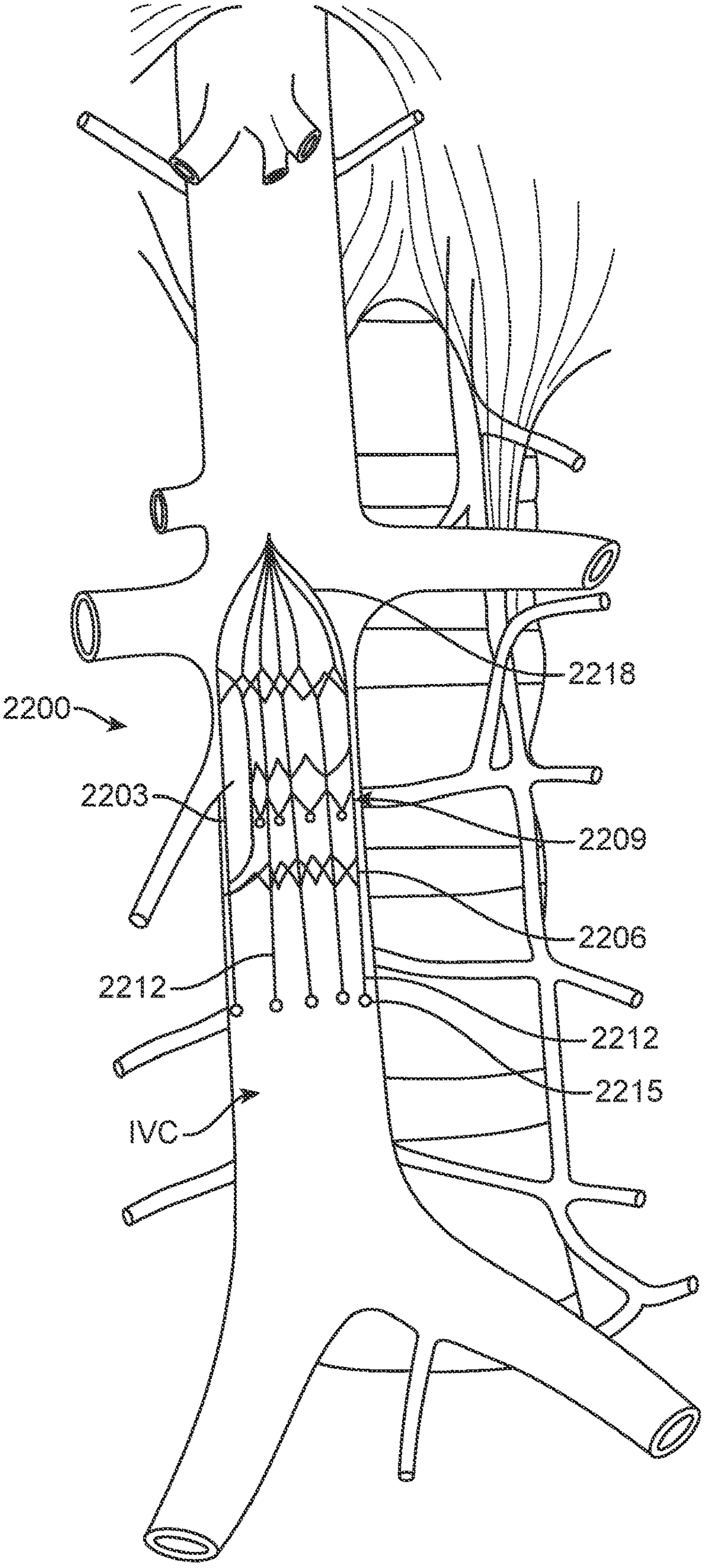
FIG. 22 is a schematic illustration of a further embodiment of implantable device positioned in the IVC according to the present disclosure.

While it is anticipated that in most cases it will be desirable to maintain an unobstructed pathway through the IVC as provided by exemplary anchor elements described above, in some cases it may be desirable to integrate a monitoring device as described herein with an IVC filter, as shown for example in FIG. 22. In addition to monitoring IVC distention, device 2200 would trap any clots embolizing from the legs and prevent them from reaching the lungs as is understood with respect to IVC filters as stand-alone devices. Device 2200 includes electronic capsule 2203 with battery, connections to the sensor, memory, telemetry, etc., stent-like anchor element 2206 with anchor members 2209, and flexible arms 2212 supporting marker element 2215. In this embodiment, marker element 2215 are depicted as electrodes, which may be substantially the same as the electrodes described above in connection with the embodiment of FIG. 1. In addition, arms 2218 at the superior end of device 2200 extend across the lumen of the IVC and intersect to form a basket to retain any clots which embolize from the legs.

Figure 23:
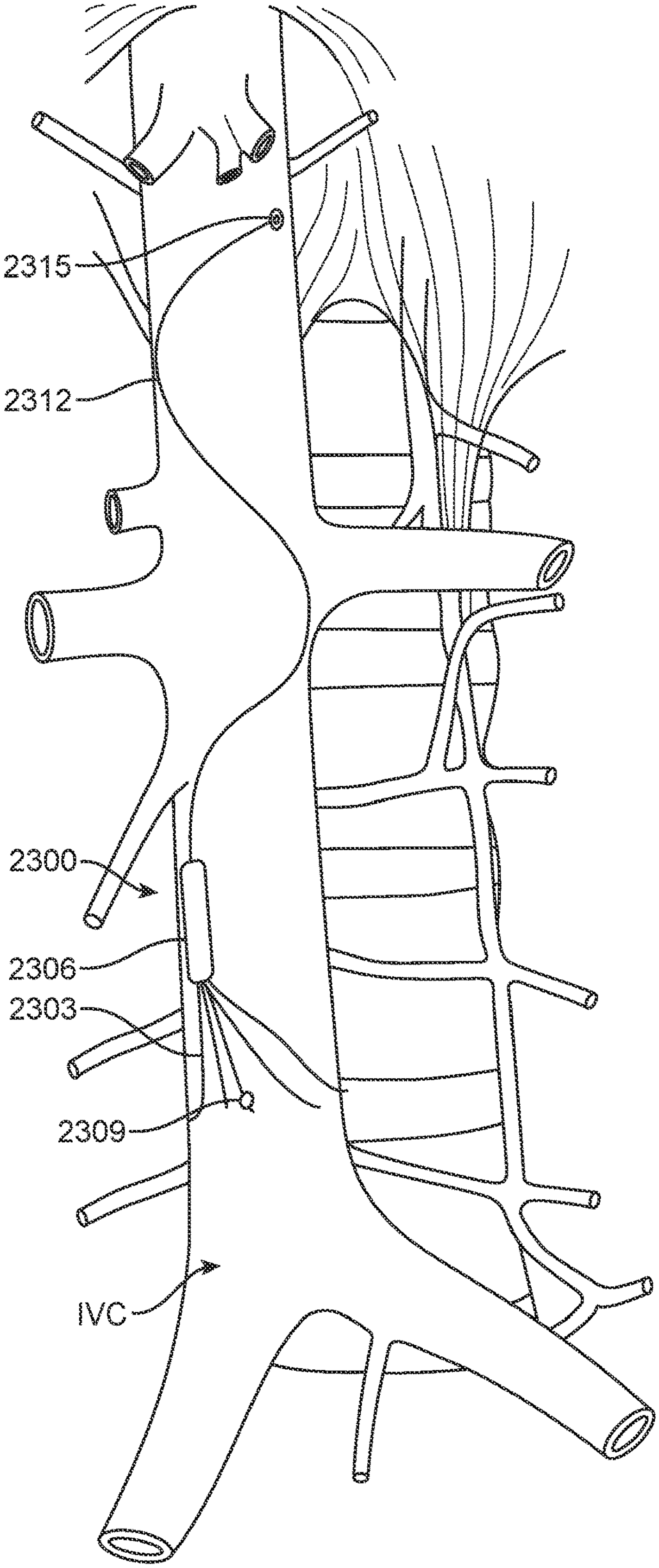
FIG. 23 is a schematic illustration of yet another embodiment of implantable device positioned in the IVC according to the present disclosure.

FIGS. 23 and 24 show devices 2300 and 2400, respectively, configured to measure the longitudinal impedance along the length of the IVC or the superior vena cava (SVC), or both. Device 2300 includes anchors 2303 to engage the IVC and secure electronics capsule 2306. One electrode 2309 is provided relatively closer to electronics capsule 2306, and an insulated straight or spiral wire 2312, which lays against the IVC wall, leads to second electrode 2315 located more superiorly in the IVC, right atrium, or SVC. Rather than applying a simple direct current voltage between these two electrodes to measure the impedance, it may be more effective to apply a particular alternating-current frequency that exhibits a lower impedance through blood and a higher impedance across the IVC wall and through other tissues. This would allow such a device to measure the variation in IVC volume even more effectively. Alternatively, a device may measure a combination of the change in both longitudinal and radial impedance, to gather an even more effective measurement of the change in IVC volume.

FIG. 24 further shows device 2400, shaped similarly to a standard IVC filter, which uses the variation in bending of struts 2403 to apply pressure to pressure sensors 2406 on central body 2409 of the device. Struts 2403 extend radially outward from body 2409 and have distal tips 2412 configured to engage and anchor to the wall of the IVC. Struts 2403 have flexibility and resilience so as to move with the wall as the vessel contracts and expands, thereby changing the forces exerted by the struts on sensors 2406. Electronics capsule 2415 is contained within body 2409 providing power, control and communication for sensors 2406.

Figure 25:
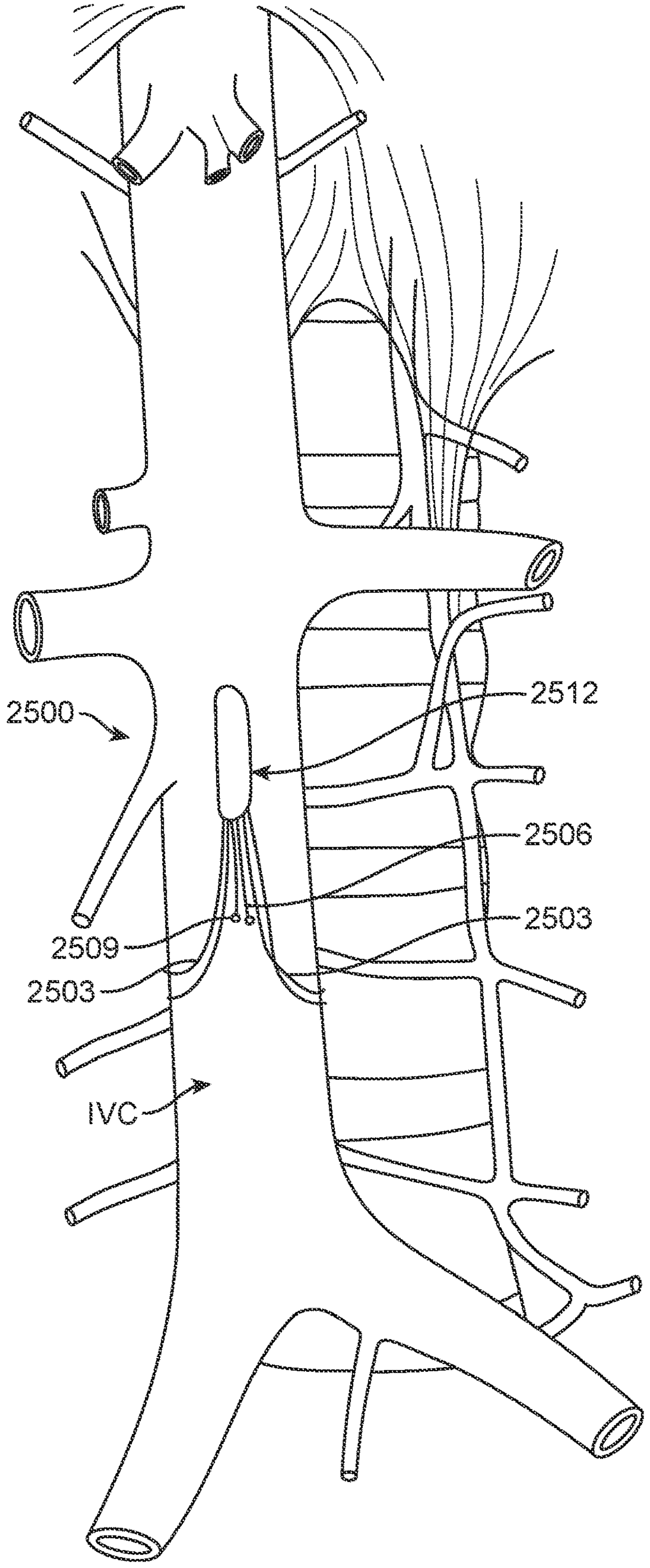
FIG. 25 is a schematic illustration of a further embodiment of implantable device positioned in the IVC according to the present disclosure.

FIG. 25 shows another embodiment, device 2500, configured similarly to an IVC filter. However, in this embodiment, device 2500 is provided with lateral struts 2503, which are intended to anchor the device in the IVC, and anterior-posterior struts 2506, which are intended to flex with the movement of the anterior and posterior walls of the IVC. Therefore, the distance between marker elements 2509, such as sensors or electrodes, on the anterior and posterior struts can be measured. As with other embodiments, device 2500 includes electronics capsule 2512, which provides structural support for the struts and contains necessary power and control functions as elsewhere described.

Figure 26:
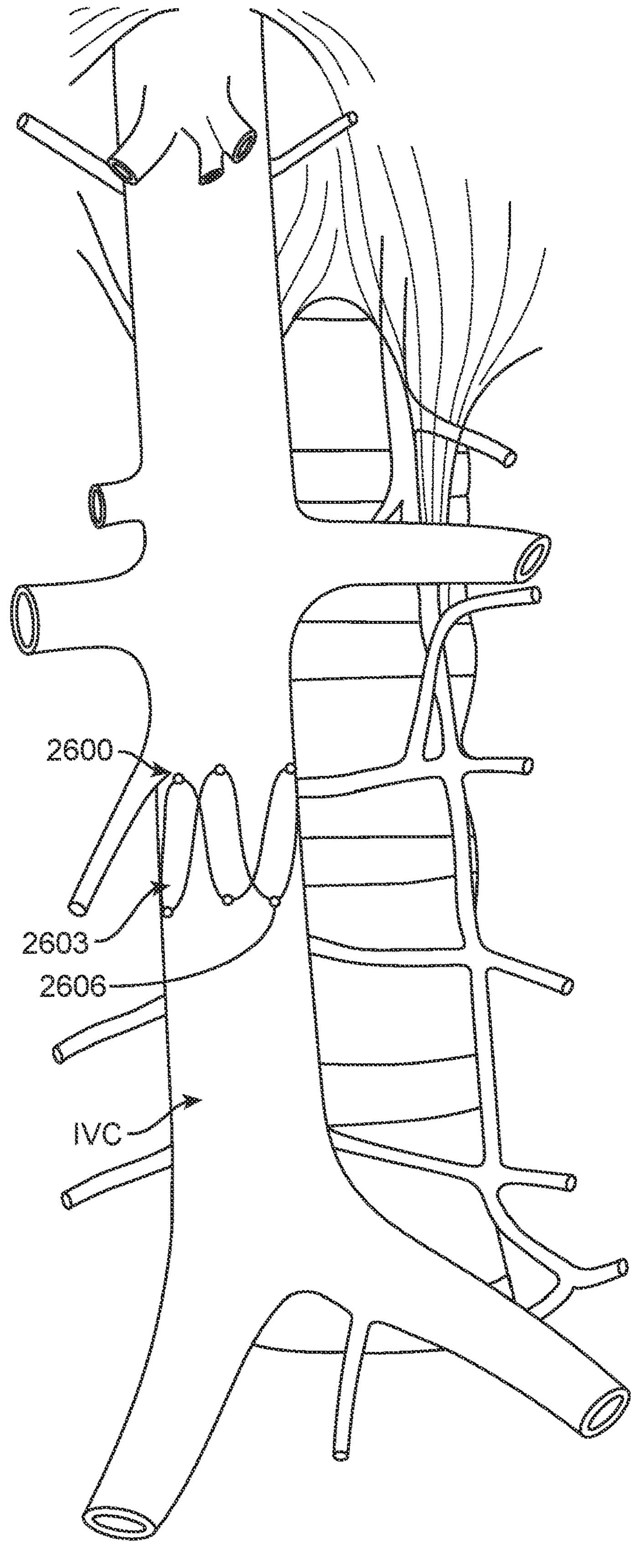
FIG. 26 is a schematic illustration of another embodiment of implantable device positioned in the IVC according to the present disclosure.

FIG. 26 shows a further alternative embodiment in which device 2600 is comprised as a stent 2603 on which marker element 2606 are disposed at two different cross-sections (lateral-medial and anterior-posterior) of the IVC. Stent 2603 has a resilient, self-expanding configuration which will expand and contract with the IVC. Stent 2603 may be a mesh or woven structure, a simple wire-form having a zig-zag or sinusoid shape, or a series of closed or open cells cut from a tube. Power and control may be provided by integrated power and data transmission components in an electronics capsule as previously described, or marker element sensors directly powered via external energy delivery means, and transmitting information directly to an external module may be provided.

Figure 27A:
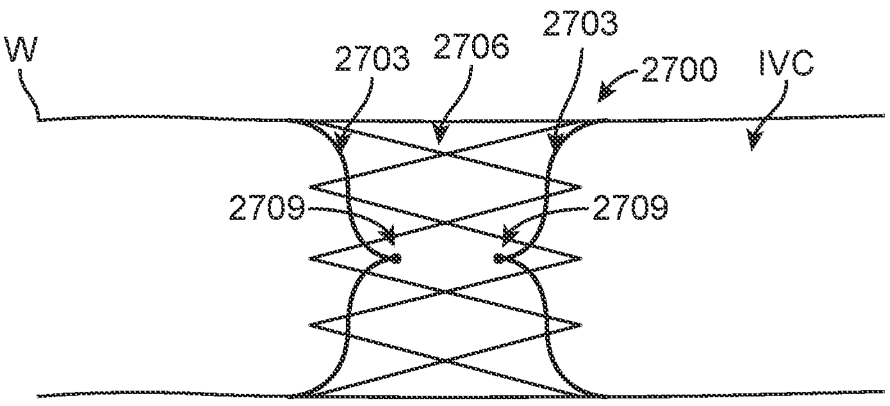
FIGS. 27A and 27B are schematic illustrations of a further embodiment of implantable device according to the present disclosure.
Figure 27B:
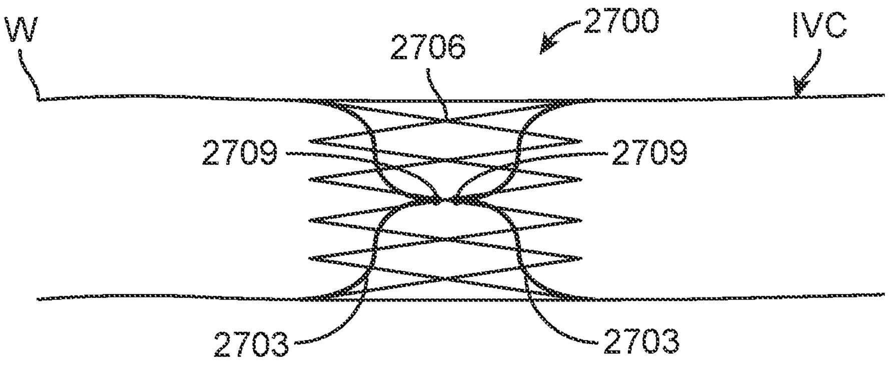

FIGS. 27A and 27B show another embodiment in which device 2700 is provided with two pairs of arms 2703 held in place by a stent structure 2706. Marker element 2709 (such as electrodes, ultra sound crystals or other sensors as previously described) are positioned at the apex of each pair of arms. These may be oriented in the patient such that one side of each pair extends from the anterior wall of the IVC, and one from the posterior wall. As the IVC collapses as shown in FIG. 27B, the arms tend to scissor together and the apices holding marker elements 2709 move closer together. This change in position may be detected. Alternatively, strain gage type sensors or other angle detection may be used to detect the change in angle from compression alone or in combination with the change in distance sensors. Embodiments such as device 2700 can be configured such that the sensors move relative to each other a distance greater than the actual movement of the IVC wall, thereby magnifying the change in the distance from the anterior to posterior walls.

Device embodiments as described herein may be delivered into the IVC from a variety of locations. The subclavian or cephalic vein is the normal route of introduction of pacemaker and defibrillator leads, so that these leads can be attached to the pacemaker itself, which is placed in an infra-clavicular pocket just below the subclavian vein. Embodiments disclosed herein may be similarly delivered from the subclavian vein, cephalic vein or the jugular vein, or the femoral vein. Other access points to the venous circulation may also be used.

One exemplary delivery method for certain embodiments disclosed herein is to have the device to be delivered compressed into a catheter, with a cover sleeve over the device. A guidewire lumen within the catheter would allow a guidewire to be positioned under fluoroscopy or ultrasound guidance into the IVC, and then the delivery catheter would be advanced over that guidewire into the appropriate location. Once appropriate location is confirmed, the cover sleeve would be retracted, allowing the device to self-expand against the walls of the IVC. Under appropriate clinical indications, disclosed devices may be delivered at the bedside under ultrasound imaging guidance, without the need for fluoroscopy.

If the device has an electronic lead, the lead may take advantage of all of the designs, materials, and techniques that have been used to optimize pacemaker leads. This lead may extend to a secondary fixation element within the circulatory system, as shown in FIG. 3, or it may extend out of the circulatory system to an implantable element as shown in FIG. 4.

As a source of power, embodiments described herein may include an inductance coil to power the sensors on the device using a power source from outside the body. Externally powered devices may also include a small battery or capacitor to maintain steady power to the sensors. An external power source could be in the form of a pendant which hangs from a necklace around the patient's neck, or a module which is kept in a shirt pocket, strapped around the patient's chest or abdomen, clipped to the patient's belt, or other locations proximate to the implanted device. It could also be kept at the patient's bedside or under their mattress or pillow, so it can deliver power, take measurements, download data, etc. each evening while the patient is sleeping.

Given the available cross-sectional area of the IVC and the low power requirements of current implantable device circuitry, embodiments of devices described herein, including a long-term battery and circuitry, may be safely implanted in the IVC without disrupting blood flow. The diameter of the delivery catheter for such a device may be as large as 24-30 French size (8-10 mm) if delivered via the femoral vein. The overall implanted device or structural elements also may be used as an antenna to enhance transmission of this data outside of the body, especially, for example, if the device has a stent-like body or multiple metal arms.

Figure 28A:
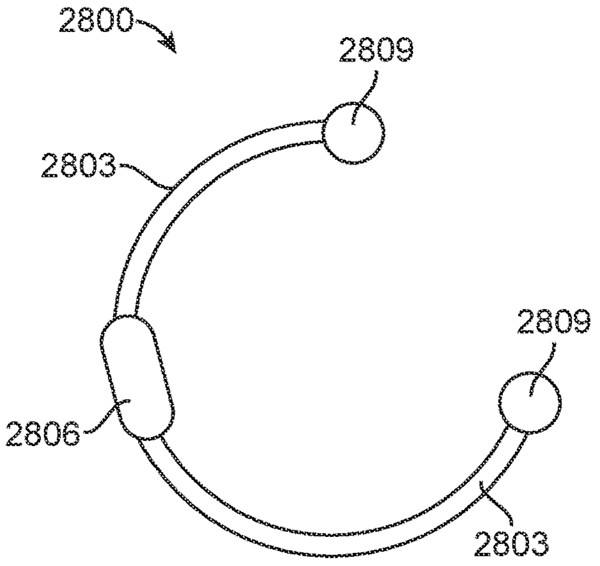
FIGS. 28A, 28B and 28C are a series of schematic illustrations showing delivery and placement of an embodiment of a device configured for external placement on the IVC according to an alternative of present disclosure.
Figure 28B:
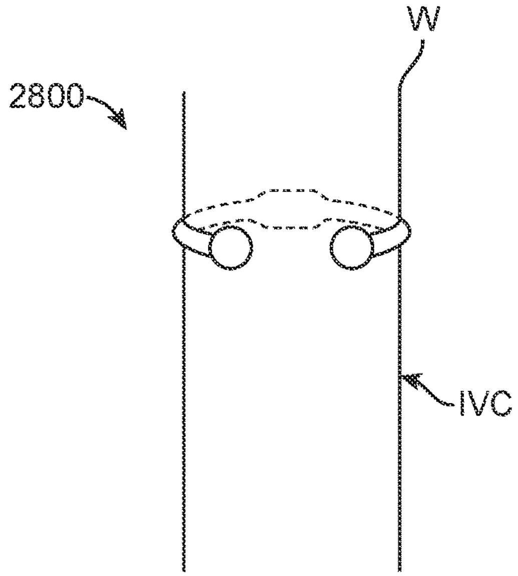
Figure 28C:
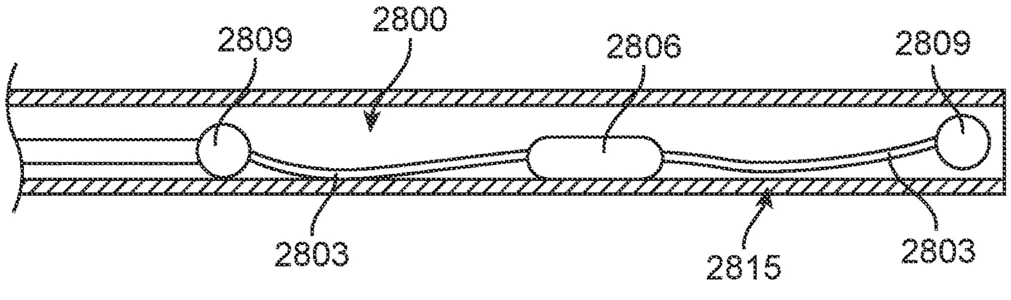

In yet another alternative embodiment, a sensing device may be implanted on the outside of the IVC as shown, for example, in FIGS. 28A-C. In this embodiment, device 2800 is configured to be implanted around the outside of the IVC and thus includes two resilient arms 2803 extending from electronics capsule 2806. Marker elements 2809 are disposed at the ends or elsewhere along resilient arms 2803. Arms 2803 may be, for example, a coated, resilient flexible material or a tubular insulator with a wire inside. Device 2800 may be placed via an otherwise conventional laparoscopic procedure. A right posterolateral access to the abdomen, just inferior and/or posterior to the liver, should allow the surgeon to advance to the IVC. In this manner a resilient loop device such as device 2800 could be wrapped around the IVC, as shown in FIG. 28B. FIG. 28C shows one embodiment of delivery device 2815 containing straightened device 2800. Delivery device 2815 may comprise a tubular member such as a catheter or trocar with a pushing element for delivery and position of device 2800 around the IVC.

In a further alternative embodiment, a marker element as elsewhere described herein may be implanted against one side of the external wall of the IVC, held in place by sutures, clips, adhesives, or other mechanical attachment means. Such an external sensor type element could measure IVC cross-sectional area via mechanical, sonic, impedance, or other means.

Marker Element Embodiments with External Activation

Embodiments described above focus on implantable systems with electronics to measure IVC dimensions as well as other physiologically important data, and then transmit that information to a receiver located outside the patient's body.

Embodiments described hereinafter include devices, systems, and methods for measuring the IVC employing external instruments to measure IVC dimensions in communication with implanted marker devices, potentially without a need for more complex implants, or implanted active measurement devices and/or the need to transmit measurement data out of the body. Such devices, systems and methods may include passive elements, which are used in conjunction with external instruments for calculating and communicating IVC dimensions. More specifically, disclosed systems may have one, two or more markers that would allow an instrument outside the body to easily measure IVC dimensions without the need for sophisticated training or human analysis. Such systems may use portable, and relatively inexpensive instruments to take the measurements.

Figure 29:
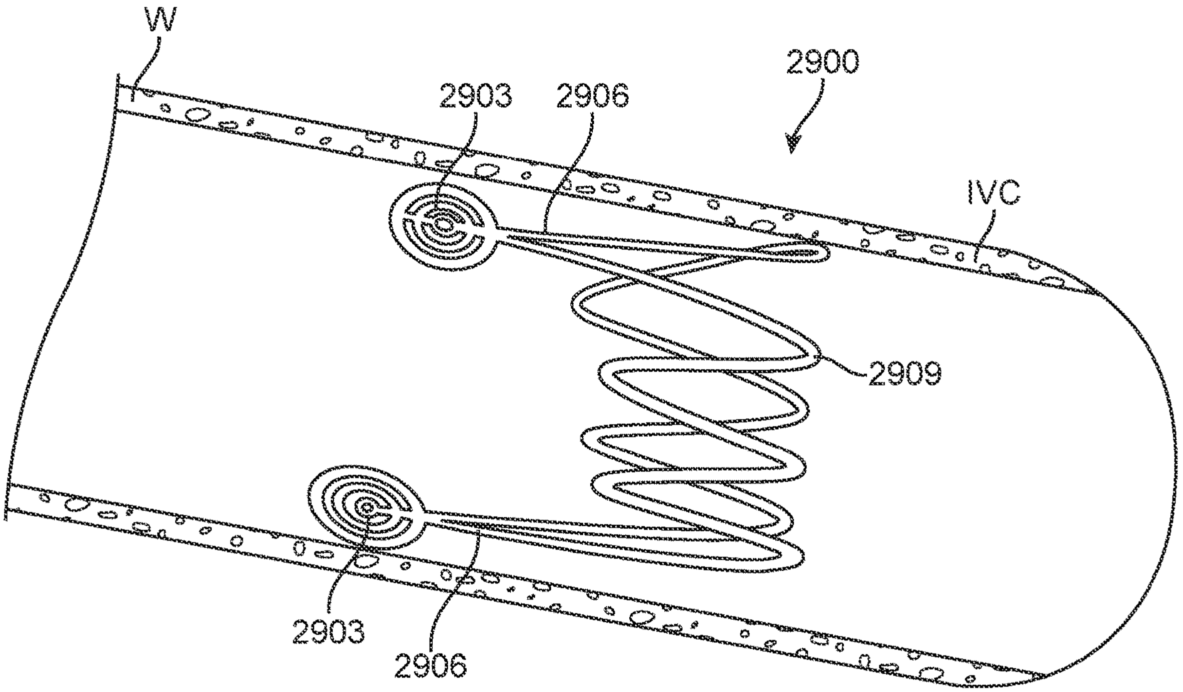
FIG. 29 illustrates another alternative device embodiment deployed in the IVC [1A-005].

In one disclosed embodiment, shown in FIG. 29, device 2900, including two or more passive elements 2903, is configured to be implanted in the IVC. Passive elements 2903 are themselves configured to reflect a signal directed towards them from outside the body. Such passive element reflectors may be made of a metal such as Nitinol, or they may be made from any other echoreflective material (or other suitable biocompatible material reflective of the signal employed). Passive elements 2903 are connected by anchor isolation structures 2906 to anchor structure 2909, exemplified here as a stent-like structure, which may be made of Nitinol or other resilient material biased into engagement with the IVC wall. Other anchor elements as described herein may be alternatively employed.

It will be appreciated by persons skilled in the art that the depiction in FIG. 29, as in other figures presented in this disclosure, is not at a particular scale. Connecting elements 2906 may be suitably elongated to allow the anchoring structure to be placed in a position spaced upstream or downstream from the location of the markers so that the anchoring structure does not affect the natural geometry and movement of the IVC where it is measured by the passive elements as previously described. Passive elements 2903 may be gently biased outwardly against the anterior and posterior walls of the IVC to maintain contact therewith.

In other embodiments employing passive marker elements, the passive elements may be mounted directly to an anchoring structure such as a stent, and not separated therefrom by connecting elements. Alternatively the marker elements may be stapled, screwed, sutured, or otherwise fastened to the IVC wall. Passive elements such as shown in FIG. 29 may be fenestrated, including grooves, channels, holes, depressions or the like to accelerate the ingrowth of IVC wall tissue over them. The passive elements may also have a surface texture or coating to enhance reflection of the signals. For example, the surface may have a series of grooves or depressions whose walls were at right angles or other selected angles relative to each other to more effectively reflect those signals. Alternatively, such grooves, channels or other features may be arranged on each passive element in unique patterns which make them more clearly identifiable and differentiable from each other and from surrounding structures by an external detection instrument. In other embodiments, the passive elements may be of known size, but oriented at different known angles relative to each other, such as in orthogonal directions (e.g. at least one in circumferential direction and one in the axial direction), so calculating the length and orientation of the reflected signal can determine the location of each passive element in three dimensions.

It is anticipated that within a few months of their implantation, the passive elements as of the types described herein would be fully healed into the IVC wall. The posterior passive element may be somewhat larger than or offset from the anterior passive element, so that one does not shield the other regardless of where the reading/detecting instrument is held against the anterior abdomen.

Figure 30:
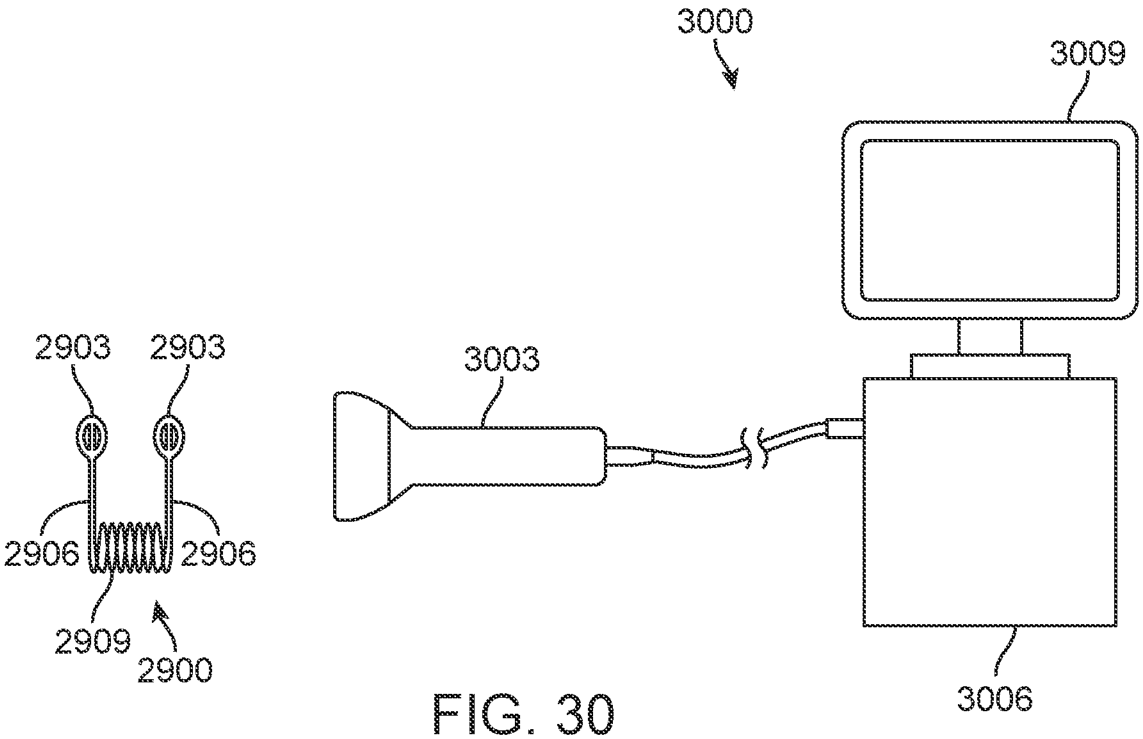
FIG. 30 schematically depicts an alternative embodiment of a system described in the present disclosure.
Figure 31:
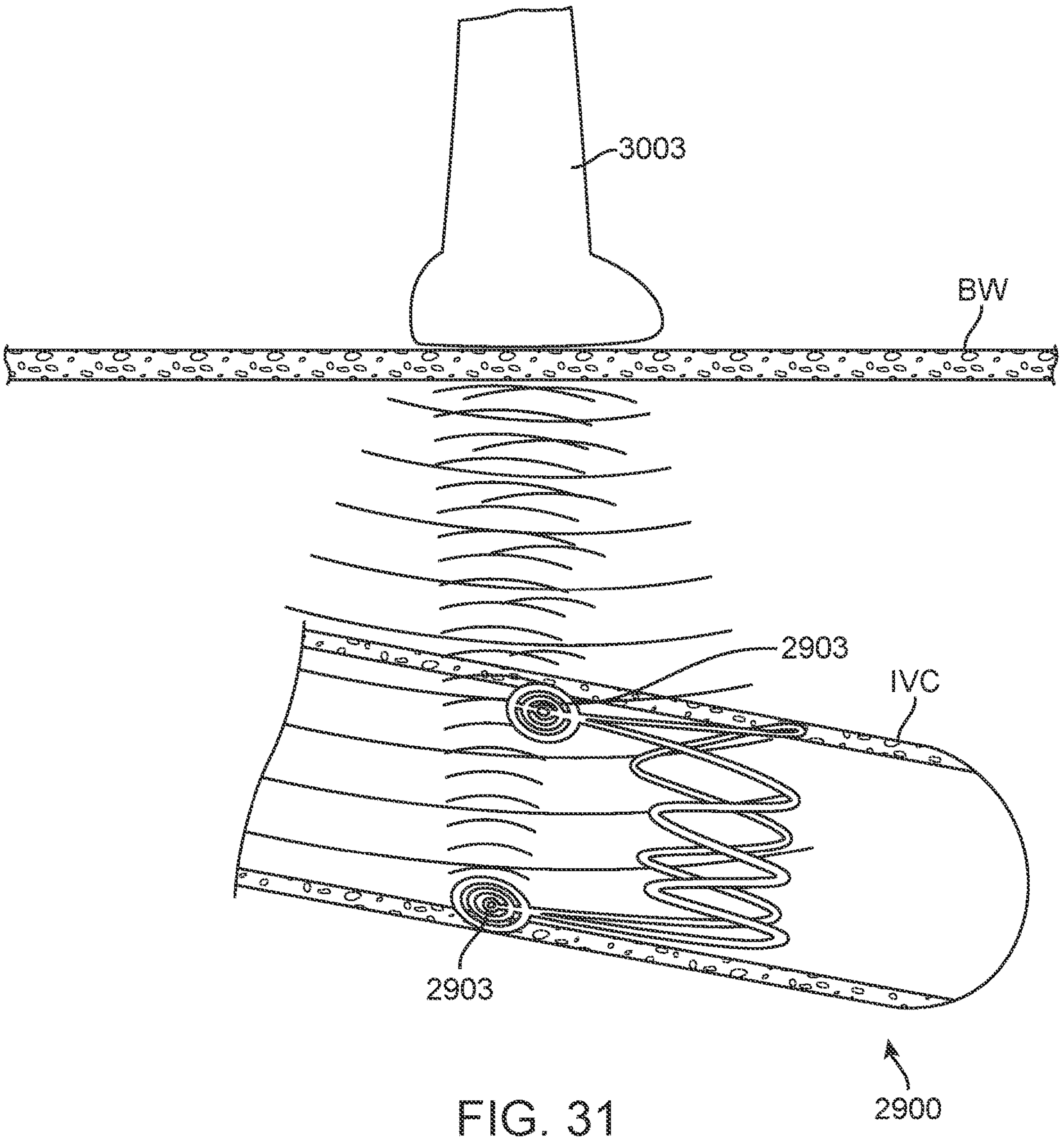
FIG. 31 schematically depicts an embodiment for detection of markers in a deployed device using ultrasound.

A reading instrument for use with passive elements as described above may comprise a generally conventional ultrasound signal generator and receiver which would be held against the anterior abdomen or thorax outside the body to detect the device in the IVC, as schematically depicted in FIGS. 30 and 31. In this exemplary embodiment, ultrasound system 3000 includes handheld probe 3003 connected to table top control console 3006 and display 3009. Advantageously, ultrasound system 3000 would not need to image the IVC, although optionally may do so. Thus, ultrasound probe 3003 could be provided as a single crystal, intermittently delivering a pulse and measuring the time-of-travel until the reflected echo is detected by the same crystal. Ultrasound probe 3003 transmits a sonic signal, as shown, for example, in FIG. 31, through the body wall BW and the receiver records the reflection of that signal from the two passive elements 2903 elements on device 2900 implanted within the IVC. System 3000 may differentiate the two passive elements in any of various ways, including through differences in their relative distance away, size, shape, patterns of fenestrations, echo-reflective coatings or other features. By a time-of-travel calculation, for example, the relative spacing of the two passive elements could be calculated. By measuring this distance many times per second, an accurate assessment of the variation in IVC dimensions could be made.

System 3000 may be programmed to look for the appropriate number of signals from the passive elements within the appropriate time period after it transmits a signal. This would minimize the risk of it tracking inappropriate signal reflections from other sources or anatomical structures such as the spine. In use, probe 3003 is held against the anterior abdomen and gently reoriented until it receives an effective echo from all of the passive elements. At this point system 3000 emits an audible signal, shows a green light, or uses other indicator means to confirm to the patient that the instrument is appropriately positioned. System 3000 may also include a strap around the patient's body that could be tightened to hold the device in place, or the patient could hold it in place manually, or use tape, adhesive, or other means to hold it in place while readings are taken.

In further alternative embodiments, instead of or accompanying passive elements, more active elements may be included with an implantable device such as device 2900. Such more active elements may comprise piezoelectric or other crystals which absorb incoming sonic signals and re-transmit these signals back to the receiver. Such embodiments may further comprise active elements powered by an externally delivered magnetic, electrical, or ultrasonic field. In such active embodiments, active marker elements, which may be also be schematically depicted by elements 2903 in FIG. 29, could then emit a signal that allows the external instrument to determine position more exactly. In further examples, each active marker element may include an inductance coil or other means to gather energy from a variable external electric or magnetic field; a capacitor or other means to store that energy; and then a piezoelectric crystal to emit an ultrasound signal, along with the appropriate circuitry to manage these elements. Such externally powered active marker elements need not be overly complex, firing an ultrasound signal whenever they are sufficiently charged or excited. Alternatively, the external system may send a triggering signal to tell each marker element when to fire, or to make them all fire simultaneously.

Figure 32:
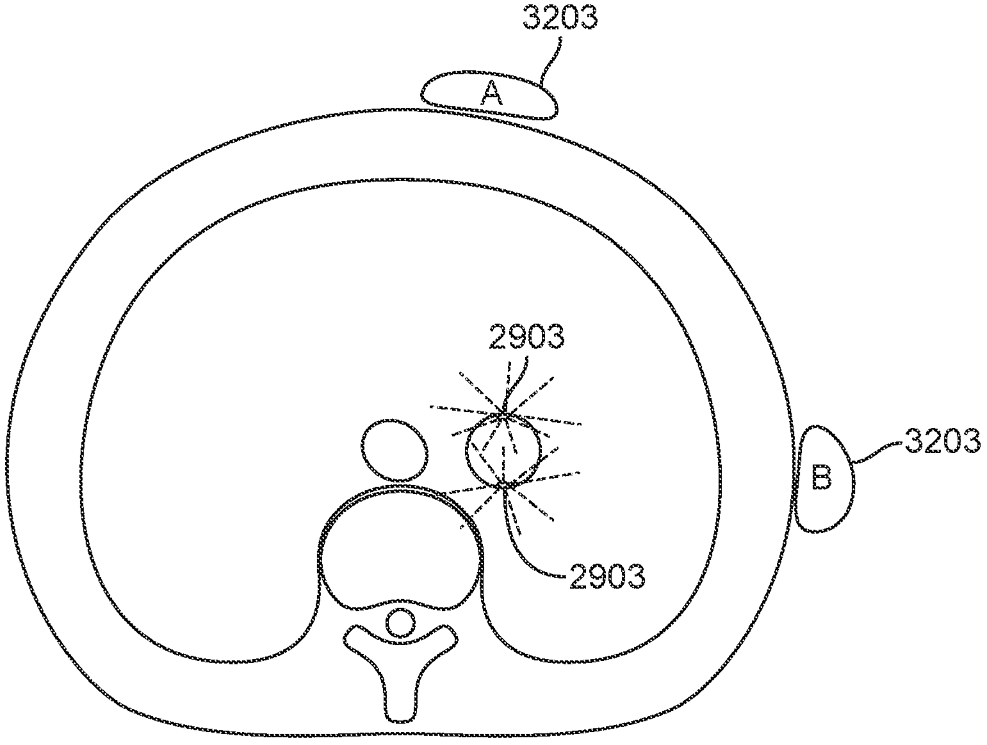
FIG. 32 schematically depicts an arrangement of markers and two sensors on a transverse cross-section of the body in a system according to one disclosed embodiment.

In embodiments employing active, ultrasound-emitting marker elements, one or more external ultrasound receivers may be arrayed on the body surface to detect the emitted signals. Again using time-of-travel calculations as will be appreciated by persons skilled in the art, the precise location of the active marker elements within the body could be determined. If the active marker elements fired simultaneously, then one ultrasound receiver located on the anterior abdominal wall could be enough to accurately measure the anterior-posterior dimension of the IVC. If they did not fire simultaneously, then more than one receiver may be necessary. The external sensors may be arrayed in a way that maximizes the precision of the anterior-posterior measurement. FIG. 32 shows a transverse cross-section of the body, and one arrangement of two external sensors 3203. The distance from implanted active marker elements 2903, within the IVC, to sensor 3203A on the patient's anterior abdomen will vary directly as the anterior-posterior (A-P) IVC dimensions change, while the distance from implanted active marker elements 2903 to sensor 3203B on the patient's side will change little. By analyzing the difference in the time it takes for ultrasound signal from each active marker element to reach sensor A versus sensor B, the A-P dimensions of the IVC can be calculated. As long as at least two sensors are used (for example, one on the anterior wall of the IVC and one on the posterior wall), their relative motion could be measured quite accurately, cancelling out other motions such as the rise and fall of the abdominal wall during respiration. Note that elements 2903 may also be implanted on an external surface of the IVC as depicted in the embodiment of FIGS. 28A-C, or may be passive elements if transducers are used instead of sensors 3203.

Other methods of determining position from passive or active marker elements also may be employed. For example, in one embodiment, the marker elements may comprise one or more small magnets implanted against the IVC wall using device embodiments described herein above, and a sensitive magnetometer could be used to detect the position and motion of the magnet(s). A SQUID magnetometer (Superconducting Quantum Interference Device) could be used to very sensitively measure the variation in location of an implanted magnet, although this device may require a cooling apparatus to bring even a high-temperature SQUID to a temperature where it becomes superconducting. Other types of magnetometers could also be used.

Figure 33:
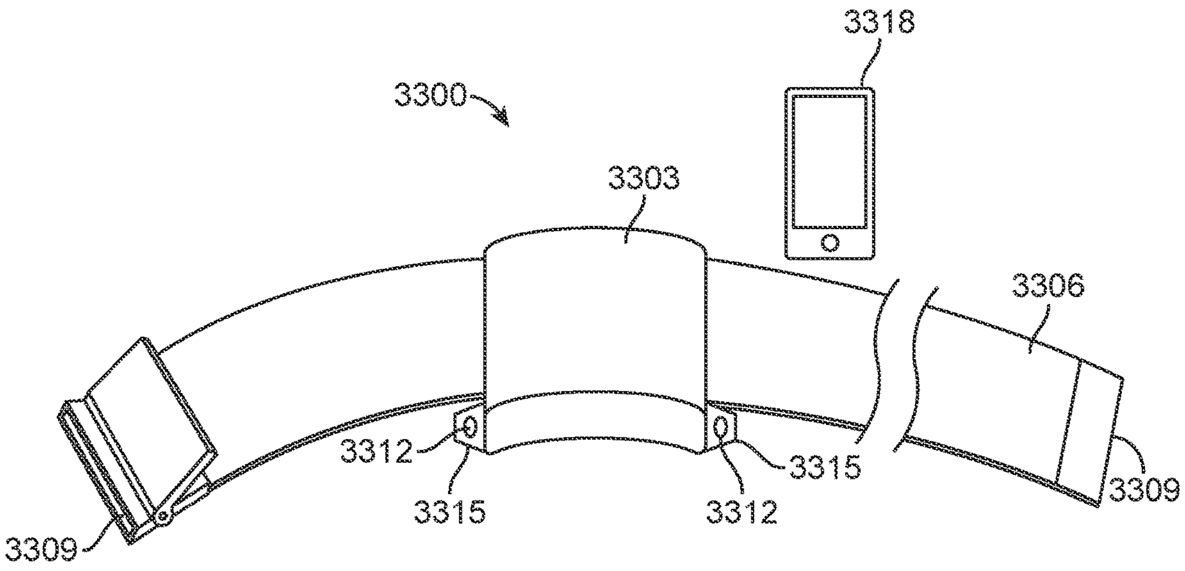
FIG. 33 schematically depicts another alternative embodiment of a system described in the present disclosure.

A further alternative embodiment may comprise the implantation of marker elements, such as containing ultrasound crystals, that show up very brightly on an ultrasound image. Automated image analysis software within the ultrasound system can then automatically detect marker element positions and record them. One embodiment of this approach would be to implant a stent with Nitinol arms that can be easily identified by an ultrasound imaging system using automated software. An implanted device similar to that shown in FIG. 29 could include a stent implanted caudal to the renal veins, and two or more metal arms that extend cranial to the renal veins. For example, one arm could be positioned along the anterior wall of the IVC and another along the posterior wall. A transverse cross-sectional ultrasound image of the IVC cranial to the renal veins will cross these arms, and they will show up as clear marks on the ultrasound image. Image-analysis software could then identify those marks, track them, and measure the variation in IVC dimensions automatically. To make these measurements consistent, the patient or caregiver could be trained to hold an ultrasound imaging transducer on the patient's abdomen in a specific location. Tattoos or other markings on the skin could be used to identify a consistent location from which measurements are to be taken. In one embodiment, as shown in FIG. 33, a wearable detection system 3300 includes ultrasound probe 3303 that may be fastened in place on the patient via strap 3306 and buckle 3309. Ultrasound probe 3303 may also include windows 3312 mounted on body contacting tabs 3315, or other indicators, that would be placed over or adjacent the location mark on the body to ensure proper location of probe 3303. Ultrasound probe 3303 may communicate wirelessly with an external device 3318, such as a cell phone, which controls the probe, displays the measured data, and transmits it to other systems or cell phones. Alternatively the ultrasound transducer could be shaped so that the transducer is reliably positioned a certain distance from various anatomical points, such as a distance from the bottom of the rib cage.

A further embodiment is a system that monitors IVC dimensions without implanted elements. For example, a portable, external ultrasound system could comprise a processor and software that analyzes a reasonably consistent ultrasound image of the abdomen to automatically identify the IVC. This software then automatically identifies the anterior and posterior walls of the IVC within that image, and continuously or periodically measures and records the variation in IVC dimensions over time. In such an embodiment, the system would include an emitter and receiver that can be secured to the patient, or that can be positioned at one or more marked locations on the patient's skin, so that measurements are taken from a consistent location. Preferably such a system is contained in a lightweight, compact housing, battery-powered, and small enough to be worn by the patient or easily held by the patient during measurements. System 3300 as shown in FIG. 33 may also be used in this embodiment.

As a further method of simplifying the identification of the IVC and appropriate positioning of the probe, a three-dimensional ultrasound map of most of the patient's abdomen can be stored in the ultrasound system's memory when the patient first begins using the system. From that point, optimal positioning of the probe and its two-dimensional slice within that three-dimensional volume can be defined. Then, when the patient is imaged in a subsequent measurement, the ultrasound system can compare the image to the three-dimensional map, determine where the image is relative to the desired slice, and indicate to the person doing the image to move the probe cranially, caudally, medially, or laterally to reach the optimal position.

In all of the above-mentioned marker element-based embodiments, external components of such systems are preferably configured to report the IVC dimensions to the patient, as well as wirelessly transmit that information to the patient's doctor or other people monitoring the patient's health. Since they are external to the body, size is less critical, and such components could have more significant batteries to allow communication with the physician or other monitors via a Bluetooth®, cellphone, or other communications modality as described in more detail later in this disclosure. The ultrasound receiving/transmitting element of any of these less-invasive IVC monitoring systems could be configured to be worn continuously by the patient, or it could be used for a period of minutes once or more per day. All of the external components maybe contained in a single housing, or could be broken up into two or more separate units. For example, in system 3000, shown in FIG. 30, ultrasound receiver/transmitter probe 3003 may be connected either wirelessly or by cable to console 3006 adapted to provide user control functions, perform calculations, store and display information, and communicate with cell phones or the Internet via wireless networks. Console 3006 may include a CPU, memory device, and other components for input, communication and storage as described in further detail below in connection with FIG. 46. In this way, a transmitter/receiver probe may be compact, lightweight and wearable (as in FIG. 33), while the control console could be a larger tabletop unit.

Injectable and Other Passive Marker Embodiments

Embodiments discussed above primarily encompass active marker element-based embodiments and more passive marker elements that may be fastened to the IVC wall by various embodiments of anchor elements or other similar suitable means. In further alternative embodiments, as described herein below, marker elements are placed or injected into or within the IVC wall. In some clinical situations, instead of a marker element that is fastened to the inner or outer wall of the IVC, such placement may be easier or preferable.

Figure 34A:
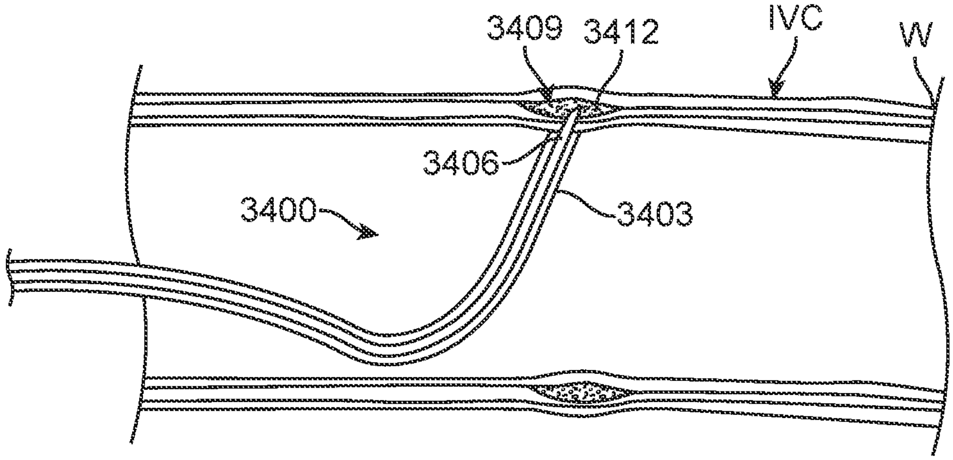
FIG. 34A illustrates placement or injection of a marker between the medial and adventitial layers of the wall of the IVC according to one exemplary embodiment disclosed herein.
Figure 34B:
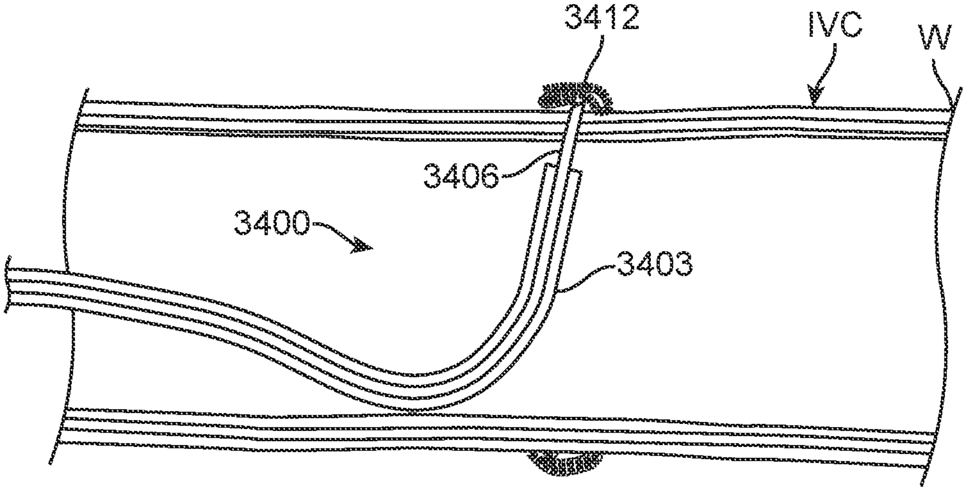
FIG. 34B illustrates delivery and adherence of a marker to the outer surface of the wall of the IVC in another exemplary embodiment disclosed herein.

In one such injectable-type embodiment, as shown in FIGS. 34A and 34B, a relatively small guiding catheter 3403 may be introduced into the IVC, and through that catheter a needle or blade 3406 may be introduced. Under ultrasound or fluoroscopic guidance, needle 3406 may be directed towards the appropriate wall of the IVC, and inserted into the wall. Needle/blade/catheter 3406 may have a shoulder or hilt a selected distance from its distal tip to engage the wall surface so as to limit the depth of penetration of the needle or blade. The needle or blade 3406 may be configured to create a pocket or flap in the IVC wall into which biocompatible or resorbable substance 3409 containing marker elements 3412 may be placed or injected. System 3400 may be further configured to deliver marker elements 3412 into the middle of the IVC wall, such as between the medial and adventitial layers of the IVC, or between the intimal and medial layers. System 3400 may also be configured to deliver marker elements 3412 through the thickness of the IVC wall to the exterior so that marker elements 3412 would adhere against the outer surface of the IVC as shown, for example, in FIG. 34B.

Injectable marker elements may be, for example, a flexible wire, ribbon, or guidewire segment, which could be advanced easily through a catheter or needle into or against the IVC wall. Such a marker element could be attached to a delivery wire or catheter, and removed or repositioned as needed. The marker element would only be detached from the delivery system once appropriate positioning had been confirmed. System 3500, shown in FIG. 35, uses coiled wire marker element 3503, which is deployed using delivery catheter 3506. Delivery catheter 3506 holds marker element 3503 with two jaws 3509 until the marker element reaches the distal end of the delivery catheter 3506, at which point the jaws separate to release the marker element. Marker element 3503 also may be released via a threaded connection, an interlocking mechanism, an electrolytic or other soluble connection, or other such release mechanisms as are known in the art.

Figure 36A:
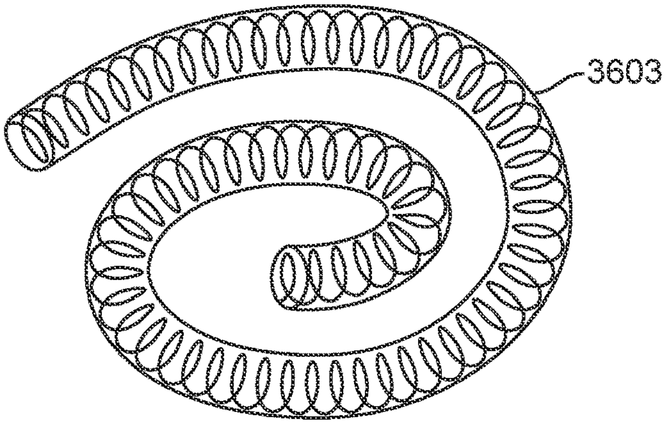
FIG. 36A illustrates an embodiment of a guidewire coil.
Figure 36B:
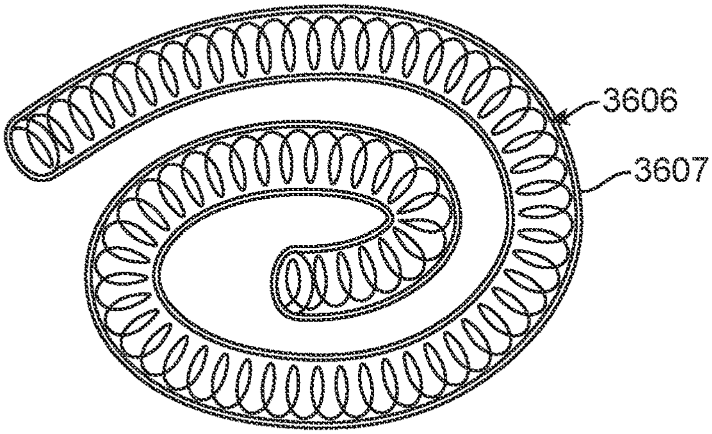
FIG. 36B illustrates a guidewire coil coated with a polymer to permanently entrap air to provide echo-reflective characteristics.
Figure 36C:
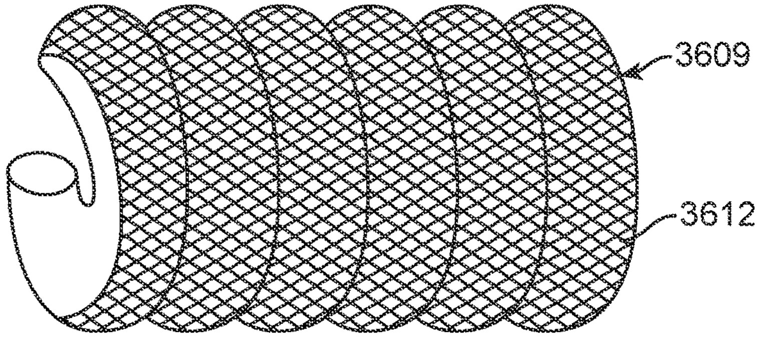
FIG. 36C is a close-up or enlarged view of a section of a coiled ribbon marker with surface texture configured to increase echo-reflectivity.
Figure 36D:
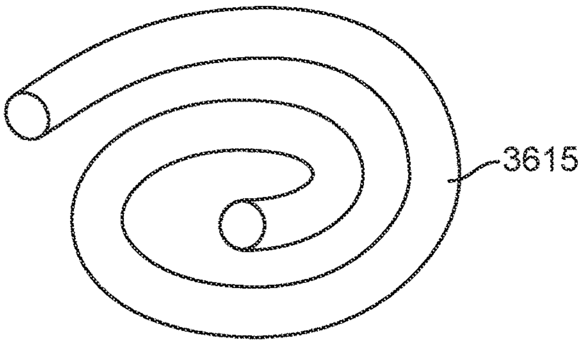
FIG. 36D illustrates another embodiment of a marker, which may comprise a simple echo-reflective tube such as a sealed tube of air.
Figure 36E:
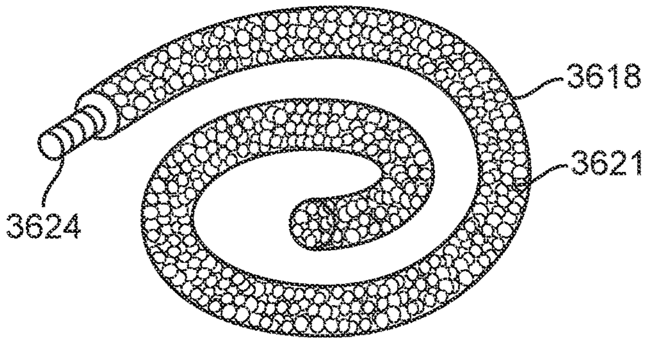
FIG. 36E illustrates another embodiment of a marker, in this case a tube of cast polymer such as silicone with echo-reflective gas bubbles embedded in the tube wall.

Examples of embodiments of guidewire segments for use in such injectable marker element embodiments are shown in FIGS. 36A-E. Such segments may have a surface texture optimized to reflect the ultrasound or other signal and may be metallic, such as platinum, titanium, gold, or other material, or it may be a polymer. A polymer embodiment may be molded with appropriate echo-reflective surfaces and radiopaque markings. Alternatively, such a guidewire marker element may comprise a section of hollow wire, sealed on each end and filled with air or echo-reflective fluid. A wire or ribbon may include barbs, scales, or other features to inhibit it from backing out of the IVC wall or migrating completely through the IVC wall. FIG. 36A shows a simple guidewire coil 3603. FIG. 36B shows a guidewire coil 3606 coated with polymer 3607 to permanently entrap air creating a highly echo-reflective marker. FIG. 36C shows a close-up of a coiled ribbon marker element 3609 with surface texture 3612 to enhance its echo-reflectivity. FIG. 36D shows marker element 3615 formed as a sealed tube of air. FIG. 36E shows marker element 3618, formed as a tube of cast polymer such as silicone which has been emulsified prior to curing, entrapping many tiny echo-reflective gas bubbles 3621. Gas bubbles 3621 can be of a particular gas to minimize any absorption through the walls of the polymer over time. Tubular or coil devices delivered through a catheter may be provided with a selectively releasable retention mechanism such that placement may first be confirmed before the device is released from the catheter. One such mechanism is illustrated in FIG. 36E, which includes threaded connector 3624 at one end, configured to cooperate with a threaded release mechanism in the delivery catheter. Once appropriate positioning has been confirmed, the delivery catheter may be unscrewed, leaving the polymer tube permanently in place.

Figure 37A:
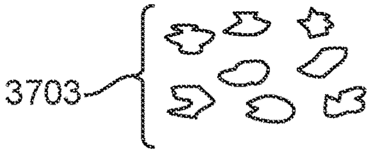
FIGS. 37A, 37B and 37C illustrate various embodiments of markers formed as particles in accordance with alternative embodiments disclosed herein.
Figure 37B:
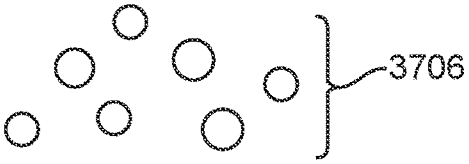
Figure 37C:
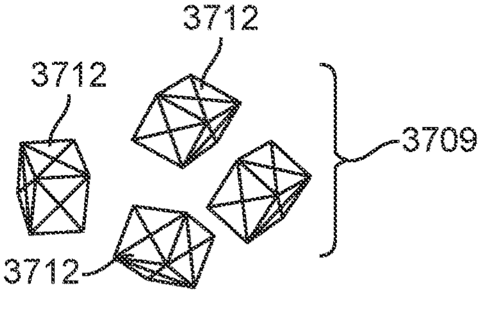

Alternatively, injectable marker elements may comprise a number of small echo-reflective beads or particles, as shown in FIGS. 37A-C, which may be injected into the wall of the IVC or into the peri-adventitial space against the outside of the IVC. Such injectable marker particles may comprise spheres of gas similar to commonly used air bubbles for temporary ultrasound imaging, except they would be encased in surrounding shells of a permanent or semi-permanent material such as silicone or other polymers. These bubbles form spherical reflectors for ultrasound signals. The injectable marker particles may alternatively be shaped with pyramidal indentations with 90 degree angles which will reflect signals very effectively, similar to radar reflectors used on sailboats. Injectable marker particles may be metallic, such as titanium, or they could be a polymer such as PEEK (polyetheretherketone).

FIG. 37A shows injectable marker particles 3703 with random jagged echo-reflective shapes. FIG. 37B shows hollow spherical injectable particles 3706. FIG. 37C shows alternative injectable marker particles 3709 with molded or shaped configurations having echo-reflective indentations 3712. Such injectable marker particles may be of any size from a few microns, to hundreds of microns, or the maximum size which will pass through the delivery catheter. The size might be particularly selected to maximize the reflection of signals of specific frequencies. Nanoparticle-based technologies also may be employed to provide such particles.

Figure 38:
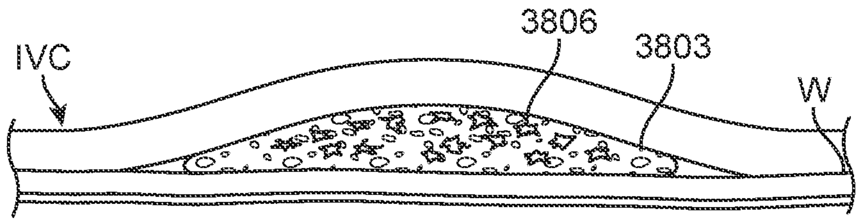
FIG. 38 is an enlarged view of a further exemplary embodiment of a marker as disclosed herein comprising a gel mixed with marker particles injected into the wall of the IVC.

During delivery, injectable marker particles as described above may be suspended in a fluid such as saline, or a gel such as certain formulations of polyethylene glycol (PEG). PEG is already used in vessel walls for vascular closure applications, such as the MYNXtm device from Access Closure. Depending upon their formulation, materials such as PEG can be resorbed over the course of weeks or months, leaving the marker particles permanently in place. Alternatively, a permanent polymer could be injected which can be injected as a liquid, but then hardens in place. This polymer may have marker particles suspended within it, or the polymer itself could be the marker. One example of a biocompatible polymer which could be used for this is urethane methacrylate. FIG. 38 shows a close-up of a urethane methacrylate gel 3803 mixed with marker particles 3806 injected into the wall W of the IVC.

Figure 39A:
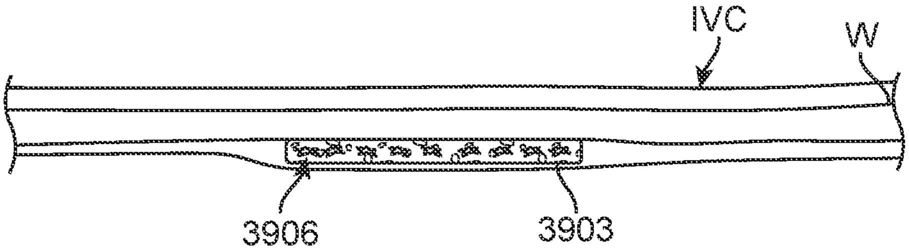
FIG. 39A is a cross-sectional view of a particle/marker containing patch endothelialized into the IVC wall.
Figure 39B:
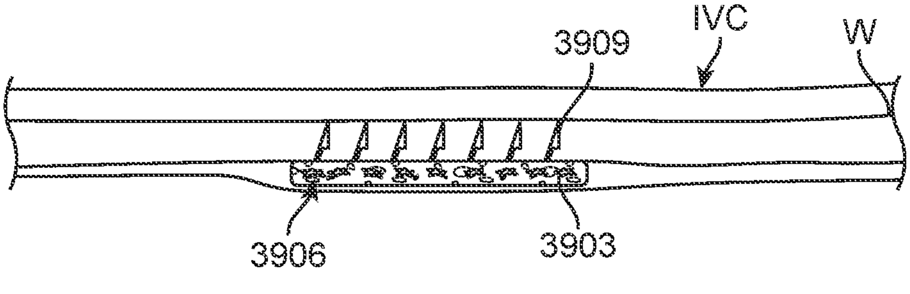
FIG. 39B is a cross-sectional view of an alternative marker patch utilizing a "Velcro-like" texture of microneedles or microhooks to adhere to and embed into the IVC wall.

Another alternative embodiment may comprise securing or sticking marker particles 3903 to the inner walls of the IVC with a material 3906 or texture that encourages the marker elements to grow into the IVC wall as shown, for example in FIGS. 39A and 39B. Fibrin is one example of a biocompatible material that is known to adhere to blood vessel walls, and to endothelialize in place. Other biocompatible, bioabsorbable adhesives could be used. Marker particles 3903 may be mixed into a fibrin patch and placed as desired in or against the IVC wall. After the patch is endothelialized and the fibrin absorbed, the marker particles remain in the vessel wall. FIG. 39A shows a cross-sectional view of patch 3906, containing marker particles 3903, which has endothelialized into the vessel wall, but patch 3906 itself has not yet been resorbed. Alternatively, a marker patch could be designed with a "Velcro-like" texture of microneedles or microhooks 3909 as shown in FIG. 39B, which embed into the IVC wall and may remain in place permanently.

Figure 40A:
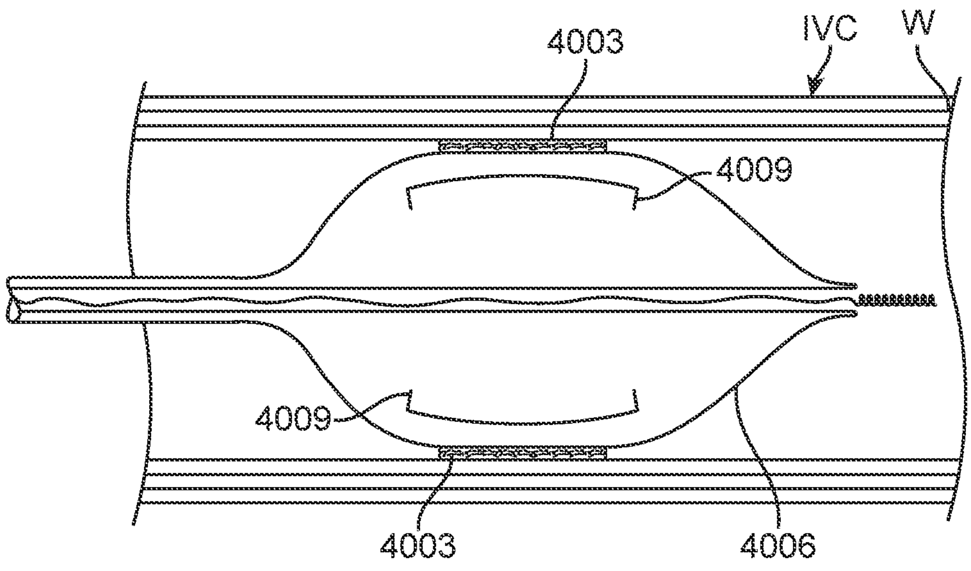
FIG. 40A illustrates balloon delivery of one or more markers in accordance with a further alternative embodiment disclosed herein.
Figure 40B:
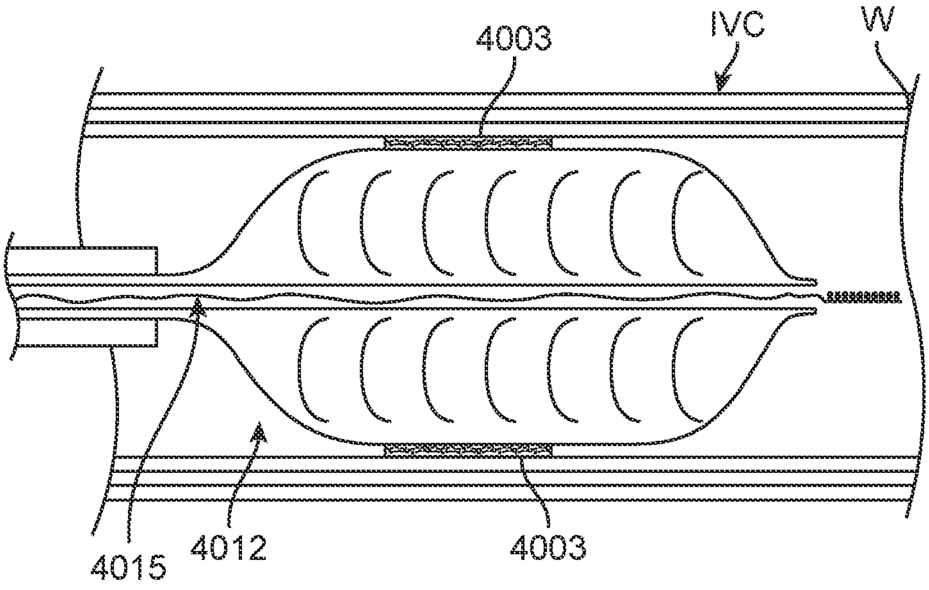
FIG. 40B illustrates another alternative embodiment in which a two-balloon catheter is used such that blood flow may be maintained during marker delivery and placement.

Marker elements 4003 designed to be applied to an inner surface of the IVC wall may be delivered to the IVC wall by mounting them on the outside of an inflatable balloon 4006, introducing that balloon into the IVC, and inflating it to press the marker elements against the IVC wall as shown in FIG. 40A. Marker elements 4003 may be relatively long and slender, to minimize the overall diameter of the combined marker elements and delivery system. Various marker elements described herein for adherence to or embedding in the IVC wall may be applied using this technique, such as, e.g., as shown in FIG. 39A or 39B. Before or during delivery, it will be important to confirm that marker elements 4003 are aligned with the anterior and posterior walls of the IVC, which may be accomplished, for example, by using radiopaque markers and fluoroscopy. Delivery balloon 4006 may have wings 4009 to cover marker elements 4003 during delivery, but which unfold or retract to expose the marker elements as the balloon is inflated. Alternatively, a cover sheath may be provided over the markers to hold them in place on the balloon during introduction. This cover sheath would then be withdrawn shortly before expansion of the balloon to deploy the markers. In a further alternative, two-balloon catheter 4012 may be used as shown in FIG. 40B, to permit blood flow through space 4015 so that blood flow would not be interrupted during the delivery process.

Sensing and position/measurement detection using injectable-type marker elements as described in the embodiments above may be accomplished by a variety of means or systems. For example, injectable marker elements may be designed to reflect ultrasound energy. Since the ultrasound signal is being used to measure distance rather than imaging, the signal may be provided at a relatively low power. Since the IVC is located deep in the abdomen, and higher-frequency signals attenuate rapidly in human tissue, it may be preferable to use a relatively low frequency, perhaps in the range of 200 KHz-2 MHz, although the frequency might be higher or lower in practice. The anterior-posterior dimension of the IVC could be measured simply by measuring the additional time it takes the signal to reflect off the posterior marker element and return to the system monitor, compared to the time it takes to reflect off the anterior marker element. Since the speed of sound in human soft tissue is approximately 1540 meters/second, if the A-P dimension of the IVC is approximately 20 mm in an average human patient, the posterior reflection will return to the monitor approximately 26 microseconds after the anterior reflection. Each additional millimeter of dimension will add approximately 1.3 microseconds to the differential.

It should be noted that one important measurement may be the percentage variation in that anterior-posterior dimension. Even if the absolute dimensional measurement is not accurate, the percentage variation should still be accurate. For example, if the monitor is 15 degrees to one side of the anterior-posterior alignment of the marker elements, the maximum measured absolute A-P dimension may be reduced by [one minus the cosine of 15 degrees], or 3.4%. But the minimum measured A-P dimension should be similarly reduced, so the overall percentage change should be minimal. Similarly, any movement of the abdominal wall, for instance with respiration, should not affect the differential in the time it takes for the two reflected signals to return to the system monitor.

Given the relatively low power needed for such a simple distance measurement, the monitor device may be of simple design and obtain a good signal even with a very low-power signal, which should maximize both the safety and battery life of the device. However, if more accurate distance measurements are desired, an external transmitter/receiver can be configured to provide consistent, precise measurement of the relative distance of the two marker elements. In one exemplary embodiment, shown in FIG. 41, external handset 4103 comprises two emitter/receiver pairs 4106 mounted a fixed distance apart on handle 4109. Each emitter/receiver pair 4106 is mounted on a contact pad 4712 configured to engage the patient's skin. Each emitter transmits a signal toward the implanted IVC markers, which reflect the signals back toward the handset for reception by the receivers. In this way the distance to each IVC marker may be calculated by triangulation to obtain a very precise measurement. Optionally, the two emitters can transmit signals at different frequencies to eliminate interference.

Multi-Sensor Monitoring Systems

While pulmonary artery (PA) pressure measurement mentioned in the Background above holds some promise as an approach to heart failure monitoring, it is believed that IVC volume measurement may present a more accurate and early indication of heart failure. However, the combination of IVC volume measurement with PA pressure monitoring may provide an even more comprehensive picture of disease progression.

The systems of the present disclosure may therefore include both an IVC volume monitor along with a PA pressure monitor, and/or other sensors for measuring symptoms related to heart failure. The multiple monitors/sensors may be coupled together by either a wired or wireless connections to allow data transmission between them, or they could operate completely independently. In preferred embodiments, the IVC monitor and the PA monitor will both communicate with a single data receiver outside the patient's body. Alternatively one of the monitors could transmit data to the other, from which it could be transmitted to an external receiver. Additionally, a power supply integrated into one of the two monitors could deliver power to the other of the monitors, or a separately implanted power supply could be connected to each monitor. The system could also include a controller/data analyzer that analyzed the data received from each monitor and used the combined data to determine the extent of or change in the patient's disease, and whether to set off an alarm or transmit a notification to the patient or health professional.

Figure 42:
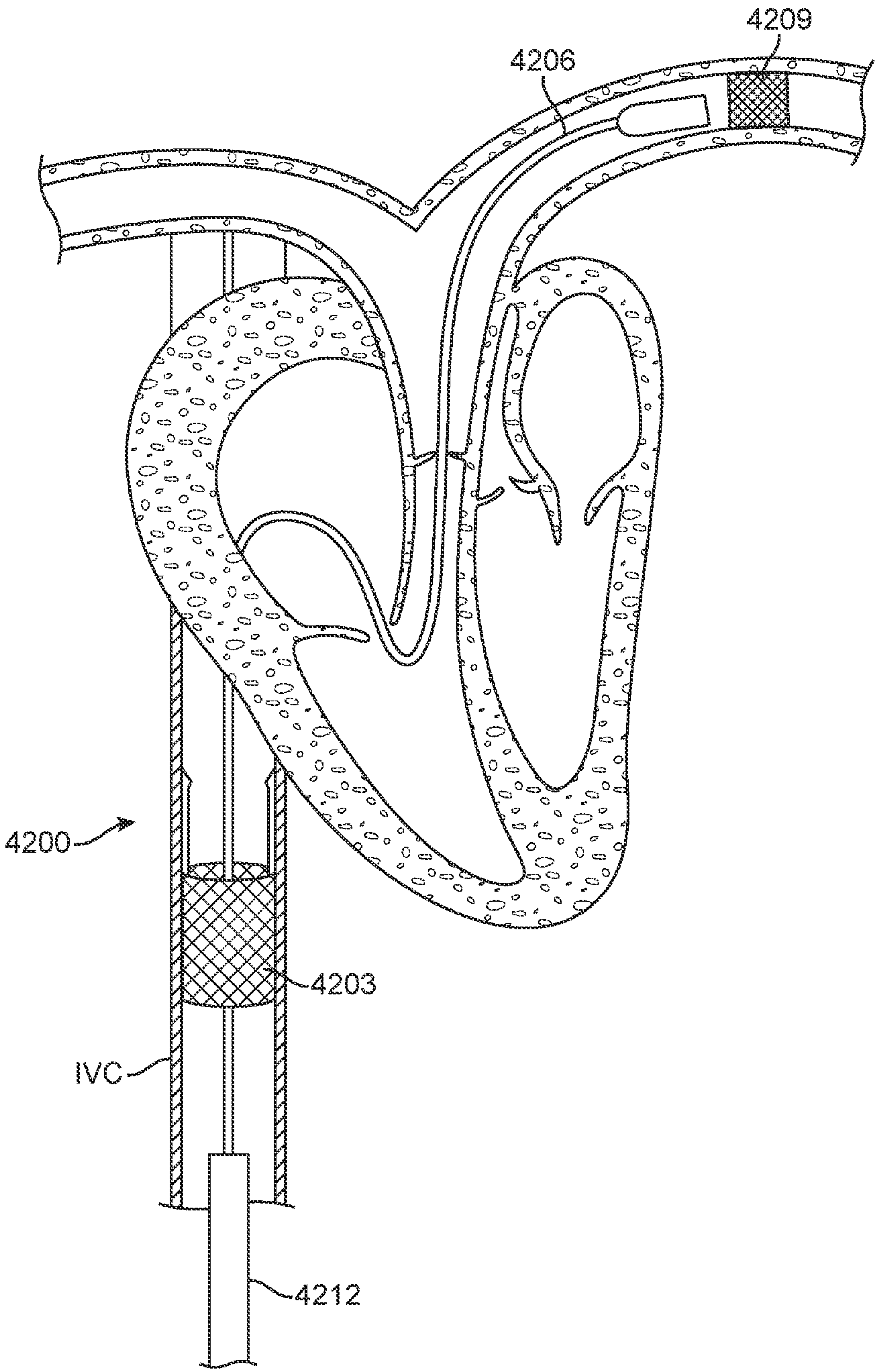
FIG. 42 schematically depicts another alternative system employing communicating monitoring and therapeutic devices.

One exemplary embodiment of such a system is system 4200, shown in FIG. 42. System 4200 may include a first delivery catheter (not shown) for implanting IVC volume monitoring device 4203 in the IVC, and second delivery catheter 4206 for implanting pressure sensor 4209 in the pulmonary artery. Each of these catheters could be introduced through a single introducer 4212 positioned in a peripheral vein such as a femoral or iliac vein. Alternatively, system 4200 may utilize a single delivery catheter carrying both IVC monitor 4203 and PA pressure monitor 4209. A single catheter arrangement allows monitoring of implants to be delivered serially (either PA first or IVC first) from a single catheter in a single intervention. Other sensors that could be included in a multi-sensor system such as system 4200, to provide additional data related to heart failure include a respiratory rate monitor, cardiac rhythm monitor, arterial or venous blood pressure monitor, blood oxygen saturation sensor, or cardiac output monitor.

Closed-Loop Therapy System Embodiments

This disclosure has heretofore described various embodiments, devices and methods for using the size, relative size, and variation in size of the IVC to detect the early onset of acute decompensation in heart failure. With the information provided by these devices and methods, various actions may be taken by patients, caregivers and physicians to diagnose or treat the disease. In still further embodiments, the IVC monitoring system may be expanded to provide for closed-loop control of a number of different therapeutic interventional systems. By sensing the onset of an event of acute heart failure decompensation and then triggering an intervention that may reverse, minimize or eliminate the episode of decompensation, significant suffering or death of the patient potentially may be avoided, and the health care system will save significant financial and human resources.

It is common practice to use intravenous (IV) diuretics to increase fluid output for patients who are admitted to the hospital for acute heart failure decompensation. Many patients in heart failure take oral diuretics, but as their heart failure status deteriorates, diuretics can become less and less effective when delivered orally. Intravenous or intramuscular diuretic delivery remains more effective in these situations. The output from the sensor/monitor contemplated herein could be coupled with IV pumps, for example, to control the dosage of IV diuretics in the in-patient setting. In this example, the sensor/monitor would communicate to an external module, increasing or decreasing dosage of the IV diuretics as necessary to maintain a desired IVC status. The external communication module could be a separate module, which in turn communicates to the IV pump, or it could be incorporated into the IV pump directly. Even if the physician preferred to manually set the initial infusion rate for the drug, the feedback system here could serve as an additional safety shut-off, interrupting delivery of diuretics once the IVC status reaches the appropriate level.

Also in clinical practice or in development are wearable or fully implantable pumps that can deliver IV or subcutaneous diuretics. To date these have been open-loop or uncontrolled systems. For example, Zatarain-Nicolas et al. reported a series of patients who were implanted with simple, passive constant-flow elastomeric subcutaneous pumps to deliver furosemide (a common diuretic) over time. The sensors discussed herein could be configured to communicate with a valved version of this type of pump to create a simple closed-loop system and to deliver subcutaneous diuretics.

Alternatively, fully implantable, refillable drug pumps, for example the Medtronic SynchroMed pump, are currently used to deliver pain medications. A fully implantable pump could be configured to communicate with the IVC sensors and deliver IV or subcutaneous diuretics. In one configuration, an implantable pump could be implanted in an infraclavicular pouch and the IVC sensor could be introduced into the IVC from the subclavian vein adjacent to the pouch. A lead could connect the two elements of the system, so that the pump uses the data from the IVC sensor to help determine whether to infuse the drug, and how much drug to deliver. The pump could deliver the drug into the infraclavicular pouch, into nearby muscle tissue, or it could deliver the drug directly into the vascular system. If it were delivering the drug directly into the vascular system, the infusion lumen from the pump to the vascular system might be integral with the lead from the IVC sensor, or it might be introduced parallel to it. The infusion lumen might be designed with a valve at the distal tip, to minimize the incidence of clotting or clogging that might block drug delivery.

Another class of drugs commonly used to treat heart failure are inotropes. Inotropes change the force of muscular contractions. In each of the embodiments described herein, diuretics could be exchanged for, or used in conjunction with, inotropic drugs. For example, dual chamber drug pumps configured to deliver both diuretic drugs and inotropic drugs could be configured to act upon the data generated by and communicated from the sensors described herein.

In addition to directly administering diuretics to the body, drug pumps and electrical neuromodulation systems have been contemplated for the control of heart failure by directly modulating the activity of the renal nerves. The renal nerves directly influence the renin angiotensin system and modulate fluid retention or excretion. The IVC sensors herein could be configured to communicate with drug pumps or neuromodulation systems to up- or down-regulate the activity of the renal nerves, thus increasing or decreasing the actions of the renin angiotensin system.

It should be noted that the renin angiotensin system also has regulatory effects on other aspects of heart failure decompensation. Notably, the peripheral vascular system, specifically vascular tone, is involved in heart failure status. The modulatory effects of the closed-loop systems described herein may also act directly on the systems that control vascular tone, such as the renin angiotensin system.

It was described above that the IVC sensor could be configured to communicate with an external IV pump. Similarly, the sensor data can be used to control other external devices to effect a therapeutic outcome. For example, the external data collection systems described in earlier open-loop IVC sensor systems could be configured to contain as part of that external system an automatic drug injection device similar to an EpiPen. In one embodiment the external data reader can be held in contact with the body while the data from the IVC sensor is transmitted. If the data shows that an intervention is required, the external system containing one or more automatic injection systems could deploy as a result of the collected data, injecting for example subcutaneous furosemide.

Figure 43:
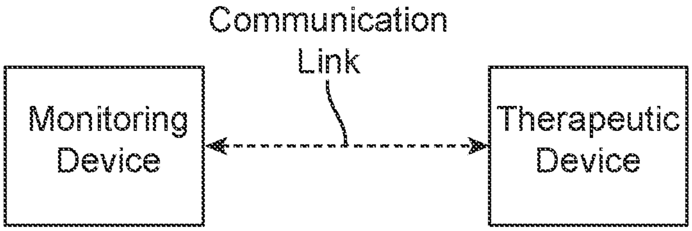
FIG. 43 schematically depicts a further alternative system employing direct communication through the IVC wall.

FIG. 43 presents a high-level schematic of such closed-loop system embodiments, which may include an IVC monitoring device (passive or active as described above) and at least one interventional treatment device, wherein the devices are configured to communicate with one another. The IVC monitor and the therapeutic device may communicate as necessary to coordinate sensed physiologic data and required intervention in a number of ways. Any of the typically used communication protocols may be used, including but not limited to Bluetooth protocol, RF communication link, microwave communication link, ultrasound communication or the like as further described below.

Figure 44:
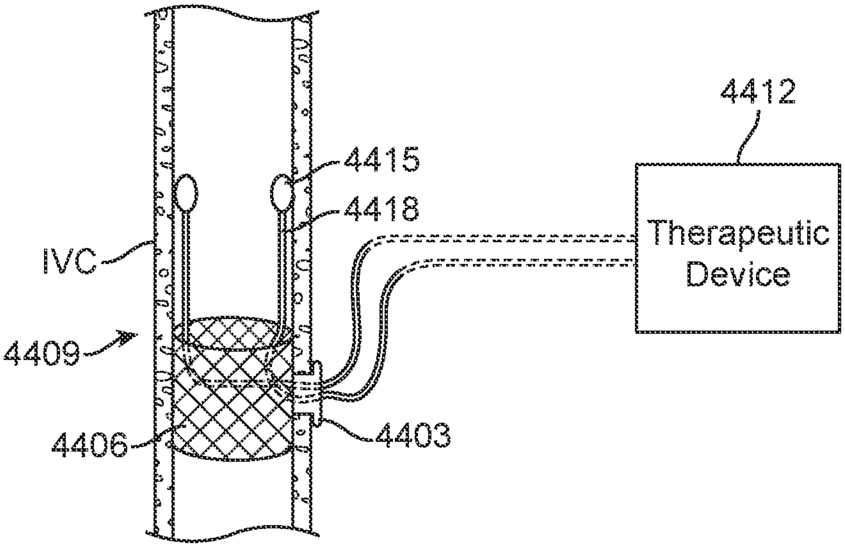
FIG. 44 schematically depicts yet another alternative system employing intravascular leads for direct communication.

In one embodiment, a direct communication can be made through the wall of the IVC proximate to, or posterior to the main body of the IVC sensor as shown in FIG. 44. This direct communication through the wall of the IVC may, for example, take the form of a mechanical grommet 4403 extending laterally from a side wall of anchor element 4406 of monitoring device 4409. Grommet 4404 is configured to pass through a penetration in the IVC wall. The grommet attachment can serve a dual purpose of helping anchor the sensor to the IVC and providing a wired communication port to the therapeutic device 4412. Grommet 4403 may be configured to seal with the IVC wall around its periphery, either mechanically and/or via an induced healing response, and may include a flange on its outer end to seal against the exterior surface of the IVC. Alternatively, a purse-string suture can be used to seal the vessel wall around the leads. A further alternative would be to locate the IVC sensor(s) on the outside of the IVC, for example as in the embodiment shown in FIG. 28B. If the therapeutic device is also outside the vascular system, then no transmural link is necessary. Note that monitoring device 4409 utilizes marker elements 4415 connected to anchor element 4406 via anchor isolation structure 4418.

Figure 45:
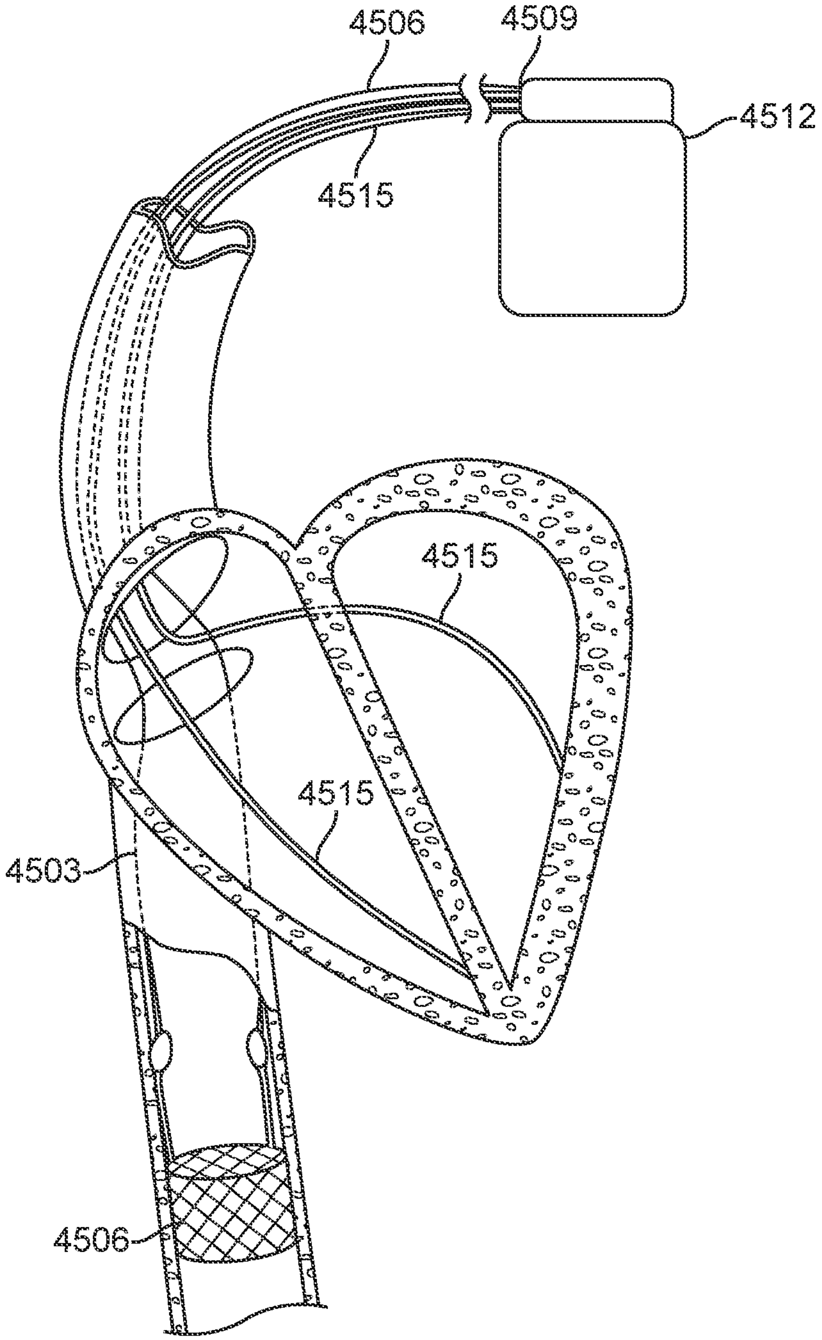
FIG. 45 illustrates one exemplary embodiment of a pulmonary artery sensor being implanted by a delivery catheter in the pulmonary artery following implantation of an IVC monitoring device in the IVC.

In another alternative, exemplified by the embodiment shown in FIG. 45, wired communication occurs via leads which run intravascularly to allow the IVC sensor to connect directly to the therapeutic device. For example, leads 4503 from IVC monitor 4506 can connect directly to dedicated ports 4509 of the therapeutic device 4512 (for example a pacing device such as a biventricular pacemaker). Inputs from IVC monitor 4506 can be programmed into the algorithm of the therapeutic device. For example, the inputs can be programmed into the biventricular pacing algorithm of a biventricular pacemaker to fine tune the coordination of the pacing of the heart. Since biventricular pacers are typically placed in an infraclavicular pouch with pacing leads 4515 introduced into the subclavian vein and advanced into the heart, the IVC monitor(s) could also be introduced into the subclavian vein on a delivery catheter and advanced into the IVC using techniques described above. This example could be incorporated to modulate the action of any of the therapeutic devices described below.

As an alternative to working directly with the therapeutic device by feeding the IVC sensor data into the device to modify a treatment algorithm, a separate lead (or a wireless signal) emanating from the sensor to modify the actions of a therapeutic device may be used. For example, the leads emanating from an IVC sensor could be placed in a position in which the signal from the sensor device can interact with the signal of a therapeutic device such that the signal from the sensor modifies the action of the therapeutic device. More specifically, a lead from a sensor can be placed in proximity to a lead from a pacing device such that a signal from the sensor causes a signal to emit from the sensor leads to interfere with or to augment the signal from the therapeutic device.

Embodiments of the interference mode of action described above may include placing a lead from the sensor alongside a lead from a pacemaker or biventricular pacemaker such that the signal from the sensor cancels out the signal from the pacer, or conversely augments the signal from the pacer to modify or modulate the therapy delivered. This example could be incorporated to modulate the action of any of the therapeutic devices described below. The integration of sensor data into a closed-loop system may be accomplished with many different therapeutic devices and methods currently marketed or in development for the treatment of heart failure and its associated comorbidities.

Closed-Loop Systems with Spinal Cord Stimulation

Spinal Cord Stimulation (SCS) has been tested to treat heart failure by modulating the balance of sympathetic and parasympathetic activity in the body. This typically involves the surgical implantation of an implantable pulse generator (IPG) or neurostimulator, with electrodes which are placed near the spinal cord to deliver a series of low-energy electrical impulses. The IPG is typically implanted in the abdomen near the spine.

It may be appropriate to adjust the delivery, frequency, or intensity of these electrical impulses to match the severity of the patient's heart failure status. Therefore, it may be appropriate to link the IVC monitor and the SCS into a closed-loop system. Since the IPG is very close to the IVC near the posterior wall of the abdomen, it may be appropriate to surgically implant sensors in the IVC which are connected via leads directly to the IPG. Alternatively, wireless markers could be implanted in the IVC and the IPG could wirelessly sense the distance of the markers to determine the volume status of the patient, similar to the previously described external monitoring device.

The healthcare provider could then program this closed-loop system based on an algorithm which might have the SCS impulses turned down or completely off when the patient's status is relatively healthy, with increasing intensity of SCS impulses if the patient's condition deteriorated. This system could also integrate additional physiologic information such as heart rate, respiration rate, physical activity, etc. into its calculations. It could also wirelessly communicate with external devices, which communicate the patient's and system's status to the patient, a physician, or other caregiver.

One exemplary application of this device would be to monitor the heart failure status of patients with chronic heart failure. It may very sensitively measure a patient's trend toward fluid overload, and may do so well in advance of an episode of acute decompensated heart failure. This would give the patient, physician, nurse, or other caregiver time to adjust fluid intake, increase diuretic medications or take other steps to reduce the patient's fluid status. The external module might include an alarm which tells the patient to get out of bed and sleep more upright or to go directly to the hospital, if the perceived risk of fluid overload is extremely high.

Another exemplary application of disclosed devices is to manage a patient during an episode of hospitalization for acute decompensated heart failure. Even though a patient may spend several days in the hospital receiving intravenous diuretics, reduced fluid intake, and even aquapheresis (dialysis to reduce fluid volume), it is quite possible that the patient leaves the hospital with excess fluid. In these situations, embodiments described may be usefully applied to titrate the diuresis process and to assess when the patient should be discharged. Further, as this new parameter of IVC distention and variability is studied more extensively based on the teachings of the present disclosure, it may prove to be an important prognostic indicator for a number of other conditions and situations other than management of heart failure, dialysis, and patients in shock.

As noted in connection with various embodiments described herein, one or more aspects and embodiments may be conveniently implemented using one or more machines (e.g., one or more computing devices that are utilized as a user computing device for electronic medical information or documents, one or more server devices, etc.) programmed according to the teachings of the present disclosure, as will be apparent to those of ordinary skill in the art.

This device may have electronic circuitry that stores data which may then be communicated to an outside monitor via a telemetry system. This information could then be further processed for presentation to the patient, giving a simple indication of their risk level or recommended level of drug intake, or diet and activity recommendations. This information could also be forwarded to the patient's physician, so that they can monitor the patient's condition and communicate with the patient as appropriate.

This information could also be forwarded via the internet or other means to the company which manufactures or sells the device, so that the company can continue to optimize the algorithms which use the raw data to determine the patient's risk level. It may be most effective to have the external monitor forward all of the raw data to the company, since the company will have the most up-to-date and optimized algorithms for analyzing data, and then send the processed information back to the patient and their physician. The company might also have the most secure data storage means for storing all historical information for each specific patient, so that the data analysis algorithm can be further optimized for each specific patient.

Embodiments disclosed herein may also be used for measuring dimensions of other body elements besides the IVC. Sensors could be placed in the heart, for example placing them in the left ventricle via catheter-based delivery. They could also be placed on the surface of the heart, within the pericardium via a subxyphoid access. These sensors could be used to directly monitor the heart's activity. As another example, sensors could be placed on or in the bladder to monitor bladder conditions. In patients who need to self-catheterize to drain their bladders, it may be useful to have an automated warning of when the bladder was full.

For all of the above-mentioned embodiments that have markers or sensors implanted into the IVC, these markers or sensors may heal into the IVC wall over time. Therefore, the stent, anchor, or other elements that hold the markers in place may not need to be permanent. Therefore, it may be desirable to make the stent or anchor bioerodable, so that after a period of time, there is no longer a stent in the IVC. The specific duration of the anchoring elements can be varied from weeks to years through material selection, formulation, and processing. This would eliminate a foreign body, and it would also render the IVC more flexible, allowing it to more naturally collapse or expand. Other bioabsorbable vascular elements have already been made from materials such as Poly-L-Lactide. These materials have less springiness than Nitinol, so the stent design may need to be modified. For example, the stent could be made with circumferential elements that ratchet open to apply pressure to the IVC to hold the stent in place. The delivery catheter for this bioabsorbable stent might include a balloon to actively expand the stent against the IVC.

Embodiments described in this disclosure so far have focused primarily on volume changes in the IVC. As the patient inhales, thoracic pressure drops slightly, increasing the flow of blood from the IVC into the right atrium (RA). As the patient exhales, thoracic pressure increases slightly, decreasing the flow of blood into the right atrium. This leads to a variation in blood volume in the IVC over the respiratory cycle. This variation in blood volume is necessarily correlated with a slight variation in the relative pressure between the IVC and the RA. As an alternative or adjunct to IVC volume measurement, a measurement of the relative variation in fluid pressure between the IVC and right atrium may provide a useful indication of blood volume. An implant with two pressure sensors arrayed along a single lead could be implanted from the femoral vein, jugular vein, or subclavian vein and anchored in position so that one pressure sensor is in the RA and one in the IVC. Embodiments described above having different configurations for IVC monitors (wireless, externally powered, powered by electronics deployed within the IVC or RA, powered from an infraclavicular implant, etc.) may alternatively or additionally employ such a measurement of relative variation in fluid pressure.

System and, Control and Communication Hardware and Software Aspects of Disclosed Embodiments Appropriate software coding can readily be prepared by skilled programmers based on the teachings of the present disclosure, as will be apparent to those of ordinary skill in the software arts. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 18:
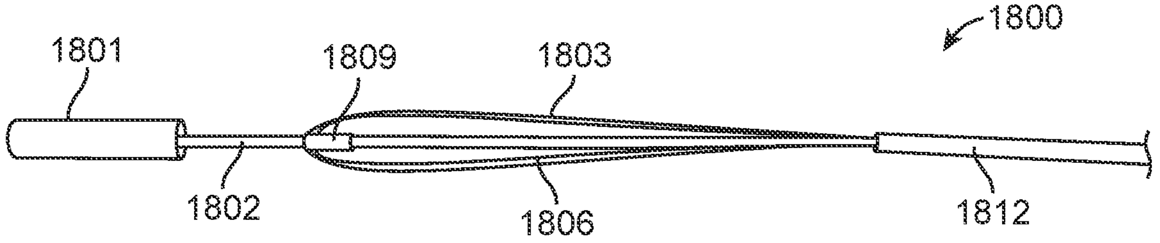
FIGS. 18 and 19 are perspective views illustrating a further embodiment of an anchor element shown in the collapsed and expanded/deployed configurations, respectively.
Figure 19:
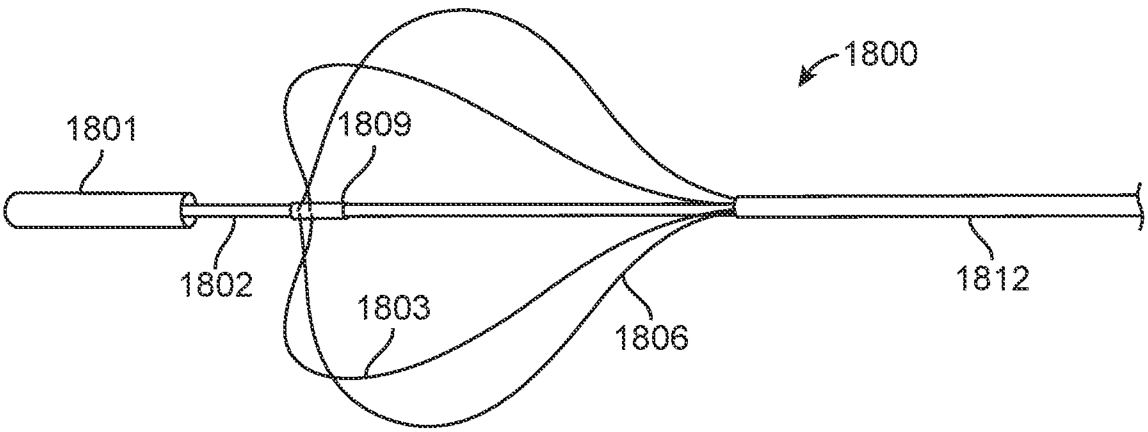
Figure 41:
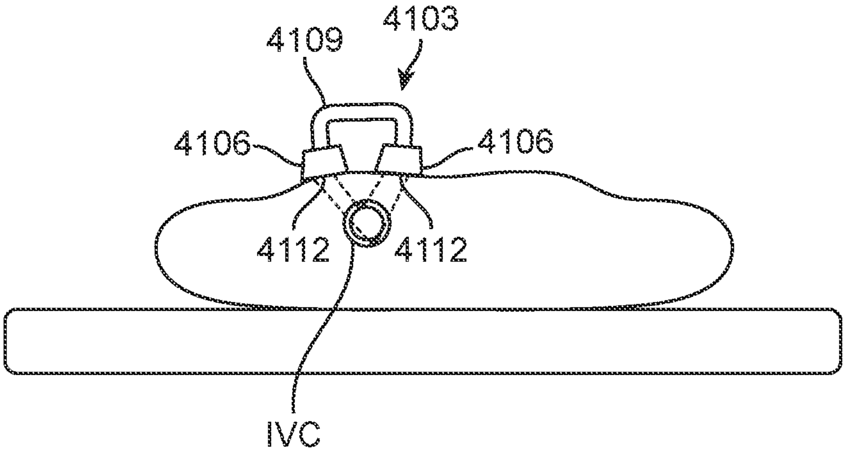
FIG. 41 illustrates an exemplary embodiment of an external transmitter/receiver configured to provide more consistent and precise measurements of relative distance between IVC two markers as described herein.
Figure 46:
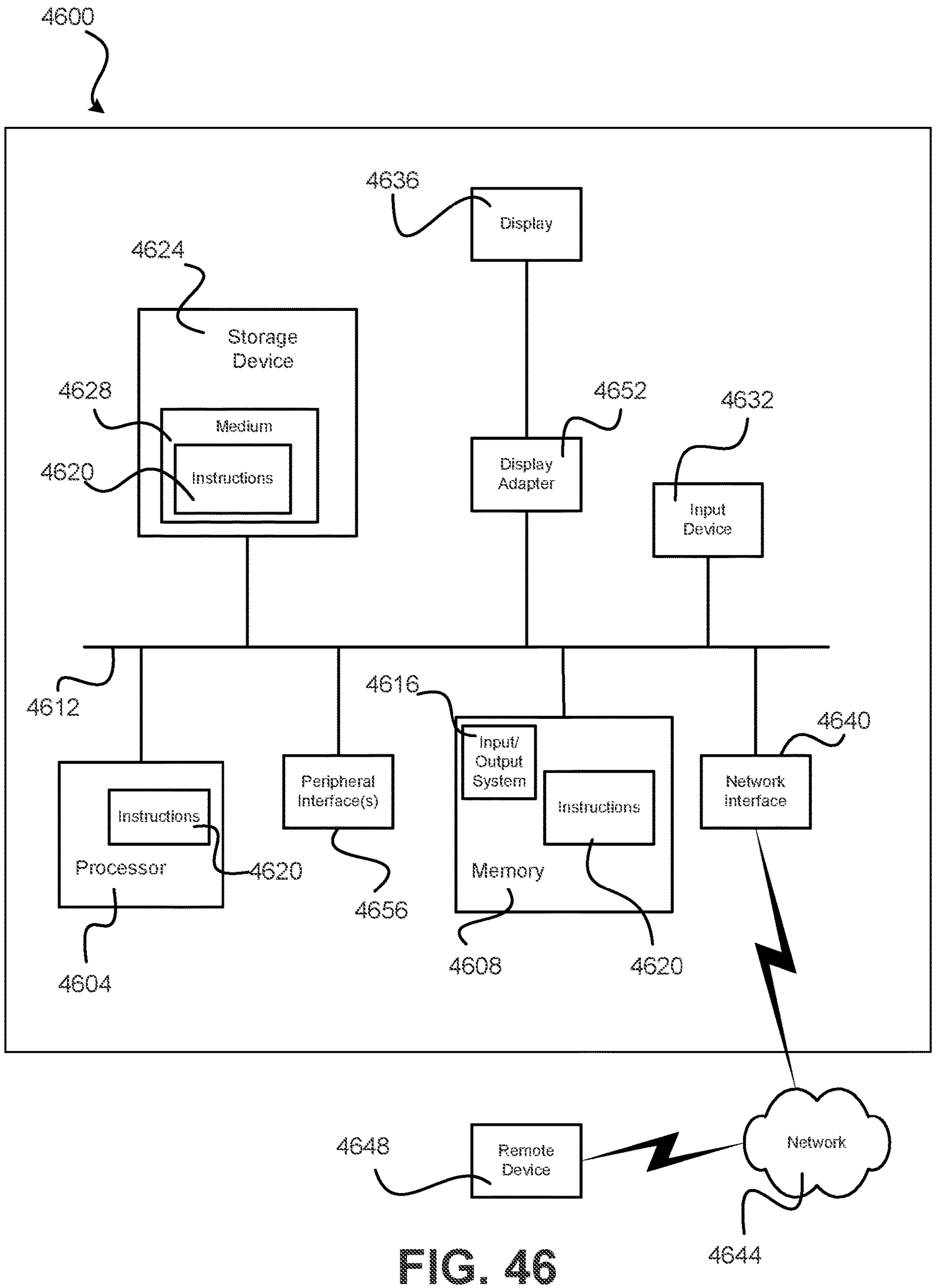
FIG. 46 is a block diagram illustrating embodiments for communication and computerized implementation of various embodiments described herein.
Figure 47:
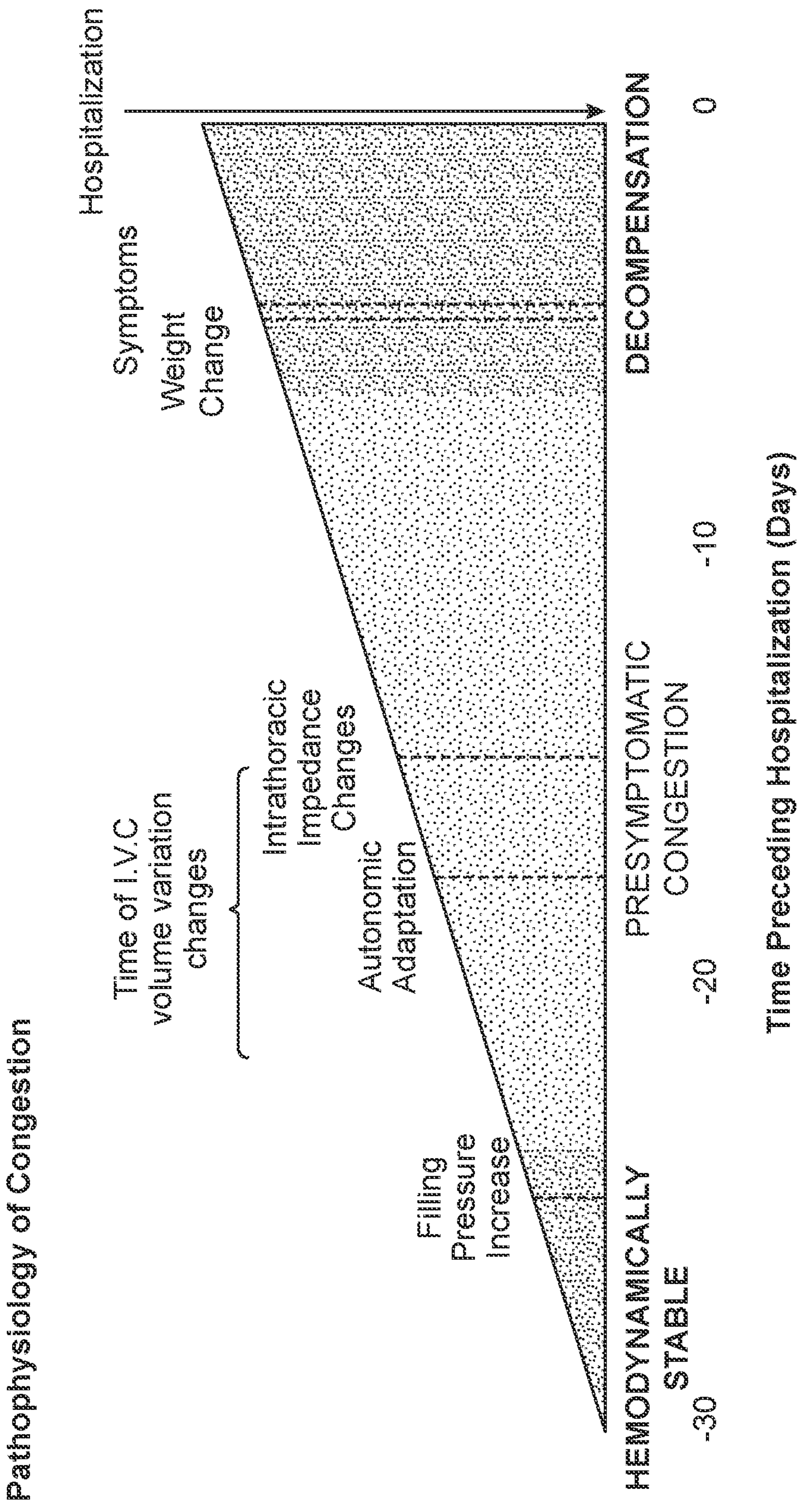
FIG. 47 illustrates a typical timeline of symptoms leading to hospitalization for ADHF.

FIG. 46 shows a diagrammatic representation of one embodiment of a computing device in the exemplary form of a computer system 4600 within which a set of instructions for causing a control system to perform any one or more of the aspects and/or methodologies of the present disclosure may be executed, such as a control system that may be embodied by or implemented in accordance with one or more components of: any one or more of the IVC sensors and/or monitors and/or associated components disclosed herein; electronics capsule 118 of FIG. 1; electronics capsule 503 of FIG. 5; electronics capsule 1124 of FIG. 11; electronics capsule 1701 of FIG. 17; electronics capsule 1801 of FIG. 18; electronics capsule 2306 of FIG. 23; electronics capsule 2512 of FIG. 25; electronics capsule 2806 of FIG. 28A-C; console 3006 and/or ultrasound receiver/transmitter probe 3003 of FIG. 30; wearable detection system 3300 and/or external device 3318 of FIG. 33; external handset 4103 of FIG. 41; system 4200 of FIG. 42; one or more components of the systems of FIGS. 43 and/or 44; and/or IVC monitor 4506 of FIG. 45, among others. It is also contemplated that multiple computing devices may be utilized to implement a specially configured set of instructions for causing one or more of the devices to perform any one or more of the aspects and/or methodologies of the present disclosure. Computer system 4600 includes a processor 4604 and a memory 4608 that communicate with each other, and with other components, via a bus 4612. Bus 4612 may include any of several types of bus structures including, but not limited to, a memory bus, a memory controller, a peripheral bus, a local bus, and any combinations thereof, using any of a variety of bus architectures.

Memory 4608 may include various components (e.g., machine-readable media) including, but not limited to, a random access memory component, a read only component, and any combinations thereof. In one example, a basic input/output system 4616 (BIOS), including basic routines that help to transfer information between elements within computer system 4600, such as during start-up, may be stored in memory 4608. Memory 4608 may also include (e.g., stored on one or more machine-readable media) instructions (e.g., software) 4620 embodying any one or more of the aspects and/or methodologies of the present disclosure. In another example, memory 4608 may further include any number of program modules including, but not limited to, an operating system, one or more application programs, other program modules, program data, and any combinations thereof.

Computer system 4600 may also include a storage device 4624. Examples of a storage device (e.g., storage device 4624) include, but are not limited to, a hard disk drive, a magnetic disk drive, an optical disc drive in combination with an optical medium, a solid-state memory device, and any combinations thereof. Storage device 4624 may be connected to bus 4612 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 4624 (or one or more components thereof) may be removably interfaced with computer system 4600 (e.g., via an external port connector (not shown)). Particularly, storage device 4624 and an associated machine-readable medium 4628 may provide nonvolatile and/or volatile storage of machine-readable instructions, data structures, program modules, and/or other data for computer system 4600. In one example, software 4620 may reside, completely or partially, within machine-readable medium 4628. In another example, software 4620 may reside, completely or partially, within processor 4604.

Computer system 4600 may also include an input device 4632. In one example, a user of computer system 4600 may enter commands and/or other information into computer system 4600 via input device 4632. Examples of an input device 4632 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 4632 may be interfaced to bus 4612 via any of a variety of interfaces (not shown) including, but not limited to, a serial interface, a parallel interface, a game port, a USB interface, a FIREWIRE interface, a direct interface to bus 4612, and any combinations thereof. Input device 4632 may include a touch screen interface that may be a part of or separate from display 4636, discussed further below. Input device 4632 may be utilized as a user selection device for selecting one or more graphical representations in a graphical interface as described above.

A user may also input commands and/or other information to computer system 4600 via storage device 4624 (e.g., a removable disk drive, a flash drive, etc.) and/or network interface device 4640. A network interface device, such as network interface device 4640, may be utilized for connecting computer system 4600 to one or more of a variety of networks, such as network 4644, and one or more remote devices 4648 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 4644, may employ a wired and/or a wireless mode of communication. In general, any network topology may be used. Information (e.g., data, software 4620, etc.) may be communicated to and/or from computer system 4600 via network interface device 4640. In some embodiments, one or more cloud computing services, "software as a service" services, "storage as a service" services, and/or distributed networks or components, among others, may be used to receive, store, and/or provide data and/or execute software in accordance with aspects of the present disclosure, as will be understood by those of ordinary skill in the relevant art after reading this disclosure in its entirety.

Computer system 4600 may further include a video display adapter 4652 for communicating a displayable image to a display device, such as display device 4636. Examples of a display device include, but are not limited to, a liquid crystal display (LCD), a cathode ray tube (CRT), a plasma display, a light emitting diode (LED) display, and any combinations thereof. Display adapter 4652 and display device 4636 may be utilized in combination with processor 4604 to provide graphical representations of aspects of the present disclosure. In addition to a display device, computer system 4600 may include one or more other peripheral output devices including, but not limited to, an audio speaker, a printer, and any combinations thereof. Such peripheral output devices may be connected to bus 4612 via a peripheral interface 4656. Examples of a peripheral interface include, but are not limited to, a serial port, a USB connection, a FIREWIRE connection, a parallel connection, and any combinations thereof.

Device embodiments disclosed herein also may measure other physiologic data, and integrate that data in its reporting and analysis. It might be used at different times to treat different conditions. For example, the IVC diameter and its variation will be significantly different while the patient is standing in comparison to when the patient is sitting, prone, or supine. Therefore, the IVC monitor can also be used to track patient activity. Also, electrodes can be placed on the IVC element itself and/or on the leads leading to the device, in order to monitor, record, and communicate the heart's electrical activity.

Although a primary indication described for embodiments disclosed herein is the management of heart failure, embodiments and information collected thereby may be used for management of other conditions as well. For example, it could also be simultaneously used to manage blood volume in patients undergoing dialysis, providing direct feedback to dialysis machines to modulate total fluid volume delivered or removed. It could similarly be used to communicate with IV pumps to manage re-hydration for patients who have acute episodes of shock.

As described above, embodiments may be connected to a drug pump or stimulator to modulate the renal nerves, due to the multiple indirect effects the renal nerves have on heart failure. If a device of such embodiments is also monitoring heart rhythm status as well and detected an episode of atrial fibrillation, it could be programmed to modulate the renal nerves in that situation as well. Afferent renal nerves are known to increase systemic sympathetic tone, and increased systemic sympathetic tone increases the risk of atrial fibrillation, so temporary denervation of the renal nerves might cause the episode of atrial fibrillation to terminate.

Use of IVC Volume Measurement in Dialysis Patients

Volume management in dialysis patients can be particularly challenging, since the kidneys are not providing normal volume homeostasis. Dialysis patients typically increase their fluid volume between dialysis sessions. Since the kidneys are not making urine, excess volume needs to be removed during dialysis, along with the other waste products which dialysis filters out. However, most of the excess volume is in the cells and interstitial volume, not in the circulatory system. It takes time, typically more than an hour, for that volume to re-enter the circulatory system as other fluid is removed from the blood. The excess volume should not be removed too quickly, as that would lead to excessive hemoconcentration and potentially dangerously low blood pressure. Excessive hemoconcentration can cause myocardial stunning and other significant dangers. Moreover, it may be difficult and impractical for the care provider managing the dialysis process to track the patient's blood volume continuously during the dialysis session. Therefore, excess fluid is typically removed very gradually over the course of a dialysis session. This reduces the rate at which intracellular and extracellular fluid returns to the vascular system, and makes the overall dialysis session less efficient. An efficient and effective method to measure circulating blood volume real-time during dialysis is needed.

Secondly, it is important to remove as much volume as is safely possible over the course of the complete dialysis session. As mentioned, fluid volume builds up in patients between dialysis sessions. This leads to many potential clinical issues, including high blood pressure, fluid in the lungs, fibrosis, and heart failure. If the patients leave each dialysis session with a minimum of fluid in their systems, that increases the chances that they will not be overloaded with fluid by the time they return for their next session. However, determining whether the patient is euvolemic (has the right fluid volume) or is hyper- or hypo-volemic is challenging with current techniques. An effective method to measure final blood volume in dialysis patients at the end of dialysis sessions is therefore also an important need.

At present, blood concentration during dialysis is often measured using devices such as Fresenius' Critline or Intelomedics' CVinsight. These systems measure the patient's hematocrit and blood oxygenation to calculate the fluid volume removed from the patient. Assessing euvolemia at the end of dialysis may be done using 'BioImpedance measurement', which gives an indication of extracellular and intracellular fluid volume in the patient. These measurements are imperfect, but are the best available at this time.

Measurement of a dialysis patient's volume status using ultrasound imaging of the IVC has been studied. It gives an important physiologic reading of the patient's volume status, one which relates directly to whether the patient is truly euvolemic. However, it is user-dependent, technology-sensitive, and difficult. It also gives only a single-point measurement, and is completely impractical as a method of continuously measuring volume status.

For all of these reasons, IVC volume measurement systems embodied in the present disclosure provide an improved method of managing the dialysis patient's volume status. Described systems provide for continuous monitoring and give a true measurement of whether the patient is hyper-, hypo-, or euvolemic, and can be used to guide therapy. The IVC markers described herein, when implanted on or in the IVC wall, allow a patient's fluid volume to be monitored before, during or after a dialysis session. Because dialysis is typically conducted in a specialized facility staffed by healthcare providers, readings could be taken by trained professionals to ensure accuracy. In addition, with the patient being immobile in a chair or bed during dialysis, an ultrasound probe may be attached to the patient's skin to provide continuous monitoring of the IVC markers during the dialysis session. The IVC volume monitor may be connected directly to the dialysis machine, for closed-loop volume management. For example, an appropriate minimum blood volume may be established by the healthcare provider; for example, as an average 40% variation in IVC dimension over the respiratory cycle. The dialysis machine could then be programmed to reduce the blood volume at a measured, but relatively rapid pace until that volume is reached, and then to maintain that volume over the rest of the dialysis session. This approach would maximize the intracellular and extracellular fluid that is removed from the patient, while preventing the patient from risk of myocardial stunning, lightheadedness, or the other dangers of hypovolemia. It may be possible to shorten the dialysis session slightly as a result. At the end of the dialysis session, the IVC monitor would reconfirm that the patient was appropriately euvolemic before ending the session.

All of this discussion of volume management in dialysis patients applies equally to the management of heart failure patients who are having volume removed using an aquapheresis system such as the CHF Solutions Aquadex, or when using aggressive diuretics. It is desirable to remove the excess volume as quickly as possible, but also to allow time for the excess volume in tissue to gradually return to the bloodstream, so that overall blood volume does not drop too low, nor the blood become too concentrated.

Measurement of Volume Status in Other Vessels Besides the IVC

The discussion of the various alternative embodiments above is generally made in the context of measurement of volume in the IVC. However, these embodiments also apply to and may be used for similar measurements in the superior vena cava (SVC), right atrium, or other vessels. The variation in IVC volume over the respiratory cycle has been well documented in studies using ultrasound imaging. The mild valsalva effect of respiration causes a slight variation in thoracic pressure, which modulates the flow of blood from the IVC (in the abdomen) into the right atrium (in the thorax). Therefore, this variation may be more pronounced in the IVC than in other vessels. IVC variation may also be more sensitive to variations in right atrial pressure, which may vary less in patients with marked volume overload causing tricuspid regurgitation or reduced right ventricular filling volume. However, very sensitive measurement systems might measure similar variations in vessels that are more accessible for the placement of markers and/or for placement of a measurement device. The subclavian veins, jugular veins, and femoral veins, among others, are all potential vessels for measurement of volume and volume variation that could provide similar information about a patient's blood volume and/or heart failure status. However, the teachings of this disclosure are not so limited and may be applied by persons of ordinary skill to any vein in the body, using the sensitive measurement techniques described herein. Further features, considerations and embodiments are described below, which may be incorporated singly or multiply into one or more embodiments described above. For example, discussed above is the use of the sensor/monitor input to modify the action of cardiac pacemakers to better control the heart and circulatory system. Another embodiment or method of treating heart failure, and more specifically the fluid overload associated with heart failure, is through chemical, neural, hormonal, or electrical manipulation of the renin-angiotensin system and the degree to which the kidneys excrete or retain water.

Exemplary embodiments have been disclosed above and illustrated in the accompanying drawings. It will be understood by those skilled in the art that various changes, omissions and additions may be made to that which is specifically disclosed herein without departing from the spirit and scope of the present disclosure.

What is claimed is:

1. A heart failure interventional method with closed-loop control, comprising:

continuously or intermittently receiving from a patient-implanted vascular sensor implanted in the patient's inferior vena cava (IVC) a signal indicative of a dimension or change in dimension of the IVC, said patient-implanted vascular sensor configured to generate and wirelessly deliver said signal to a control unit outside the patient's IVC;

receiving said signal at the control unit and correlating the received signal to a patient fluid volume state; and automatically modulating a therapy delivered by a therapeutic device continuously or intermittently in a closed loop based at least in part on the correlated patient fluid volume state in response to the received signal.

2. The heart failure interventional method of claim 1, wherein said correlating comprises determining a change in vascular dimension and comparing the determined change in vascular dimension to a reference value to evaluate the patient's fluid volume status.

3. The heart failure interventional method of claim 2, further comprising generating a therapeutic device control signal within the control unit and delivering the therapeutic control signal to the therapeutic device.

4. The heart failure interventional method of claim 3, wherein said control unit is disposed remote from the therapeutic device and the method further comprises wirelessly delivering the therapeutic device control signal to the therapeutic device.

5. The heart failure interventional method of claim 3, wherein said control unit comprises a part of the therapeutic device.

6. The heart failure interventional method of claim 1, wherein the patient-implanted vascular sensor further comprises an intravascular pressure sensor.

7. The heart failure interventional method of claim 6, further comprising placing the intravascular pressure sensor in the pulmonary artery and placing the vascular dimension sensor in the inferior vena cava (IVC) or superior vena cava (SVC).

8. The heart failure interventional method of claim 1, wherein the signal indicative of a dimension or change in dimension of the IVC is intermittently received and occurs at programmed intervals.

9. The heart failure interventional method of claim 1, wherein the therapeutic device is a drug pump and said automatedly modulating the delivered therapy comprises automatedly controlling drug delivery via said drug pump.

10. The heart failure interventional method of claim 9, wherein the drug delivery comprises delivering a diuretic drug.

11. The heart failure interventional method of claim 9, wherein the drug pump is an external IV pump, and said automatedly modulating the delivered therapy comprises automatedly controlling IV drug delivery via said IV pump.

12. The heart failure interventional method of claim 9, wherein the drug pump is a patient-implanted pump delivering the drug subcutaneously or intravascularly, and said automatedly modulating the delivered therapy comprises automatedly controlling drug delivery via said patient-implanted pump.

13. The heart failure interventional method of claim 1, wherein the therapeutic device is a dialysis machine, and said automatedly modulating the delivered therapy comprises automatedly controlling patient dialysis via the dialysis machine.

14. The heart failure interventional method of claim 1, wherein the therapeutic device is a cardiac-implanted device.

15. The heart failure interventional method of claim 14, wherein the cardiac-implanted device is a pacemaker, and said automatedly modulating the delivered therapy comprises automatedly adjusting heart pacing delivered by the pacemaker.

16. The heart failure interventional method of claim 14, wherein the cardiac-implanted device is a defibrillator, and said automatedly modulating the delivered therapy comprises automatedly adjusting the defibrillator output to alter cardiac rhythm.

17. The heart failure interventional method of claim 1, wherein the therapeutic device comprises a neurostimulator or neuromodulator and the therapy delivered comprises neurostimulation or neuromodulation.

18. The heart failure interventional method of claim 17, wherein the therapy comprises neurostimulation of the spinal cord.

19. The heart failure interventional method of claim 17, wherein the therapy comprises neuromodulation of the renal nerves.

20. The heart failure interventional method of claim 1, further comprising implanting the wireless vascular sensor within the IVC of the patient.

21. The heart failure interventional method of claim 1, further comprising continuously or intermittently receiving from a patient-implanted cardiac monitor a second signal containing information indicative of patient cardiac health status, and wherein said automatedly modulating the delivered therapy further comprises modulating said delivered therapy based on said second signal in combination with said signal indicative of the dimension or change in dimension of the IVC.

22. The heart failure interventional method of claim 21, wherein the patient-implanted cardiac monitor comprises one or more of a cardiac rhythm monitor and a cardiac output monitor.

23. A heart failure interventional method with closed-loop control based on real-time patient fluid status, comprising:

implanting a wireless vascular lumen dimension sensor in a patient vena cava;

wirelessly receiving from said vascular lumen dimension sensor implanted in the vena cava a signal indicative of a dimension or change in dimension of the vena cava, wherein said signal is continuous or interment and when intermittent said intermittent signal occurring at programmed intervals;

correlating the received signal from the vascular lumen dimension sensor to a patient fluid volume state as said signal is received;

receiving the patient fluid volume state in a therapeutic device controller; and automatedly modulating a therapy delivered by the therapeutic device communicating with the therapeutic device controller in response to the received patient fluid volume state correlated from the vena cava lumen dimension sensor signal.

24. A heart failure interventional system with closed-loop control, comprising:

a cardiac health status monitoring system comprising a wireless vascular implant and control unit, wherein the wireless vascular implant is configured to generate and wirelessly deliver a signal containing information indicative of a patient cardiac health status parameter to the control unit, said control unit being configured to process said signal to determine a value for the cardiac health status parameter continuously or at programed intervals;

a therapeutic device including a processor configured to execute instructions to modulate therapeutic intervention continuously or at programed intervals based at least in part on the determined value for the patient cardiac health status parameter; and a communication link between said monitoring system and said therapeutic device; and wherein the wireless vascular implant is a wireless vena cava dimension sensor and said patient cardiac health status parameter comprises a dimension or change in dimension of the vena cava.

25. The heart failure interventional system of claim 24, wherein said cardiac health status monitoring system control unit is disposed within the therapeutic device processor.

26. The heart failure interventional system of claim 24, wherein said control unit is further configured to corelate the dimension or change in dimension of the vena cava to a patient fluid status.

27. The heart failure interventional system of claim 26, wherein the control unit is configured to:

determine a sensed value for the sensed dimension;

determine a changed value by comparing the sensed value to a reference value or by directly using a sensed change in value;

evaluating patient fluid status based on the determined changed value; and modulating said therapy delivery based on the evaluated patient fluid status.

28. The heart failure interventional system of claim 24, wherein said cardiac health status monitoring system further comprises at least a second sensing device comprising at least one or more of an implanted vascular pressure sensor, a respiratory rate monitor, cardiac rhythm monitor, blood oxygen saturation sensor, or cardiac output monitor.

29. The heart failure interventional system of claim 28, wherein:

said system comprises one or more therapeutic devices; and said one or more therapeutic devices comprise one or more processors configured to execute instructions to modulate delivered therapies based on said vena cava dimension or change in dimension information and information derived from the at least one second sensing device.

30. The heart failure interventional system of claim 24, wherein the therapeutic device is a drug pump comprising a controller configured to automatedly modulate drug delivery to the patient based at least in part on the signal generated by the vascular implant of said monitoring system.

31. The heart failure interventional system of claim 30, wherein the drug delivery comprises a diuretic drug.

32. The heart failure interventional system of claim 30, wherein the drug pump is an external IV pump.

33. The heart failure interventional system of claim 30, wherein the drug pump is a patient-implanted pump.

34. The heart failure interventional system of claim 24, wherein the therapeutic device comprises a dialysis machine configured to automatedly modulate patient dialysis based at least in part on the signal generated by the vascular implant of said monitoring system.

35. The heart failure interventional system of claim 24, wherein the therapeutic device comprises a cardiac-implanted device.

36. The heart failure interventional system of claim 35, wherein the cardiac-implanted device is a pacemaker controlled by a pacing algorithm, said pacing algorithm including inputs for values correlated to the signal generated by the wireless vascular implant configured to automatedly adjust heart pacing delivered by the pacemaker based on the pacing algorithm.

37. The heart failure interventional system of claim 35, wherein the cardiac-implanted device is a defibrillator.

38. The heart failure interventional system of claim 24, wherein the therapeutic device comprises at least one of a neurostimulator or neuromodulator.

39. The heart failure interventional system of claim 24, wherein said communications link is a wireless communications link.

40. A heart failure interventional system with closed-loop control based on real-time patient fluid status, comprising:

an inferior vena cava (IVC) fluid monitoring system comprising a wireless IVC implant configured to generate and wirelessly deliver to an external controller a signal indicative of a dimension or change in dimension of the IVC, said dimension or change in dimension being correlated to a patient fluid state by the external controller continuously or at programed intervals;

one or more heart failure therapeutic devices controlled by one or more processors configured to execute instructions to modulate therapeutic intervention continuously or at programed intervals based on patient fluid state as determined by the IVC fluid monitoring system; and a communications link between said IVC fluid monitoring system and said one or more processors.

* * * * *